(12) United States Patent
Lyngstadaas et al.

(10) Patent No.: US 9,629,941 B2
(45) Date of Patent: Apr. 25, 2017

(54) HYDROGEL COATED SCAFFOLD

(71) Applicant: CORTICALIS AS, Rud (NO)

(72) Inventors: S. Petter Lyngstadaas, Nesoddtangen (NO); Havard J. Haugen, Oslo (NO); Hanna Tiainen, Oslo (NO)

(73) Assignee: CORTICALIS AS, Rud (NO)

( * ) Notice: Subject to any disclaimer, the term of this patent is extended or adjusted under 35 U.S.C. 154(b) by 0 days.

(21) Appl. No.: 14/427,853

(22) PCT Filed: Sep. 18, 2013

(86) PCT No.: PCT/EP2013/069355
§ 371 (c)(1),
(2) Date: Mar. 12, 2015

(87) PCT Pub. No.: WO2014/044704
PCT Pub. Date: Mar. 27, 2014

(65) Prior Publication Data
US 2015/0250923 A1    Sep. 10, 2015

(30) Foreign Application Priority Data

Sep. 18, 2012 (SE) .................................. 1251043-4

(51) Int. Cl.
| | |
|---|---|
| *A61L 27/34* | (2006.01) |
| *A61L 27/06* | (2006.01) |
| *A61L 27/10* | (2006.01) |
| *A61L 27/54* | (2006.01) |
| *A61L 27/56* | (2006.01) |
| *A61L 27/38* | (2006.01) |
| *A61L 27/42* | (2006.01) |
| *A61L 27/52* | (2006.01) |

(52) U.S. Cl.
CPC ............... *A61L 27/34* (2013.01); *A61L 27/06* (2013.01); *A61L 27/10* (2013.01); *A61L 27/3821* (2013.01); *A61L 27/3834* (2013.01); *A61L 27/425* (2013.01); *A61L 27/52* (2013.01); *A61L 27/54* (2013.01); *A61L 27/56* (2013.01); *A61L 2300/25* (2013.01); *A61L 2300/412* (2013.01); *A61L 2300/422* (2013.01); *A61L 2300/64* (2013.01); *A61L 2400/18* (2013.01); *A61L 2420/02* (2013.01); *A61L 2420/04* (2013.01); *A61L 2420/06* (2013.01); *A61L 2430/02* (2013.01); *A61L 2430/12* (2013.01)

(58) Field of Classification Search
CPC .......... A61L 27/34; A61L 27/06; A61L 27/10; A61L 27/54; A61L 27/56; A61L 2300/25; A61L 2300/412; A61L 2300/422; A61L 2400/18; A61L 2420/02; A61L 2430/02; A61L 2430/12; A61L 27/3821; A61L 27/3834; A61L 27/425; A61L 27/52
See application file for complete search history.

(56) References Cited

U.S. PATENT DOCUMENTS

| | | | | |
|---|---|---|---|---|
| 6,306,176 | B1 * | 10/2001 | Whitbourne | .......... A61L 29/085 427/2.24 |
| 6,309,380 | B1 * | 10/2001 | Larson | ................. A61K 9/0024 128/898 |
| 2005/0142163 | A1 * | 6/2005 | Hunter | .................. A61B 17/11 424/423 |
| 2015/0209474 | A1 * | 7/2015 | Haugen | .................. A61L 27/06 424/423 |

FOREIGN PATENT DOCUMENTS

WO    WO2008/078164    *    7/2008    ............. A61L 27/00

* cited by examiner

*Primary Examiner* — Sean Basquill
(74) *Attorney, Agent, or Firm* — Cermak Nakajima & McGowan LLP; Malcolm K. McGowan

(57) ABSTRACT

The present document is directed to a titanium dioxide scaffold comprising a hydrogel coating comprising a biologically active substance. Also disclosed is a method for producing a thin hydrogel coating on a titanium dioxide scaffold and uses of the hydrogel coated scaffolds as medical implants.

14 Claims, 56 Drawing Sheets

HYDROGEL COATED SCAFFOLD

CROSS-REFERENCE TO RELATED APPLICATION

This application is a National Stage Application under 35 U.S.C. §371 and claims the benefit of International Application No. PCT/EP2013/069355, filed Sep. 18, 2013, which claims priority to Swedish Application No. 1251043-4, filed on Sep. 18, 2012. The disclosure of the foregoing applications are hereby incorporated by reference in their entirety.

TECHNICAL FIELD

The present document is directed to medical implants having a scaffold structure. In particular, the present document discloses a titanium dioxide scaffold which has a hydrogel coating comprising a biologically active substance and uses thereof.

BACKGROUND OF INVENTION

Conditions such as trauma, tumours, cancer, periodontitis and osteoporosis may lead to bone loss, reduced bone growth and volume. For these and other reasons it is of great importance to find methods to improve bone growth and to regain bone anatomy.

Natural bone tissue formation from osteogenic cells with the aid of a three-dimensional scaffold offers an alternative to autografts and allografts to repair and regenerate lost bone. A well-constructed scaffold provides a suitable surface for cells to attach and adhere with a porous and well interconnected network guiding the development of new bone, supporting migration, proliferation and differentiation of bone-forming cells and vascularization of the ingrowth tissue. Although several polymers and bioceramics have been developed for their use in bone tissue engineering, their low mechanical properties have limited their use for load-bearing applications.

Titanium dioxide ($TiO_2$) is a biocompatible material, which has also been reported to have bioactive properties and a certain degree of bacteriostatic effect. Therefore, ceramic $TiO_2$ has been studied as a material for bone tissue engineering purposes. High porous and well-interconnected $TiO_2$ scaffolds with high mechanical strength achieving values of 90% of porosity and of 1.63-2.67 MPa of compressive strength have been recently developed (Tiainen et al. 2010) and their biocompatibility and osteoconductive properties have been demonstrated in vitro and in vivo.

Attempts have been made to e.g. improve the scaffolds biocompatibility, to improve osseointegration, inhibit infection and inflammation by coating the implant structure with different kinds of biologically active molecules. However, in order to be able to perform their intended function on the implant after implantation, the biologically active molecules need to be coated onto the implant in a manner that allows their release, that does not detrimentally harm their biological activity and that does not cause negative body reactions etc.

Hydrogels have been used for different applications in tissue engineering such as space filling agents, as delivery vehicles for bioactive molecules, and as three-dimensional structures that organize cells and present stimuli to direct the formation of a desired tissue. A hydrogel typically comprises a network of polymer chains that are hydrophilic and highly absorbent and can contain over 99.9% water. Alginate is one example of a polymer chosen to form hydrogels for tissue engineering, having been used in a variety of medical applications including cell and/or growth factor encapsulation and drug stability and delivery. Alginate is a hydrophilic and linear polysaccharide copolymer of β-D-mannuronic acid (M) and α-L-glucuronic acid (G) monomers. Alginate gel is formed when divalent cations such as $Ca^{2+}$, $Ba^{2+}$ or $Sr^{2+}$; cooperatively interact with blocks of G monomers creating ionic bridges between different polymer chains. Due to favorable properties for a biomaterial, such as nontoxicity, biodegradability, and ease of processing into desired shape under normal physiological conditions, alginate has been studied extensively in tissue engineering, including the regeneration of skin, cartilage, bone, liver and cardiac tissue.

Chitosan is the deacetylated derivative of chitin, a natural component of shrimp and crab shells. It is a biocompatible, pH-dependent cationic polymer, which is soluble in water up to pH 6.2. Chitosan is more stable than alginates, but are quickly broken down in low pH, e.g. conditions presents in inflamed, infected or hypoxic tissues. Chitosan itself is also believed to have anti-inflammatory properties. Other hydrogels like starches and collagen based gels have similar characteristics, but are more rapidly broken down by local tissue factors like collagenases. Celluloses are also pH dependent and can be fashioned in several different chemical modifications depending on the use, mechanical strength etc. needed. PLA and PGA are rapidly broken down to organic acids (i.e. lactic acid) that can have beneficial local effects on tissues, infections and on the breakdown rate of other hydrogels (e.g. chitosan) when used in combinations.

Hyaluronic acid is another important hydrogel with biological effects. It is an important constituent of cartilage and is commonly used in joints, for wound healing and in eyes. It is mildly anti-inflammatory and is believed to stimulate regeneration of certain types of connective tissues like cartilage, ligaments and corneal cells. PEG is a very biocompatible hydrogel that is highly flexible with regard to strength, crosslinking for designed break-down rates etc., and a gel that can be chemically linked to biological molecules to provide a controlled sustained release vehicle that can be designed for a multitude of conditions.

The mixing and gelling of some PEG differ from most other hydrogels in that it cannot simply be dissolved in water and allowed to gel in the presence of ions (like almost all biological hydrogels like chitosan, celluloses, starches, collagens, agaroses), but need a chemical reactant like mercaptoethanol to form stable crosslinks and become a gel.

However other PEG conjugates can also become gelated by different means such as UV light, crosslinking by ionic interactions, the addition of divalent cation salts and condensation reactions (condensation reactions between hydroxyl groups or amines with carboxylic acids or derivatives hereof are frequently applied for the synthesis of polymers to yield polyesters and polyamides, respectively, PEG).

However, there still is a need in the field of medical implants and tissue engineering for implant structures providing e.g. a supporting structure, which are biocompatible and/or which improve the Integration of the implant in a body.

SUMMARY OF INVENTION

One object of the present document is to provide a titanium dioxide scaffold suitable as a supporting structure, such as a medical implant, which is biocompatible and/or which has improved integration properties.

This object is obtained by the present disclosure which in one aspect is directed to a titanium dioxide scaffold, wherein at least part of the surface of said titanium dioxide scaffold is provided with a hydrogel coating comprising at least one biologically active substance. Such a titanium dioxide scaffold may be denoted a hydrogel coated titanium dioxide scaffold. The hydrogel coating typically comprises at least one polymer selected from the group consisting of alginate, chitosan, hyaluronic acid, poly ethylene glycol (PEG), cellulose, poly(acrylic acid) (PAA), poly(glycolic acid) (PGA), poly(lactic acid) (PLA), PLA-PGA, PLA-PEG, dextran, dextran-PEG, starch, collagen based gels, agaroses, pluronic acid, heparan sulfate, glycosaminoglycans, polyethylene oxide (PEO), copolymer of ethylene oxide and propylene oxide (P(EO-co-PO)), and pluronic/poloxamer although other polymers being able to form hydrogel may also be used as disclosed elsewhere herein. The hydrogel is typically formed by using polymer having a molecular weight of about 1 000-1 000 000 g/mol, such as 1000-200 000 g/mol.

The present document is also directed to a method for producing a titanium dioxide scaffold comprising a hydrogel coating comprising a biologically active substance disclosed herein, said method comprising the steps of:
a) providing a titanium dioxide scaffold,
b) providing an polymer solution comprising a biologically active substance(s) and about 1-10% w/v of a polymer selected from the group consisting of alginate, chitosan, hyaluronic acid, poly ethylene glycol (PEG), cellulose, poly(acrylic acid) (PAA), poly(glycolic acid) (PGA), poly(lactic acid) (PLA), PLA-PGA, PLA-PEG, dextran, dextran-PEG, starch, collagen based gels, agaroses, pluronic acid, heparan sulfate, glycosaminoglycans, polyethylene oxide (PEO), copolymer of ethylene oxide and propylene oxide (P(EO-co-PO)), and pluronic/poloxamer, to at least part of said titanium dioxide scaffold and then centrifuging the titanium dioxide scaffold,
c) effecting gelation of the polymer provided to the titanium dioxide scaffold in step b); and
d) optionally drying the titanium dioxide scaffold,
wherein steps b) and c) optionally are repeated at least once.

The present document is also directed to a titanium dioxide scaffold comprising a hydrogel coating comprising a biologically active substance obtainable or obtained by this method.

The present document is also directed to a medical implant comprising the titanium dioxide scaffold comprising a hydrogel coating comprising a biologically active substance and such a scaffold for use as a medical implant.

Also disclosed it the hydrogel coated titanium dioxide scaffold or a medical implant comprising it for the regeneration, repair, substitution and/or restoration of tissue, such as bone and the hydrogel coated scaffold or a medical implant comprising it for use for the regeneration, repair, substitution and/or restoration of tissue, such as bone Also disclosed is the use of a hydrogel coated titanium dioxide scaffold for the preparation of a medical implant for the regeneration, repair, substitution and/or restoration of tissue.

Further disclosed is a method for the regeneration, repair, substitution and/or restoration of tissue comprising the Implantation into a subject in need thereof of a hydrogel coated titanium dioxide scaffold or a medical implant comprising such as scaffold.

Other features and advantages of the invention will be apparent from the following detailed description, drawings, examples, and from the claims.

DEFINITIONS

"Scaffold" in the present context relates to an open porous structure. Scaffold may in the present context be abbreviated "SC". By "titanium dioxide scaffold" is meant a scaffold comprising predominantly titanium dioxide as the building material for the scaffold structure, i.e. titanium dioxide Is the main substance responsible for forming the scaffold structure. The titanium dioxide scaffold therefore has more than 50 wt % titanium dioxide, such as about 51 wt %, 60 wt %, 70 wt %, 80 wt %, 90 wt %, 95 wt %, 96 wt %, 97 wt %, 98 wt %, 99 wt % or 100 wt % titanium dioxide, such as about 51-100 wt %, 60-100 wt %, 60-90 wt %, 70-100 wt %, 70-90 wt %, 80-90 wt %, or 80-95 wt % titanium dioxide. The titanium dioxide scaffold may thus comprise or consist of titanium dioxide as the building material for the scaffold.

By "pore diameter" is in the context of the present document intended the hydraulic diameter of a pore without its surrounding walls. The hydraulic diameter is well known to the person skilled in the art and is defined as 4.area of a pore divided by the circumferential length of the pore.

"Fractal dimension strut" is a statistical quantity that gives an indication of how completely a fractal appears to fill space, as one zooms down to finer and finer scales. There are many specific definitions of fractal dimension and none of them should be treated as the universal one. A value of 1 pertains to a straight line. The higher the number the more complex is the surface structure. Fractal dimension is in the present document calculated using the Kolmogorov or "box counting" method (Liebovitch et al. 1989). It is calculated in both 2d and 3d in Skyscan CTAn, Kontich, Belgium. The surface or volume is divided into an array of equal squares or cubes, and the number of squares containing part of the object surface is counted. This is repeated over a range of box sizes such as 3-100 pixels. The number of boxes containing surface is plotted against box length in a log-log plot, and the fractal dimension is obtained from the slope of the log-log regression.

"Total porosity" is in the present context defined as all compartments within a body which is not a material, e.g. the space not occupied by any material. Total porosity involves both closed and open pores.

By "inner strut volume" is meant the volume of the inner lumen of the strut.

By "sintering", "sinter" and the like is meant a method for making objects from powder, by heating the material (below its melting point) until its particles adhere to each other.

Sintering is traditionally used for manufacturing ceramic objects, and has also found uses in such fields as powder metallurgy.

A "medical prosthetic device, "medical implant", "implant" and the like in the present context relates to a device intended to be implanted into the body of a vertebrate animal, such as a mammal, e.g. a human mammal. Implants in the present context may be used to replace anatomy and/or restore any function of the body. Examples of such devices include, but are not limited to, dental implants and orthopaedic implants. In the present context, orthopedic implants includes within its scope any device intended to be implanted into the body of a vertebrate animal, in particular a mammal such as a human, for preservation and restoration of the function of the musculoskeletal system, particularly joints and bones, including the alleviation of pain in these structures. In the present context, dental implant includes within its scope any device intended to be implanted into the oral cavity of a vertebrate animal, in particular a mammal such as a human, in tooth restoration procedures. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation may alone be referred to as an implant even if other parts are to be connected thereto. Orthopedic and dental implants may also be denoted as orthopedic and dental prosthetic devices as is clear from the above.

In the present context, "subject" relate to any vertebrate animal, such as a bird, reptile, mammal, primate and human.

By "ceramics" are in the present context meant objects of inorganic powder material treated with heat to form a solidified structure.

By "biologically active substance" is meant a substance that may influence a biological process, i.e. it has a biological activity. A biologically active substance may be a small molecule, such as an inorganic ion or a larger molecule, such as a protein, and even a complex structure, such as a cell. Examples of biologically active substances suitable for use in the context of the present document are disclosed below. A biologically active substance may in the present context also be denoted a "biomolecule".

By "soft tissue" is in the context of the present document intended tissues that connect, support, or surround other structures and organs of the body, not being bone. Soft tissue includes ligaments, tendons, fascia, skin, fibrous tissues, fat, synovial membranes, epithelium, muscles, nerves and blood vessels.

By "hard tissue" is in the context of the present document intended mineralized tissues, such as bone and teeth, and cartilage. Mineralized tissues are biological tissues that incorporate minerals into soft matrices.

DETAILED DESCRIPTION OF THE INVENTION

Figure 1:
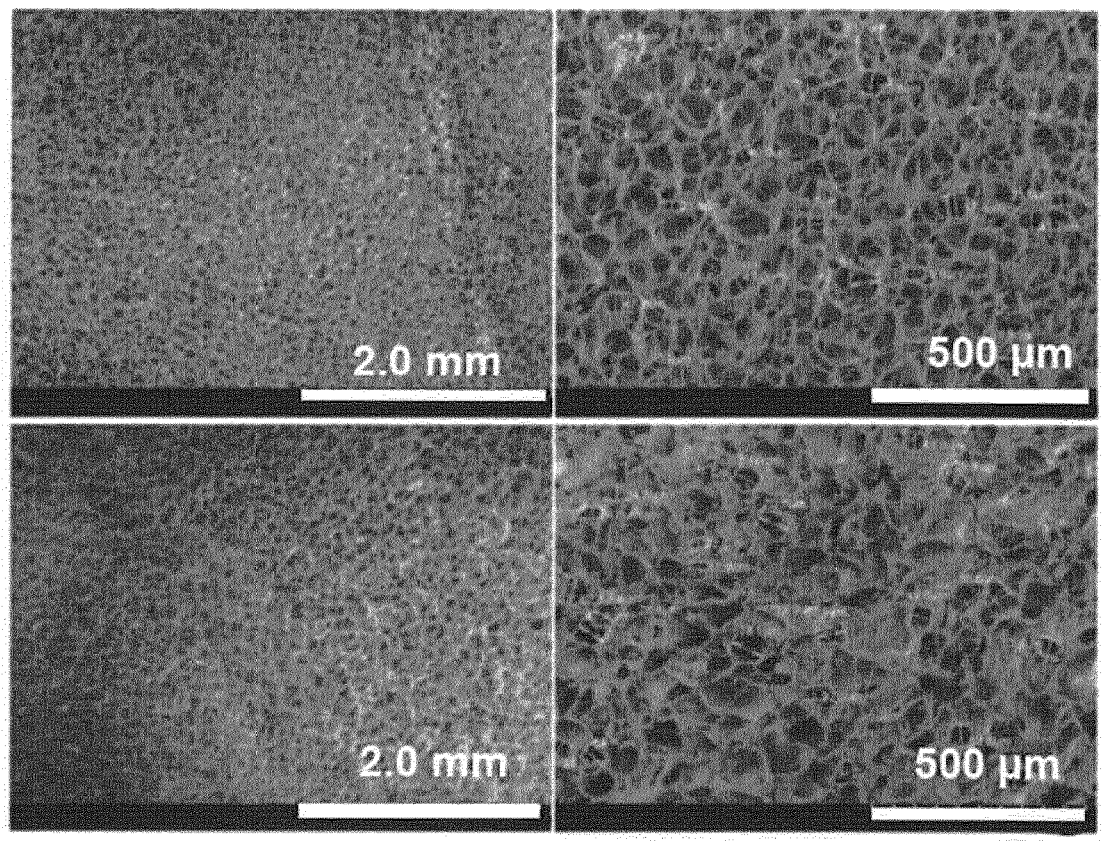
FIG. 1. Microstructure of 2% of alginate (A and B) and 2% of alginate containing synthetic peptide (C and D) gelled by 300 mM of $CaCl_2$. Observation by SEM at ×25 (A and C) and ×100 of magnification (B and D). This gel is not present on a titanium dioxide scaffold and not prepared by the method for producing a titanium dioxide scaffold comprising an alginate coating disclosed herein. Therefore, this gel adopts a porous structure.

The present document discloses a titanium dioxide scaffold, wherein at least part of the surface of said titanium dioxide scaffold is provided with a hydrogel coating which hydrogel coating comprises at least one biologically active substance (herein also denoted a biomolecule).

The titanium dioxide scaffold with the hydrogel coating comprising at least one biologically active substance may in the context of the present document also be denoted a "titanium dioxide scaffold comprising a hydrogel coating", a "hydrogel coated titanium dioxide scaffold" and the like. The surface which is provided with the hydrogel may be one or more parts or the whole of the outer surface of the titanium dioxide scaffold but also the surface of part of or the majority of the pores inside the scaffold (the walls of the pores). It is to be understood that the hydrogel coating comprises at least one biologically active substance, unless expressly clear from the context that no such biologically active substance is present. The presence of the hydrogel coating of the titanium dioxide scaffold allows the delivery of biologically active substance which may improve the scaffolds integration, biocompatibility etc. However, the substance(s) making up the hydrogel coating may also in themselves have a biological activity.

A hydrogel may be defined as a gel that contains water. The hydrogel coating disclosed herein comprises a network of polymer chains that are hydrophilic and highly absorbent and therefore the hydrogel coating adopts a gel-like state when wet. However, it is to be understood that a certain amount of moisture is required for the hydrogel coating to adopt this gel-like state. Therefore, when a hydrogel coated titanium dioxide scaffold is e.g. dried or stored in a dry place, the hydrogel will rather be in the form of a thin, dehydrated, film layer (aka a "xerogel"). However, once the hydrogel coated titanium dioxide scaffold is subjected to a moister environment, such as when implanted in a body or when immersed in an aqueous solution, this film layer will adopt a hydrogel appearance again. Unless expressly evident from the context, when a hydrogel is referred to in the present document, this is to be understood to encompass both moist and dry forms of the gel.

The hydrogel is formed from a high molecular weight polymer having a molecular weight of about 1 000-1 000 000 g/mol, such as 1000-200 000 g/mol, such as alginate, chitosan, hyaluronic acid, poly ethylene glycol (PEG), cellulose, poly(acrylic acid) (PAA), poly(glycolic acid) (PGA), poly(lactic acid) (PLA), PLA-PGA, PLA-PEG, dextran, dextran-PEG, starch, collagen based gels, agaroses, pluronic acid, heparan sulfate, glycosaminoglycans, polyethylene oxide (PEO), copolymer of ethylene oxide and propylene oxide (P(EO-co-PO)), and pluronic/poloxamer.

Chitosan is more stable than alginates, but are quickly broken down in low pH, e.g conditions presents in inflamed, infected or hypoxic tissues. Chitosan itself is also believed to have anti-inflammatory properties. Other hydrogels like starches and collagen based gels have similar characteristics, but are more rapidly broken down local tissue factors like collagenases. Celluloses are also pH dependent and can be fashioned in several different chemical modifications depending on the use, mechanical strength etc. needed. PLA and PGA are rapidly broken down to organic acids (i.e. lactic acid) that can have beneficial local effects on tissues, infections and on the breakdown rate of other hydrogels (e.g. chitosan) when used in combinations. Hyaluronic acid is another important hydrogel with biological effects. It is an important constituent of cartilage and is commonly used in joints, for wound healing and in eyes. It is mildly anti-inflammatory and is believed to stimulate regeneration of certain types of connective tissues like cartilage, ligaments and corneal cells. PEG is a very biocompatible hydrogel that is highly flexible with regard to strength, crosslinking for designed break-down rates etc., and a gel can that be chemically linked to biological molecules to provide a controlled sustained release vehicle that can be designed for a multitude of conditions.

Further examples of polymers which may be used to form the hydrogel include, but are not limited to: poly(propylene oxide) (PPO), poly(butylene oxide) (PBO), poly(2-hydroxyethyl methacrylate), hydroxyethyl methacrylate, poly(ethylene glycol) methacrylate, acrylic acid acrylamide, N-isopropylacrylamide, poly(vinyl alcohol) (PVA), polyacrylamide (PAAm), poly(N-vinyl pyrrolidone) (PNVP), poly(hydroxyethyl methacrylate) PHEMA), poly(ethylene oxide) (PEO), poly(ethylene glycol) monomethyl ether (PEGME), methyl cellulose such as carboxymethyl cellulose, poly(hydroxyethyl methacrylate) (PHEMA) copolymerized with NVP methacrylic acid (MAA), butyl methacrylate (BMA), methyl methacrylate (MMA), 3-methoxy-2-hydroxypropylmethacrylate (MHPM), PHEMA/poly(ethyleneterephthalate) (PTFE), PHEMA, P(HEMA-co-MMA), P(HEMA-b-siloxane), PVA, poly(acrylic acid) (PAA), poly (glyceriyl methacrylate), HEMA, polycyanoacrylates, fumaric acid-PEG, sebacic acid/1,3-bis(p-carboxyphenoxy) propane (P (CPP-SA)) PHEMA, PVA, PNVP, poly(ethylene-co-vinyl acetate) (PEVAc), poly(acrylamide) (PAAm), poly (diethylaminoethyl methacrylate) (PDEAEMA), poly (dimethylaminoethyl methacrylate), (PDMAEMA), poly(methacrylic acid-grafted-poly(ethylene glycol)), (P(MAA-g-EG)), poly (acrylic acid-grafted-poly(ethylene glycol) (P(PAA-g-EG)), poly(N-isopropyl acrylamide) (PNIPAAm), PNIPAAm/PAA, polyglycol-alginate, collagen based gels (gelatins), and heparan sulfate and its analogues and other glycosaminoglycans.

The hydrogel may function as a carrier for the biologically active substance but some polymers may also have a biological activity in themselves (e.g. chitosan, heparan sulfate, hyaluronic acid and collagens) or be broken down to biologically active metabolites by natural processes in a body (e.g. PLA, PGA, collagens, heparan sulfate analogues).

The polymer is typically a high molecular weight polymer, i.e. a polymer having a molecular weight ($M_w$) of about 1 000-1 000 000 g/mol, such as about 1 000-200 000 g/mol, 10 000-600 000 g/mol, 10 000-100 000 g/mol, 100 000-300 000 g/mol, 250 000-600 000 g/mol, 50 000-150 000 g/mol, 50 000-200 000 g/mol, or 50 000-100 000 g/mol. The hydrogel coating may comprise one or more types of polymers being mixed with each other when preparing the hydrogel. Alternatively, the hydrogel may be built up by different layers of hydrogel that may comprise different polymers or different mixtures of polymers.

By varying the biologically active molecule(s) in the hydrogel and the polymer(s) the respective hydrogel layer is built up of and/or the polymer(s) in the different hydrogel layers, the desired biological function of the hydrogel may be obtained depending on the intended function of the hydrogel coated titanium dioxide scaffold in a subject.

When the hydrogel is an alginate hydrogel, the alginate may e.g. be sodium alginate, potassium alginate, calcium alginate, and strontium alginate. Alginate is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks) or alternating M and G-residues (MG-blocks). The characteristics of the alginate changes upon different ratio of the M and G blocks, as well as it sequence. The alginate may comprise a minimum of about 60% of guluronate monomers.

The hydrogel is present on the outer surface of the titanium dioxide scaffold, but it may also in different degrees penetrate the scaffold and coat the walls of the pores inside the scaffold or fill up the scaffold pore space.

The hydrogel coating may have a wet thickness of at least 1 μm, such as 1-20 μm or 1-10 μm. Such a thin hydrogel may coat at least part of the outer surface of the titanium dioxide scaffold but may also coat the walls of the pores inside the scaffold. The hydrogel coating may comprise one or more subsequently formed layers of hydrogel. The hydrogel coating may therefore be built up by 1-10 hydrogel layers, such as 2-6, 2-4, 3 or 4 layers. A thin thickness of the hydrogel coating may be advantageous as such a thin coating will not substantially block the pore openings of the titanium dioxide scaffold, even if the pore diameter of course is somewhat reduced due to the hydrogel coating. Some initial blocking of the scaffold pores may occur even when a thin hydrogel coating is prepared, but in a biological environment, a certain degradation of the blocking hydrogel coating was seen in those pores that remained blocked right after the coating process (see Example 2). The substantial lack of pore blocking is advantageous as cell growth into the titanium dioxide scaffold thereby may be improved as the pores, despite the hydrogel coating, are readily accessible for penetration by cells and tissue.

Another advantage with a thin hydrogel coating that is also formed in the walls of the scaffold pores is that there will be a very large surface-to-volume ratio as compared to when the hydrogel coating is formed basically only on the outer surface of the scaffold.

This will affect the release profile of the biologically active substance included in the hydrogel coating. Also, even if the hydrogel coating would flake off from the outer surface of the titanium dioxide scaffold, if the hydrogel is also present inside the scaffold not all the hydrogel is lost from the scaffold by the flaking off, but hydrogel with biomolecule(s) would still be present inside the scaffold.

The size of the biomolecule may affect the choice of the number of hydrogel layers and/or the total thickness of the hydrogel layer. A smaller biomolecule (i.e. having a lower Mw, such as doxycycline) diffuses out of the hydrogel coating faster than a larger biomolecule. Therefore, if a delayed release of a smaller biomolecule is desirable, a thicker hydrogel coating is required. On the other hand, for a larger biomolecule, the release rate from the hydrogel coating is more dependent on degradation of the hydrogel and the biomolecule does not diffuse out of the hydrogel coating as fast as a smaller biomolecule. Therefore, a thinner hydrogel coating may be used for a larger biomolecule. By knowing the size of the biomolecule and the desirable release rate, the thickness of the hydrogel coating may therefore be adjusted to achieve the desirable release rate.

Alternatively, the hydrogel may fill up the space inside the titanium dioxide scaffold, i.e. fill up the pores in different extents (as well as optionally being present on the outer surface of the titanium dioxide scaffold). This may be particularly advantageous when cells (for example of cell types, see elsewhere herein), such as stem cells, are to be incorporated into the titanium dioxide scaffold, as this allows a large number of cells to be deposited inside the scaffold pores. For example about 50-100%, 60-100%, 70-100%, 80-100%, 90-100% or 90-99% of the total pore volume inside the titanium dioxide scaffold may be filled up with a hydrogel coating.

The method for producing a hydrogel coated titanium dioxide scaffold(s) disclosed herein provides a titanium dioxide scaffold wherein at least part of the scaffold is provided with a hydrogel coating comprising a biologically active substance(s). This document is therefore also directed to a titanium dioxide scaffold comprising a hydrogel coating comprising a biologically active substance(s), obtainable or obtained by the methods disclosed herein.

Methods for Forming the Hydrogel Coating Comprising a Biologically Active Substance(s)

One example of a method for producing the herein disclosed titanium dioxide scaffold comprising a hydrogel coating comprising a biologically active substance is a method comprising the steps of:
  a) providing a titanium dioxide scaffold,
  b) providing a polymer solution comprising a biologically active substance(s) and about 1-10% w/v of a polymer selected from the group consisting of alginate, chitosan, hyaluronic acid, poly ethylene glycol (PEG), cellulose, poly(acrylic acid) (PAA), poly(glycolic acid) (PGA), poly(lactic acid) (PLA), PLA-PGA, PLA-PEG, dextran, dextran-PEG, starch, collagen based gels, agaroses, pluronic acid, heparan sulfate, glycosaminoglycans, PEO, P(EO-co-PO), and pluronic/poloxamer, to at least part of said titanium dioxide scaffold and then centrifuging the titanium dioxide scaffold,
  c) effecting gelation of the polymer provided to the titanium dioxide scaffold in step b); and
  d) optionally drying the titanium dioxide scaffold,
  wherein steps b) and c) optionally are repeated at least once.

The method may also consist of the above steps a)-d), wherein steps b) and c) optionally are repeated at least once. When steps b) and c) are repeated, a hydrogel coating comprising two or more hydrogel layers is built up.

The titanium dioxide scaffold of step a) is a titanium dioxide scaffold as disclosed elsewhere herein.

The polymer solution is an aqueous solution comprising at least one of the polymers listed herein as being suitable for forming the hydrogel (or a polymer having a similar function) at a concentration of about 1-10% w/v. The polymer solution may be prepared by dissolving the polymer in distilled water or a suitable buffer, such as phosphate buffered saline, by stirring until the polymer is dissolved, preferably at room temperature, e.g. for 1 hour to overnight (e.g. 1-24 hours). The biologically active substance(s) is a biologically active substance as disclosed elsewhere herein and is preferably added to the polymer solution. The concentration of the biologically active substance, when added to the polymer solution, of course depends on the specific biologically active substance and/or its intended function in the body. Typically, it's concentration in the polymer solution is in the range of micrograms, although it may range from 1 ng-1 mg/ml, such as 500 ng/ml-500 µg/ml, or 0.5-500 µg/ml.

In order to provide the polymer solution to the titanium dioxide scaffold, the titanium dioxide scaffold may be immersed into a polymer solution. This may take place under agitation, e.g. via an orbital shaker at about 100 rpm/min. The agitation helps in spreading the polymer solution in the porous network of the scaffold. Typically, the titanium dioxide scaffold is immersed for a time period of about 10 min to 2 hours, such as 1-2 hour, e.g. 1 hour. The immersion typically takes place at room temperature.

After immersion into a polymer solution, excess solution is preferably removed typically by careful centrifugation of the titanium dioxide scaffold, such as at about 200-300×g, for a short time period, such as 0.5-2 min, e.g. 1 min.

In order to effect gelation of the polymer in step c), standard methods, known by the person skilled in the art, may be used. Depending on the specific polymer used for preparing the hydrogel coated titanium dioxide scaffold, the gelation in step c) may be effected in different ways, such as by changing the pH or temperature, by the addition of a salt, exposure to light of certain wavelengths, use of crosslinking agents etc.

When alginate is used as a polymer, in step c) the titanium dioxide scaffold is provided with a divalent cation salt solution. The divalent cation salt solution (also denoted "divalent cation solution" herein) is an aqueous solution comprising at least one salt of a divalent cation, such as $Ca^{2+}$, $Mg^{2+}$, $Ba^{2+}$ or $Sr^{2+}$. Example of suitable divalent cation salts include, but are not limited to, $CaCl_2$, $SrCl_2$, $SrCO_3$, $SrPO_4$, $CaCO_3$, $CaPO_4$, $MgCl_2$, $MgCO_3$, and $MgPO_4$. The concentration of the divalent cation salt in this solution is typically about 15-500 mM, such as about 15-150, 20-500 mM, 20-100 mM, 20-400 mM, 200-400 mM, 250-350 mM, 30-80 mM, 40-60 mM, 45-55 mM or about 50 mM. Preferably, the concentration is about 20-100 mM. Preferably, the divalent cation salt is $CaCl_2$. To provide the titanium dioxide scaffold with the divalent cation solution, the titanium dioxide scaffold may be immersed in the divalent cation solution for a period of time of e.g. 10 min to 2 hours, such as 1-2 hour, e.g. 1 hour. This may take place under agitation, e.g. via an orbital shaker at about 100 rpm/min. Alternatively, other means for providing the divalent cation solution may be used, e.g. such as by spraying the titanium dioxide scaffold with the solution. After providing the divalent cation solution to the titanium dioxide, the scaffold is optionally rinsed, e.g. in distilled water to remove excess divalent cation solution. Excess divalent cation salt solution may alternatively or in addition be removed by careful centrifugation of the titanium dioxide scaffold, such as at about 200-300×g, for a short time period, such as 0.5-2 min, e.g. 1 min. If a centrifugation step is applied, the optional rinsing preferably takes place after the centrifugation. Further, biologically active substances may be added to the divalent cation solution (e.g. in the same concentrations as when added to the polymer solution), although these are preferably added to the alginate solution. When the polymer is chitosan or PEG, gelation may also be effected as disclosed for effecting gelation of alginate.

When chitosan is used as the polymer, gelation (step c)) may be effected by a change in pH, or by crosslinking by ionic interactions. Chitosan is the deacetylated derivative of chitin, a natural component of shrimp and crab shells. It is a biocompatible, pH-dependent cationic polymer, which is soluble in water up to pH 6.2. Gelation of chitosan may e.g. be effected by a raise in pH to a basic pH, such as about pH 8 or more. The starting pH of the chitosan solution may be from 3 to less than 8, such as about 5.5. Basification of aqueous chitosan solutions above a pH of 8 leads to the formation of a hydrated gel-like precipitate. Phase separation ensues from the neutralization of chitosan amine groups and the consequent elimination of repulsive interchain electrostatic forces, which subsequently allow for extensive hydrogen bonding and hydrophobic interactions between chains. When gelation of chitosan is effected by the use of crosslinking by ionic interactions, a divalent cation salt is provided to the titanium dioxide scaffold obtained in step b) in a similar manner as is disclosed for alginate.

When poly(ethylene glycol) (PEG) is used as the polymer in step b), gelation may e.g. be effected by crosslinking by ionic interactions by providing a divalent cation salt solution to the titanium dioxide scaffold obtained in step b) in a similar manner as is disclosed for alginate. The gelation will be faster and create a more denser gel with higher divalent salt concentration. Condensation reactions between hydroxyl groups or amines with carboxylic acids or derivatives hereof are frequently applied for the synthesis of polymers to yield polyesters and polyamides, respectively, PEG. However, numerous other methods for effecting gelation of PEG are available and known to the person skilled in the art.

When a pluronic hydrogel is prepared such as by the use of poloxamer gelation may be effected by an increase in temperature. In this case, the starting temperature when the gelation is to be effected has to be 10° C. or less. The temperature is then raised to about 35-45° C., such as 37° C., which will cause a gelation of the polymer and the formation of a pluronic hydrogel.

When a hyaluronic acid based hydrogel is to be prepared, in step c) the titanium dioxide scaffold is immersed in a solution comprising a chemical crosslinker such as tetrathiol-derivatized polyethylene glycol (PEG). —SH4 (MW 10,000) in concentration range of about 0.01 to 10 g/L.

When a polyethylene oxide (PEO) hydrogel is to be formed, gelation in step c) may be effected by temperature-dependent polymerizing by an increase in temp from 20° C. to 37° C., or decrease the temperature form 50° C. to 37° C. Alternatively, the titanium dioxide scaffold obtained in step b) may be exposed to irradiation with light at a wavelength of 200-400 nm to effect gelation in step c) when a PEO hydrogel is to be formed.

Step d) may be performed for a time period of about 0.5 hours to several days. It may e.g. be performed overnight, e.g. for 0.5-24 hours, 5-10 hours or just 1 hour. Typically, this step is performed at room temperature.

The method for producing a hydrogel coated titanium dioxide scaffold disclosed herein provides a titanium dioxide scaffold provided with a hydrogel coating comprising a biologically active substance(s). This document is therefore also directed to the herein disclosed titanium dioxide scaffold comprising a hydrogel coating comprising a biologically active substance(s), obtainable or obtained by the above method.

When the above method is used for preparing the hydrogel coated titanium dioxide scaffold at least part of the outer surface of the scaffold will be provided with the hydrogel coating. However, as the titanium dioxide scaffold adopts a porous structure, by the above method, the polymer solution will also be allowed to penetrate the pores of the scaffold and the hydrogel coating consequently also form on the surface of at least part of the pores inside the scaffold. How deep into the scaffold pores the hydrogel coating will form, will of course depend on factors such as scaffold porosity (a larger porosity will ease the penetration of polymer and allow the coating to form deeper inside the scaffold), concentration of polymer and/or the method used for effecting gelation in step c), the centrifugation speed etc. However, the present method allows at least part of the surface (the walls) of at least the outer pores of the titanium dioxide scaffold to be coated with an hydrogel coating. Typically, the hydrogel coating is present throughout the scaffold structure, when a hydrogel coated titanium dioxide scaffold is analysed by scanning electron microscopy (SEM). By the above method, the hydrogel coating therefore does not only form on the outer surface of the titanium dioxide scaffold, but also in a varying degree on the surface of the pores inside the scaffold. Typically, the majority of the pore surfaces onto which the hydrogel coating is provided will be coated with the hydrogel coating.

Of course only part of the titanium dioxide scaffold may be provided with the polymer solution. Importantly, in order for the hydrogel coating to form, the part of the scaffold on which such hydrogel coating formation is desired must be subjected to both the polymer solution and the method for effecting gelation.

By the present method, it is possible to form a thin hydrogel coating on the titanium dioxide scaffold as the centrifugation in step b) allows a very thin layer of polymer solution to be deposited on the outer surface and also inside the pores of the titanium dioxide scaffold. Also, without wishing to be bound by theory, the hydrogel coating may be the result of the low density of the polymer solution used, which allows its penetration into the pores of the scaffold. The above method allows each hydrogel layer of the hydrogel coating to typically have a wet thickness of at least 1 μm, such as about 3 μm, on the surfaces it coats. However, by repeating method steps b) and c), a hydrogel coating consisting of two or more hydrogel layers may be built up. The above method may therefore be used to control the thickness of the hydrogel coating by repeating steps b) and c), such as for 2-100, 2-10, 2-6, 2-4, 3 or 4 times, until a hydrogel coating of the desired thickness is obtained.

Also, the above method allows a hydrogel coating having a more even thickness to form. Further, the hydrogel coating formed by this method is substantially non-porous, c.f. an alginate hydrogel prepared by simply mixing alginate and a divalent cation salt solution which has some porosity (see e.g. the gel prepared in Example 1 and depictured in FIG. 1). The reason for the substantial lack of porosity of the hydrogel coating when prepared on a titanium dioxide scaffold by the method disclosed above, is probably the thin coating of polymer solution formed on the titanium dioxide scaffold after centrifugation in step b).

Also, the above method allows the formation of a hydrogel coating comprising one or more hydrogel layers by repeating steps b) and c). If preferred, this also allows the formation of different hydrogel layers with different biologically active substance(s) and/or types of polymers in the different layers.

When the polymer used is PEG, chitosan or alginate, it is also possible to perform step c) before step b). However, in that case, a thin coating of hydrogel is not formed. Rather, in this case, the hydrogel coating fills up the majority of the pores inside the titanium dioxide scaffold. This may be particularly advantageous when cells, such as stem cells, are to be incorporated into the titanium dioxide scaffold, as this allows a large number of cells to be deposited inside the scaffold pores. When step c) is performed before step b) it may be superfluous to repeat steps c) and b) as most of the pores of the titanium dioxide scaffold will be filled up with hydrogel coating already after performing steps c) and b) once.

By performing the above method, a hydrogel coated titanium dioxide scaffold as disclosed herein is produced. The present document is therefore also directed to a hydrogel coated titanium dioxide scaffold as defined herein, obtainable or obtained by performing the above method.

Applications of the Hydrogel Coated Titanium Dioxide Scaffold

Hydrogels have been used for different applications in tissue engineering such as space filling agents, as delivery vehicles for bioactive molecules, and as three dimensional structures that organize cells and present stimuli to direct the formation of a desired tissue and the hydrogel coating disclosed in the present document may advantageously be used for any such purpose. The titanium dioxide scaffolds of the present document may also advantageously be used for cell seeding, before or after being coated with a hydrogel by a method disclosed herein.

The titanium dioxide scaffold comprising a hydrogel coating is typically used as a medical implant, either alone or comprised as a part of an implant. As is evident from other parts of this document, the titanium dioxide scaffold structure used allows tailoring of implant structures, specifically adapted to the implantation site and intended function of the implant. This document is therefore also directed to a titanium dioxide scaffold comprising a hydrogel coating for use as a medical implant. The hydrogel coated titanium dioxide scaffold comprises a porous structure which has a good biocompatibility and which may stimulate the growth of cells and attachment of the scaffold or the implant comprising the scaffold. The porous structure allows ingrowth of cells into the scaffold, which thereby allows for the regeneration of tissue. The large surface area of the also facilitates the growth of cells into the structure and thereby the attachment of the scaffold and regeneration of tissue. As the titanium dioxide scaffold in itself is made of a material that has a good biocompatibility, adverse reactions to the scaffold when implanted into a subject are reduced.

The titanium dioxide scaffold comprising a hydrogel coating may be implanted into a subject wherein cells will grow into the scaffold structure. It is also possible to seed and grow cells on the hydrogel coated titanium dioxide scaffold prior to implantation. The interconnected macroporous structure of the titanium dioxide scaffold is especially suitable for tissue engineering, and notably bone tissue engineering, an intriguing alternative to currently available bone repair therapies. In this regard, bone marrow-derived cell seeding of the titanium dioxide scaffold is performed using conventional methods, which are well known to those of skill in the art (see e.g. Maniatopoulos et al. 1988). Cells are seeded onto the hydrogel coated titanium dioxide scaffold and cultured under suitable growth conditions. The cultures are fed with media appropriate to establish the growth thereof. It is also possible to seed the titanium dioxide scaffold with cells, such as stem cells, such as mesenchymal stem cells, prior to providing the hydrogel coating to the scaffold (see Example 10 for an exemplary method to perform such cell seeding with an alginate hydrogel).

Hydrogels that are associated to have positive effect on bone formation and drug delivery in bone are e.g. chitosan, PEG, poloxamers such as pluronic, hyaluronic acid based hydrogels, polyethylene oxide (PEO) hydrogel and heparin sulfates.

Cells of various types can be grown throughout the hydrogel coated titanium dioxide scaffold. More precisely, cell types include hematopoietic or mesenchymal stem cells, and also include cells yielding cardiovascular, muscular, or any connective tissue. Cells may be of human or other animal origin. However, the hydrogel coated titanium dioxide scaffold is particularly suited for the growth of osteogenic cells, precursor bone cells, progenitor cells, stem cells, pluripotent cells, multi-potent cells, vascular (endothelial) cells, especially cells that elaborate bone matrix. For tissue engineering, the cells may be of any origin. The cells are advantageously of human origin. A method of growing cells in a hydrogel coated titanium dioxide scaffold allows seeded osteogenic cells, for example, to penetrate the titanium dioxide scaffold to elaborate bone matrix, during the in vitro stage, with pervasive distribution in the structure of the titanium dioxide scaffold. Osteogenic cell penetration and, as a result, bone matrix elaboration can be enhanced by mechanical, ultrasonic, electric field or electronic means.

The hydrogel coated titanium dioxide scaffold is useful whenever one is in need of a structure to act as a framework for growth of cells, such as for regeneration of a tissue. The hydrogel coated titanium dioxide scaffold is particularly useful for the regeneration of bone and cartilage structures. Examples of situations where the regeneration of such structures may be necessary include trauma, surgical removal of bone or teeth or in connection to cancer therapy.

Examples of structures in a subject which wholly or partially may be replaced include, but are not limited to, cranio-facial bones, including arcus zygomaticus, bones of the inner ear (in particular the malleus, stapes and incus, maxiliar and mandibular dentoalveolar ridge, walls and floor of eye sockets, walls and floor of sinuses, skull bones and defects in skull bones, socket of hip joint (Fossa acetabuli), e.g. in the case of hip joint dysplasias, complicated fractures of long bones including (but not restricted to) humerus, radius, ulna, femur, tibia and fibula, vertebrae, bones of the hands and feet, finger and toe bones, filling of extraction sockets (from tooth extractions), repair of periodontal defects and repair of periimplant defects. In addition the hydrogel coated titanium dioxide scaffold is useful for the filling of all types of bone defects resulting from (the removal of) tumors, cancer, infections, trauma, surgery, congenital malformations, hereditary conditions, metabolic diseases (e.g. osteoporosis and diabetes).

The hydrogel coated titanium dioxide scaffold prepared by the disclosed method or a medical implant comprising such a scaffold may be used for the regeneration, repair, substitution and/or restoration of tissue, such as bone. This document is therefore also directed to the hydrogel coated titanium dioxide scaffold or a medical implant comprising it for use for the regeneration, repair, substitution and/or restoration of tissue, such as bone.

The hydrogel coated titanium dioxide scaffold obtainable or obtained by the method of the present document may also be used for the preparation of a medical implant for the regeneration, repair, substitution and/or restoration of tissue, such as. The hydrogel coated titanium dioxide scaffold may also be used for the preparation of a medical implant for the regeneration, repair, substitution and/or restoration of tissue, such as bone.

The hydrogel coated titanium dioxide scaffold obtainable or obtained by the method of the present document or a medical implant comprising it may also be used in a method for the regeneration, repair, substitution and/or restoration of tissue comprising the implantation into a subject in need thereof of the scaffold or medical implant comprising such a hydrogel coated titanium dioxide scaffold.

Biologically Active Substances (Biomolecules)

As mentioned above, the hydrogel solution and/or the divalent cation solution may comprise one or more different kinds of biologically active substance(s). The biologically active substance(s) may therefore be incorporated into the hydrogel coating. The hydrogel coating may therefore act as a carrier for a biologically active substance and biologically active substances consequently delivered by the alginate coated titanium dioxide scaffold via the hydrogel coating. The hydrogel coating may comprise one kind of biologically active substance or a mixture of two or more biologically active substances. As mentioned above, when the hydrogel coating is prepared by repeating steps b) and c) of the method as disclosed elsewhere herein, the different layers may comprise different biologically active substances.

The biologically active substance may be any substance having a biological activity in the body, such as a synthetic or natural bioactive molecule, a natural or synthetic drug, and/or a living cell. Inorganic, biologically active ions may also be incorporated, such as calcium, chromium, fluoride, gold, iodine, potassium, magnesium, manganese, selenium, sulphur, stannum, sodium, zinc, strontium, nitrate, nitrite, phosphate, chloride, sulphate, carbonate, carboxyl or oxide.

The biologically active substance may also be a cell. Examples of living cells for incorporation in the hydrogel coating include, but are not limited to, mesenchymal stem cells, bone cells, pluripotent cells, bone precursors cells, vascular cells, precursors vascular cells, and/or stromal cells.

Examples of biologically active substances also include, but are not limited to, natural or recombinant bio-adhesives; natural or recombinant cell attachment factors; natural, recombinant or synthetic biopolymers; natural or recombinant blood proteins; natural or recombinant enzymes; natural or recombinant extracellular matrix proteins; natural or synthetic extracellular matrix biomolecules; natural or recombinant signal molecules, growth factors and hormones; natural, recombinant and synthetic peptides, synthetic peptide hormones; natural, recombinant or synthetic deoxyribonucleic acids; natural, recombinant or synthetic ribonucleotide acids; natural or recombinant receptors; enzyme inhibitors; drugs; biologically active anions and cations; vitamins; adenosine monophosphate (AMP), adenosine diphosphate (ADP) or adenosine triphosphate (ATP); marker biomolecules; amino acids; fatty acids; nucleotides (RNA and DNA bases), sugars, antimicrobial substances such as tetracyclines, and small biological organic molecules such as statins and/or bisphosphonates.

Peptides and proteins suitable for incorporation into the hydrogel coating in particular include peptides and proteins known to affect cell growth and/or osseointegration of implants. A number of natural peptides have been shown to induce mineral precipitation and may therefore suitably be incorporated in the hydrogel coating. Examples include collagen 1 and 2, amelogenin, ameloblastin, bone sialoprotein, enamelin, and ansocalcin. Deposition and growth of apatites into endoskeletal mineralized tissues is a process guided by polyproline-rich proteins. Polyproline repeats are a common characteristic of hard tissue extracellular matrix proteins, playing a role on compaction of protein matrix, conformational variability, the apatite crystal length and bond to protein domains frequently involved in signaling events. For example, enamel matrix derivative (EMD) is an extract of porcine fetal tooth material used to biomimetically stimulate the soft and hard growth. EMD has also been proven to have a diversity of other biological activities, such as inhibition of inflammation and infection. A commercial product comprising EMD is Straumann®Emdogain (Straumann A G, Peter Merian-Weg 12, CH 4052 Basel, Switzerland). EMD contains a large amount of amelogenin, which is a protein that suitably may be incorporated into the hydrogel matrix, as mentioned above.

Further examples of peptides suitable for incorporation in the hydrogel coating include peptides based on the consensus peptides disclosed in WO 2008/078167, which induce biomineralization.

Peptides P2 (SEQ ID NO 1), P5 (SEQ ID NO 2) and P6 (SEQ ID NO 3), used in the experimental section, are examples of peptides based on the consensus sequences of WO 2008/078167 which may suitably be incorporated in the hydrogel coating. Other examples of such a sequence are P1 (SEQ ID NO 4: PLV PSY PLV PSY PLV PSY PYP PLPP), P3 (SEQ ID NO 5: PLV PSQ PLV PSQ PLV PSQ PQP PLPP) and P4 (SEQ ID NO 6: PLV PCC PLV PCC PLV PCC PCP PLPP).

The diffusion rate of biologically active substances optionally incorporated in the hydrogel coating is affected by the molecular weight and size of the biologically active substances (defined by Stokes radii) compared to the pores of the hydrogel coating and depends on the chemical nature of the biologically active substance (interactions molecule-hydrogel, polarization, i.e. hydrophilic substances may diffuse very quickly while hydrophobic substances diffuse slowly through the hydrogel gel). A burst release profile of the biologically active substance during the first day or days after implantation of the hydrogel coated titanium dioxide scaffold in a subject may be found for a smaller biologically active substance, such as the peptides used in the experimental section of this document. By adjusting the pore size of the hydrogel coating (see above) and by taking properties of the biologically active substance into account (such as molecular weight, shape, polarity etc.), the release rate of an incorporated biologically active substance may be adjusted.

The biologically active substance may typically be a substance which promotes the integration of the titanium dioxide scaffold in a subject.

The concentration of the biologically active substance in the hydrogel is typically in the range of micrograms, although it may range from 1 ng-100 mg/ml, such as 50 ng/ml-50 mg/ml, 100 ng-50000 ng/ml. Of course the concentration of the biologically active substance in the hydrogel will depend on the specific substance, its intended function in a subject etc.

The Titanium Dioxide Scaffold

The titanium dioxide scaffold of the present document is a reticulated scaffold which may function as a structural support which allows tissue formation by creating a three dimensional space for cellular attachment and ingrowth. The titanium dioxide of the scaffold provides a scaffold which is biocompatible and which can be processed into different shapes to provide mechanical support and a framework for cellular growth. Thus, the titanium dioxide scaffold provides a suitable structure to be used in tissue engineering, such as for regeneration of bone.

The titanium dioxide scaffold suitable for use in the context of the present document is a scaffold basically formed of titanium dioxide, i.e. titanium dioxide is the main structural component of the titanium dioxide scaffold. The titanium dioxide scaffold should adopt an open porous structure.

The titanium dioxide scaffold typically is a macroporous scaffold comprising macropores and interconnections. Macropores of the titanium dioxide scaffold have a pore diameter in the range between approximately 10-3000 µm, such as 20-2000 µm, about 30-1500 µm or about 30-700 µm. It is important that the titanium dioxide scaffold allows for the ingrowth of larger structures such as blood vessels and trabecular bone, i.e. also comprises pores with a diameter of about 100 µm or more. It is important that at least some of the pores are interconnected and/or partially interconnected.

The pore diameter may affect the rate and extent of growth of cells into the titanium dioxide scaffold and therefore the constitution of the resulting tissue. The macroporous system typically occupies at least 50% volume of the titanium dioxide scaffold. The volume of the macro- and micropores in the titanium dioxide scaffolds may vary depending on the function of the titanium dioxide scaffold. If the aim with a treatment is to replace much bone structure and the titanium dioxide scaffold can be kept unloaded during the healing time, the titanium dioxide scaffold may be made with a macroporous system occupying up to 90% of the total scaffold volume.

The titanium dioxide scaffold typically has a total porosity of about 40-99%, such as 70-90%.

The fractal dimension strut of the titanium dioxide scaffold is typically about 2.0-3.0, such as about 2.2-2.3. The strut thickness affects the strength of the titanium dioxide scaffolds, the thicker the struts in the titanium dioxide scaffold are, the stronger the titanium dioxide scaffold is.

The titanium dioxide scaffold typically has an inner strut volume of about 0.001-3.0 µm$^3$, such as about 0.8-1.2 µm$^3$. A lower volume and a higher fractal number give a stronger scaffold.

It will be understood by those of skill in the art that the surface of the titanium dioxide scaffold has a structure on the microlevel and the nanolevel. This micro and nano structure may be modified due to the manufacturing conditions. The pore diameters on the microlevel are typically in the range of 1-10 µm. The pore diameters on the nanolevel typically are less than 1 µm.

A titanium dioxide scaffold structure in the present context typically has a combined micro and macro pore diameter of approximately 10-3000 µm, such as 20-2000 µm, 30-1500 µm or 30-700 µm. The pore diameter may also be above 40 µm, with interconnective pore of at least 20 µm.

The size and the shape of the titanium dioxide scaffold are decided depending on its intended use. The titanium dioxide scaffold size and shape may be adjusted either at the stage of production or by later modification of a ready scaffold. The titanium dioxide scaffolds may therefore easily be tailored for their specific use in a specific subject. Typically the size, shape etc. of the titanium dioxide scaffold is adjusted before being coated with a hydrogel coating.

Typically, the titanium dioxide scaffold may be produced by a method of dipping a polymer sponge structure in a titanium dioxide slurry (see e.g. the methods disclosed in WO08078164), allowing the slurry to solidify on the sponge and performing one or more sintering steps to remove the sponge and creating a strong scaffold structure. The titanium dioxide scaffold may therefore for example be a titanium dioxide scaffold disclosed in WO08078164. Such a method may include the steps of:

a) preparing a slurry of titanium dioxide, b) providing the slurry of step a) to a combustible porous structure, such as a porous polymer structure, such as a sponge structure c) allowing the slurry to solidify on the combustible porous structure d) removing the combustible porous structure from the solidified titanium dioxide slurry, wherein step d) may be performed by i) slow sintering of the combustible porous structure with the solidified metal oxide slurry to about 500° C. and holding this temperature for at least 30 minutes, ii) fast sintering to about minimum 1500° C. or to about 1750° C. at ca 3 K/min and holding this temperature for at least 10 hours, and iii) fast cooling to room temperature at least 3 K/min.

The invention will be further described in the following examples, which do not limit the scope of the invention described in the claims.

EXPERIMENTAL SECTION

Example 1

Preparation of Alginate Hydrogel with and without Biologically Active Substance

TABLE 1

Amino acid sequence of synthetic proline-rich peptides.

| Peptide | Sequence (N-terminus to C-terminus) | Polar AA | Hydrophobic AA |
|---|---|---|---|
| P2 (SEQ ID NO 1) | PLVPSQPLVPSQPLVPSQPQPPLPP | 7 (S, Q) | 18 (P, L, V) |
| P5 (SEQ ID NO 2) | PLVPSSPLVPCCPLVPCCPSPPLPP | 3 (S) | 22 (P, L, V, C) |
| P6 (SEQ ID NO 3) | PHQPMQPQPPVHPMQPLPPQPPLPP | 7 (H, Q) | 18 (P, M, V, L) |

Amino acid (AA); peptide 2 (P2); peptide 5 (P5); peptide 6 (P6); S = Ser; P = Pro; L = Leu; V = Val; Q = Gln; M = Met; H = His; C = Cys.

1. Material and Methods

1.1. Preparation of Peptides and Enamel Matrix Derivative

Enamel matrix derivative (EMD) was kindly supplied by Straumann GmbH (Basel, Switzerland). EMD was dissolved to 10 mg/ml in 0.1% acetic acid in phosphate-buffered saline (PBS) (PAA Laboratories GmbH, Pasching, Austria). Three synthetic peptides (Table 1) were designed as described in detail in previous studies (Rubert M et al., 2011)

Peptides were purchased from Eurogentec (Seraing, Belgium). The synthetic peptides were dissolved to 5 or 10 mg/ml (in the case of peptide 2 FITC-labeled) in 0.1% acetic acid in PBS. Aliquots to avoid repeated freeze-thaw cycles were prepared and stored at −20° C. until use.

1.2. Preparation of Alginate Hydrogels

Sodium alginate (Pronova UP LVG®)—a low viscosity alginate where minimum 60% of monomers are guluronate—was purchased from NovaMatrix (FMC BioPolymer AS, Norway). The sodium alginate was used without further purification. Two percent (w/v) sodium alginate was prepared in PBS and stirred at 180 rpm at room temperature overnight to get a homogenous alginate hydrogel. The alginate solution was mixed with synthetic peptides or EMD at final concentration of 50 μg/ml. The solution of alginate containing synthetic peptides/EMD was then distributed into 24-well culture plate and sprayed with 300 mM $CaCl_2$ by means of an aerograph paint atomizer (Precisso®, Madrid, Spain). After 1-2 h of Incubation at room temperature, alginate hydrogel was completely gelled.

1.3. Characterization of Alginate Hydrogel Morphology by Scanning Electron Microscopy Morphology of control 2% alginate hydrogels and 2% alginate hydrogels containing synthetic peptide 2 (50 μg/ml) were observed using scanning electron microscope (SEM, Hitachi S-3400N, Hitachi High-Technologies Europe GmbH, Krefeld, Germany). Microstructure of alginate hydrogels (nonlyophilized and lyophilized) was observed. For the alginate hydrogel lyophilization, samples were frozen at −80° C. followed by lyophilization at −35° C. Samples were then frozen in $N_2$ to allow an accurated cut into cross sections using a sharp scalpel. Structure of alginate hydrogels were observed at ×25 and ×100 of magnification using 10 kV and 40 Pa. Environmental secondary electron detector (ESED) was used for images at ×25 magnification and backscattered electron detector (BSED) was used for images at ×100 magnification. The diameter of each pore was measured using the software from the SEM, Hitachi S-3400N.

1.4. Peptide Release Profile

To study the peptide release profile, P2 was labeled with FITC. The release of peptide contained into the 2% alginate hydrogel (50 μg/ml) was quantified by fluorescence spectroscopy. First, alginate hydrogels were washed with culture media to remove the excess of $CaCl_2$. Then, 750 μl of cell culture media were added onto peptide loaded alginate hydrogel. The samples were incubated at 37° C. and 5% $CO_2$ for 21 days and cell culture media was changed twice a week. At prefixed time points (24 h, 4 d, 7 d, 11 d, 14 d, 18 d and 21 d), supernatants were collected and analyzed by fluorescence spectroscopy (λ ex 490 nm and λ em 525 nm) to determine the amount of peptide released to the media. The amount of peptide released during the washing step was also measured. The experiment was performed three times, and each sample analyzed in triplicate.

Relative fluorescence units were correlated with the amount of peptide released using a linear standard curve for each time point.

1.5. Cell Culture of MC3T3-E1

The mouse osteoblastic cell line MC3T3-E1 (DSMZ, Braunschweig, Germany) was maintained as previously described (Tiainen H et al., 2011). Before seeding, 24-well culture plates containing crosslinked alginate hydrogels were washed with 750 μl of culture media to remove the excess of $CaCl_2$. After evaluation of the efficiency of cell adhesion on 2% alginate gel using different cell densities, for the final experiments, cells were seeded at a density of 100 000 cells/well. Media was refreshed twice a week. Culture media was collected 24 h after seeding to study cell viability. Cells were harvested at days 14 and 21 to analyze gene expression of adhesion and osteogenic-related markers using real-time RT-PCR. Cultures were routinely observed using light microscopy (Leica DMIRB, Leica Microsystems Wetzlar GmbH, Germany).

1.6. Cell Adhesion to 2% Alginate Gel

Adhesion of cells onto the alginate hydrogel after one and five days post-seeding was evaluated in order to determine the best seeding density for the experiments. Densities from $30×10^4$ to $200×10^4$ cells/well were tested. Cells that were adhered onto the alginate hydrogel were lysed by a freeze-thaw method in deionized distilled water. Cell lysates were used for determination of DNA quantity using Hoechst 33 258 fluorescence assay. Samples were mixed with 20 μg/ml of Hoechst 33 258 fluorescence stain (Sigma, St. Quentin Fallavier, France) in TNE buffer, and the intensity of fluorescence was measured at excitation and emission wavelengths of 356/465 nm using a multifunction microplate reader (Cary Eclipse fluorescence spectrophotometer, Agilent Technologies, Santa Clara, USA). Relative fluorescence units were correlated with the cell number using a linear standard curve.

MC3T3-E1 cells adhered onto the alginate hydrogels after one and five days of culture were visualized by confocal microscopy (Leica TCS SPE Microsystems Wetzlar GmbH, Wetlzar, Germany). Briefly, cells seeded onto the alginate hydrogels were fixed with 4% formaldehyde in PBS at 4° C. for 10 min. For staining, cells were permeabilized in 0.2% triton and material autofluorescence was blocked with 3% BSA in PBS. The cytoskeleton of the cells was stained using 5 μg/ml FITC phalloidin (Sigma, St. Quentin Fallavier, France) and the nuclei with DAPI (Sigma, Schnelldorf, Germany). Further, the cell adhesion and attachment of $100 \times 10^3$ cells initially seeded on 2% alginate hydrogels was observed after cell fixation with 4% formaldehyde in PBS at 4° C. for 10 min followed by visualization using the SEM and ESED at 10 kV, ×200 and 40 Pa.

1.7. Cell Viability

The LDH activity determined in the culture media after 24 h was taken as an indicator of membrane leakage or cell lysis. The activity of the cytosolic enzyme was estimated as previously described (Rupert M at al., 2011).

TABLE 2

Sequence of osteoblast markers related genes.

| Gene | Primer sequence | |
|---|---|---|
| 18S | S 5'-GTAACCCGTTGAACCCCATT-3' | (SEQ ID NO 7) |
| | A 5'-CCATCCAATCGGTAGTAGCG-3' | (SEQ ID NO 8) |
| GAPDH | S 5'-ACCCAGAAGACTGTG-GATGG-3' | (SEQ ID NO 9) |
| | A 5'-CACATTGGGGGTAGGAACAC-3' | (SEQ ID NO 10) |
| Itga8 | S 5'-TCGCCTGGGAGGAGGCGAAA-3' | (SEQ ID NO 11) |
| | A 5'-TCTTAACCGCTGTGCTCCCCG-3' | (SEQ ID NO 12) |
| Itgb1 | S 5' AGCAGGCGTGGTTGCTGGAA-3' | (SEQ ID NO 13) |
| | A 5'-TTTCACCCGTGTCCCACTTGGC-3' (SEQ ID NO 14) | |
| Itgb3 | S 5'-AGGGGAGATGTGTTCCGGCCA-3' | (SEQ ID NO 15) |
| | A 5'-ACACACAGCTGCCGCACTCG-3' | (SEQ ID NO 16) |
| Fn1 | S 5'-GCTGCCAGGAGACAGCCGTG-3' | (SEQ ID NO 17) |
| | A 5'-GTCTTGCCGCCCTTCGGTGG-3' | (SEQ ID NO 18) |
| Bmp2 | S 5'-GCTCCACAAACGAGAAAAG-C-3' | (SEQ ID NO 19) |
| | A 5'-AGCAAGGGGAAAAG-GACACT-3' | (SEQ ID NO 20) |
| Coll-I | S 5'-AGAGC-ATGACCGATGGATTC-3' | (SEQ ID NO 21) |
| | A 5'-CCTTCTTGAGGTTGCCAGTC-3' | (SEQ ID NO 22) |
| Bsp | S 5'-GAAAATGGAGACGGCGATAG-3' | (SEQ ID NO 23) |
| | A 5'-ACCCGAGAGTGTGGAAAGTG-3' | (SEQ ID NO 24) |
| Alp | S 5'-AACCCAGACACAAGCATT-CC-3' | (SEQ ID NO 25) |
| | A 5'-GAGAGCGAAGGGTCAGTCAG-3' | (SEQ ID NO 26) |
| Oc | S 5'-CCGGGAGCAGTGTGAGCTTA-3' | (SEQ ID NO 27) |
| | A 5'-TAGATGCGTTTGTAGGCGGTC-3' | (SEQ ID NO 28) |
| Opn | S 5'-TCTGCGGCAGGCATTCTCGG-3' | (SEQ ID NO 29) |
| | A 5'-GTCACTTTCACCGGGAGGAGGA-3' (SEQ ID NO 30) | |

1.8. Total RNA Isolation and Gene Expression of Osteoblast Markers by Real-Time RT-PCR The effect of synthetic peptides and EMD loaded into the alginate hydrogels on gene expression was studied after 14 and 21 days of treatment on pre-osteoblast MC3T3-E1 cells.

Total RNA was isolated using Tripure® (Roche Diagnostics, Mannheim, Germany), according to the manufacturer's protocol. Total RNA was quantified at 260 nm using a Nanodrop spectrophotometer (NanoDrop Technologies, Wilmington, Del., USA).

The same amount of RNA (350 ng) was reverse transcribed to cDNA using high capacity RNA-to-cDNA kit (Applied Biosystems, Foster City, Calif.), according to the protocol of the supplier. Aliquots of each cDNA were frozen (−20° C.) until the PCR reactions were carried out.

Real-time PCR was performed in the Lightcycler 480® (Roche Diagnostics, Mannheim, Germany) using SYBR green detection. Real-time PCR was done for two reference genes (18SrRNA and glyceraldehyde-3-phosphate dehydrogenase (GAPDH)) and ten target genes (integrin alpha 8 (Itga8), integrin beta1 (Itgb1), integrin beta 3 (Itgb3), fibronectin 1 (Fn11), bone morphogenetic protein 2 (Bmp2), collagen type I (Coll-I), bone sialoprotein (Bsp), alkaline phosphatase (Alp), osteocalcin (Oc) and osteopontin (Opn)).

The primer sequences are detailed in Table 2. Reaction conditions and relative quantification have been done as previously described (Tiainen H et al., 2011).

1.9. Statistical Analyses

All data are presented as mean values ±SEM. Differences between groups were assessed by Mann-Whitney test or by Student t-test depending on their normal distribution. To measure the correlation among different variables, Pearson correlation analysis was used. The SPSS® program for Windows (Chicago, Ill.) version 17.0 was used. Results were considered statistically significant at the p-values ≤0.05.

Results

Alginate Microstructure

FIG. 1 shows the microstructure of a cross section from a lyophilized 2% alginate hydrogel (FIGS. 1 A) and B)) and 2% alginate hydrogel containing synthetic peptide (FIGS. 1C) and D)). As seen in the SEM images, although alginate hydrogel containing synthetic peptide showed a more irregular structure than 2% alginate hydrogel, a porous and interconnected structure was observed in all the gels analyzed. Both cross-linked hydrogels presented a porous and Interconnected structure with a pore diameter of 42.9±3.5 μm and 44.7±4.1 μm, for 2% alginate hydrogel without or with synthetic peptide respectively.

Peptide Delivery from 2% Alginate Hydrogel

Figure 2:
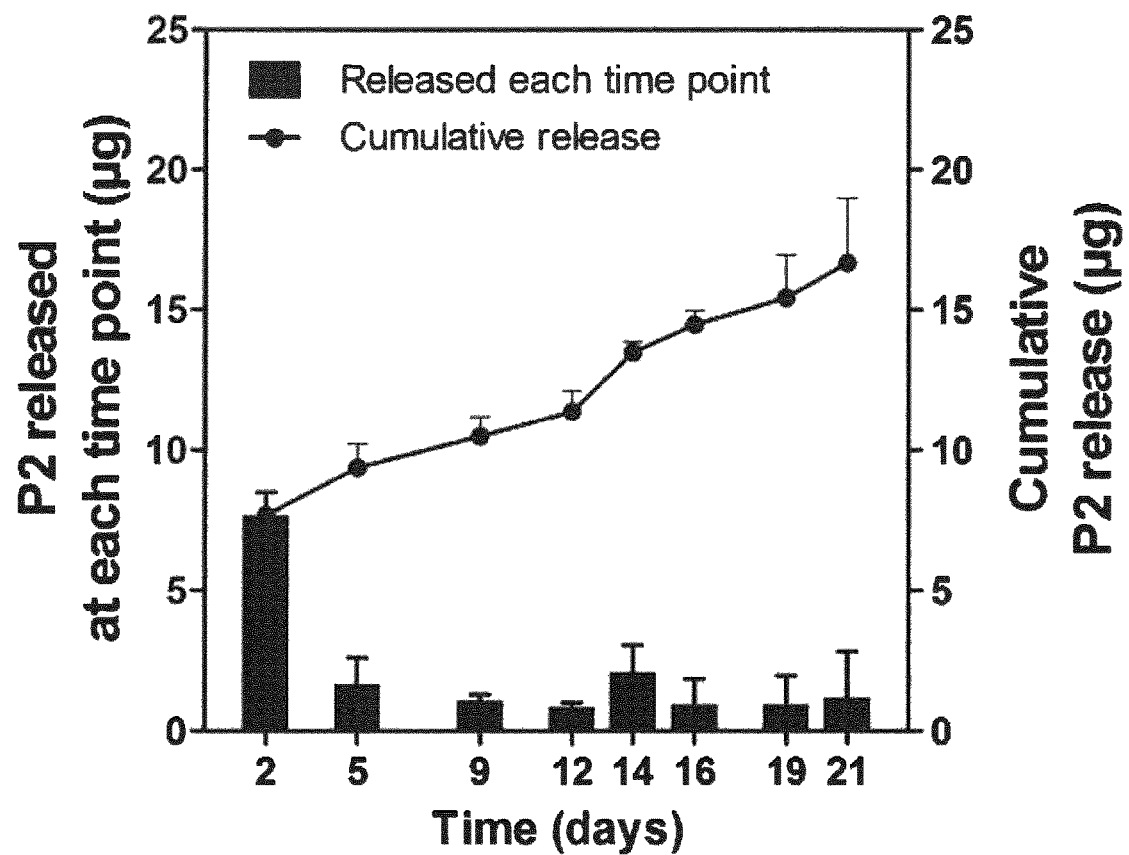
FIG. 2. Release profile of peptide 2 labeled with FITC after 21 days of incubation at 37° C. Bar graph show the amount of peptide released after each time point. Line graph represents cumulative amount of peptide released up to 21 days. Values represent mean ±SEM.

Peptide release profile from 2% alginate hydrogels is depicted in FIG. 2. A burst release of the peptide during the first 24 h of incubation was observed (54.67%). Further, as seen in the cumulative release profile, a 25.8% of peptide was slowly released up to 11 days, followed by a sustained release over time up to 21 days. At the end of the experiment (after 21 days) a 5.6% of the total peptide theoretically contained into the alginate hydrogel had not been released. It should be noted that a 12.7% of the loaded peptide was released during the washing step of the alginate hydrogels with culture media to remove the excess of $CaCl_2$.

Cell Adhesion and Proliferation

Figure 3A:
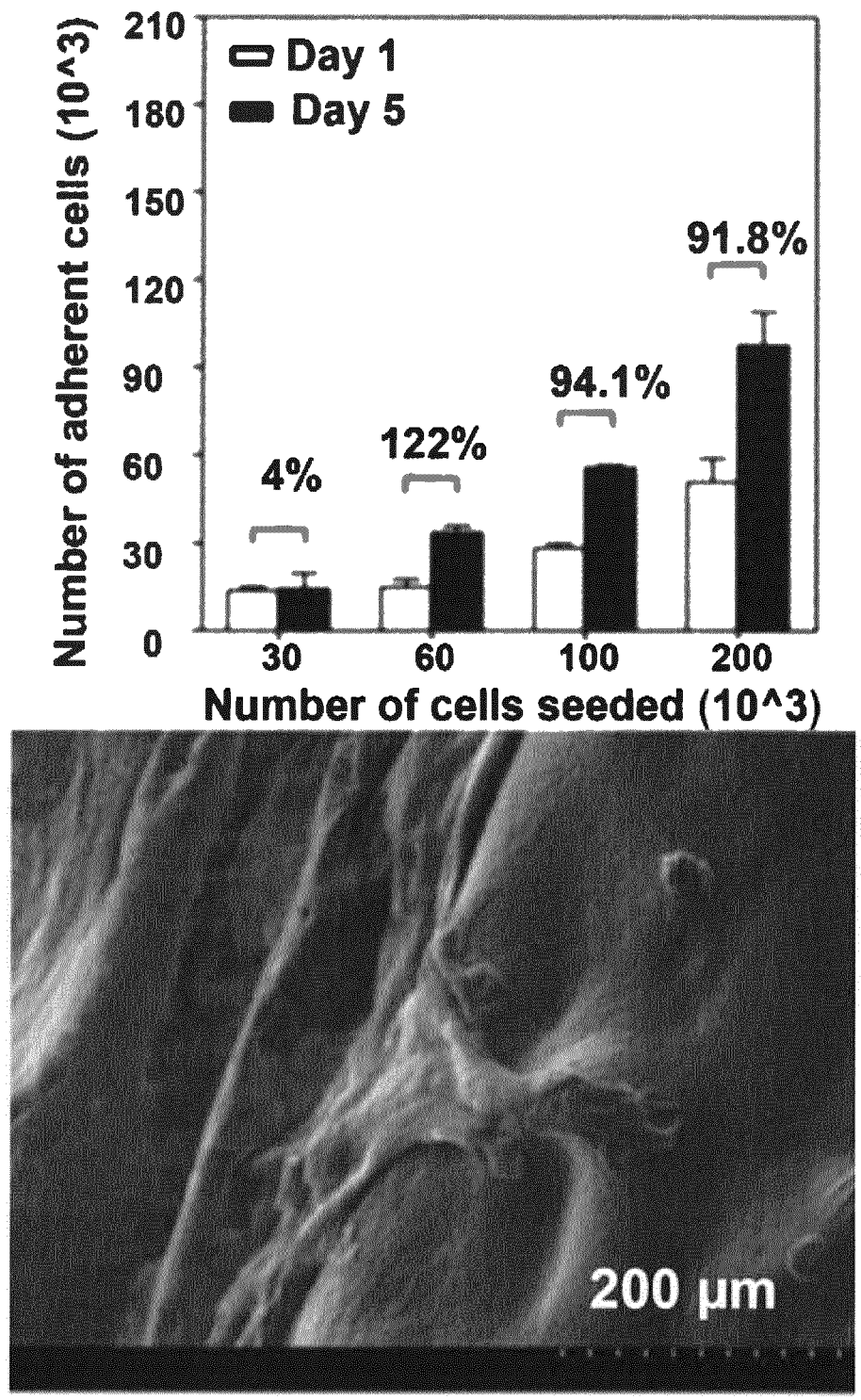
FIG. 3. A. Top: number of adherent cells when seeding different amounts of cells ($30\times10^3$, $60\times10^3$, $100\times10^3$ and $200\times10^3$ cells/well) after 1 and 5 days of culture. Values represent the mean ±SEM. Bottom: representative picture of osteoblast cells adhered on 2% alginate hydrogels when seeding $100\times10^3$ cells/well obtained by SEM at ×200 of magnification. B. Osteoblast attachment on 2% alginate coating. Representative pictures obtained by confocal microscopy of adherent cells when seeding $30\times10^3$ (A and B), $60\times10^3$ (C and D), $100\times10^3$ (E and F) and $200\times10^3$ (G and H) cells/well after 1 (A, C, E, G) and 5 (B, D, F, H) days of culture. Cell nuclei are presented in white (DAPI staining) (Left column) and actin filaments are presented in white (phalloidin-FITC) (right column). The bar scale represents 150 µm.
Figure 3B:
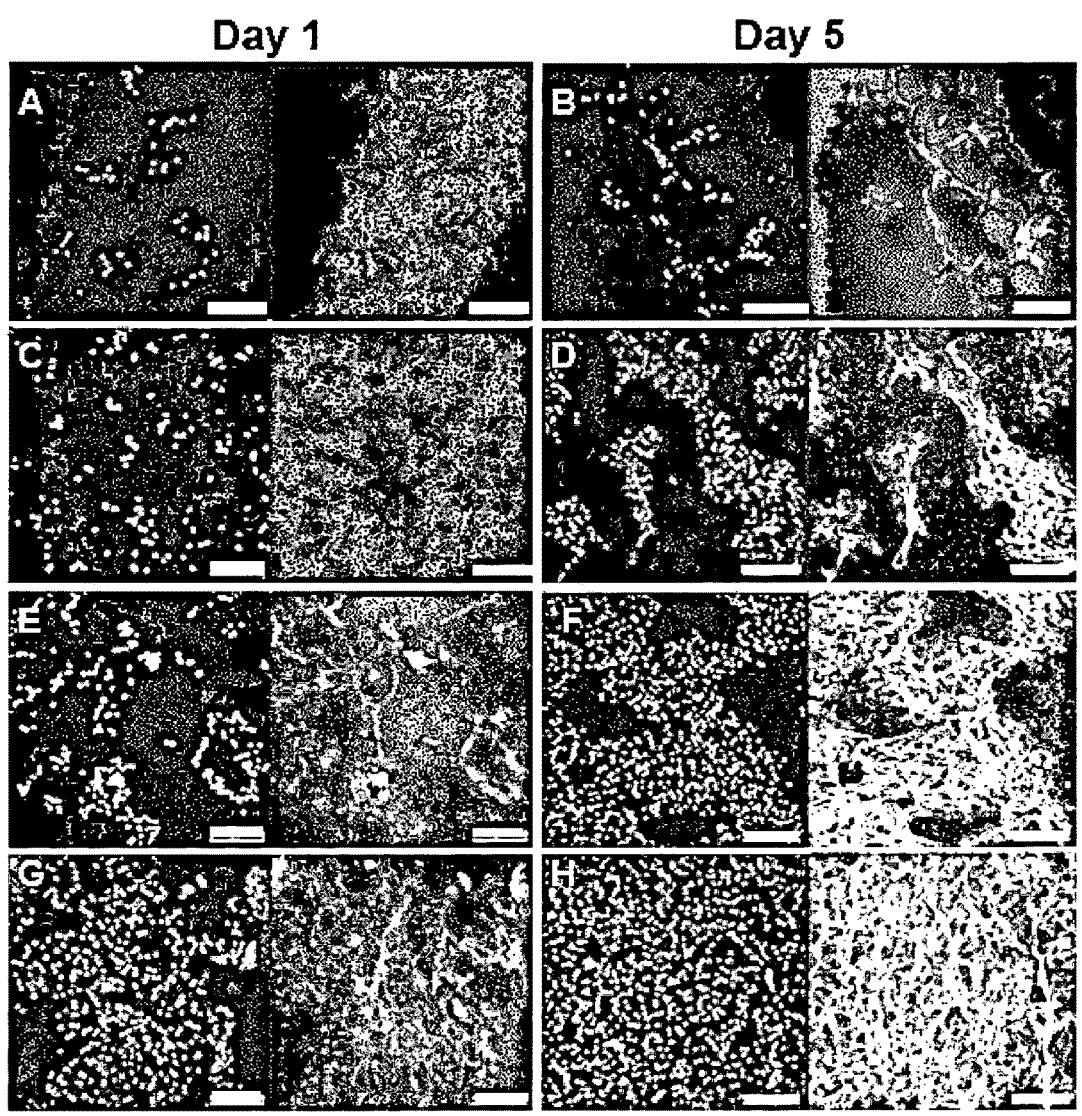
Figure 4:
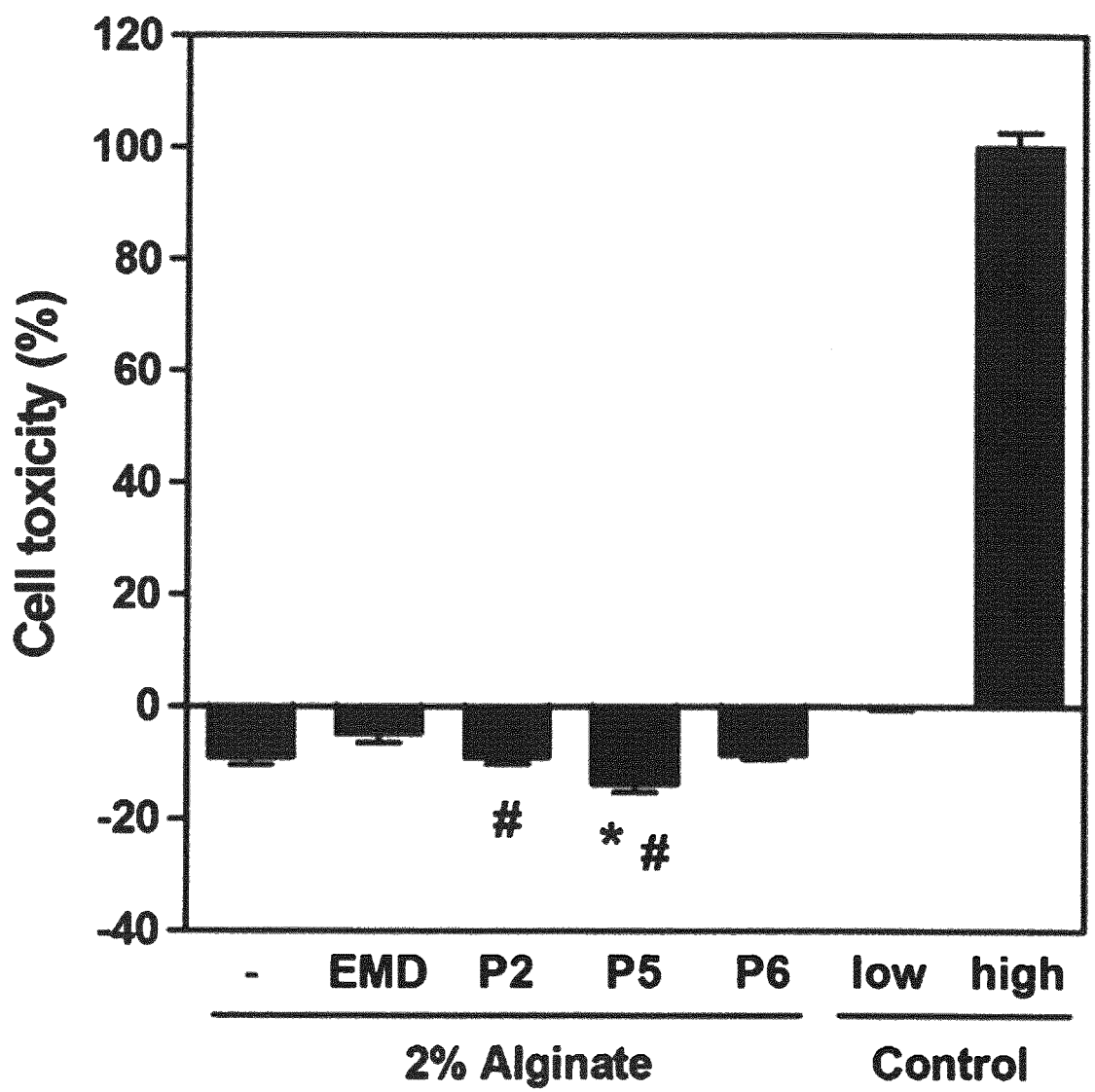
FIG. 4. LDH activity measured from culture media collected 24 h after seeding MC3T3-E1 cells onto alginate hydrogels without peptide (−) or alginate hydrogels containing 50 µg/ml of either Emdogain (EMD) or synthetic peptides (P2, P5 and P6). High control (100%) was cell culture media from cells seeded on tissue culture plastic and incubated with 1% Triton X-100. Low control (0%) was cell culture media from cells seeded on tissue culture plastic and incubated with 0.1% acetic acid-PBS. The percentage of LDH activity was calculated using the following equation: cytotoxicity (%)=(exp.value−low control)/(high control−low control)·100. Values represent the mean ±SEM. Differences between groups were assessed by Mann-Withney test *p<0.05 versus control alginate hydrogel (−), #p<0.05 versus alginate hydrogel containing EMD.

A low cell adhesion rate onto the alginate hydrogels was observed, since more than half of the seeded cells did not adhere to the gel one day after plating. Nevertheless, cells attached to the alginate hydrogel and proliferated over the cell culture (FIG. 3). Further, cells were visualized by confocal microscopy in order to verify the ability of osteoblasts to attach and spread on alginate hydrogels surfaces. Confocal images show an increase in the number of nuclei accompanied by an increase in actin staining as much number of cells seeded and increasing from day 1 to day 5 (FIGS. 3A)-H)). Moreover, the cell filopodia of osteoblasts cultured on the alginate hydrogel were appreciated by SEM Effect of Alginate Hydrogel Loaded with Synthetic Peptides on Cell Viability No toxic effects were found in cells cultured on alginate hydrogels containing synthetic peptides, either after 24 h (FIG. 4) or after long-term period (data not shown). P2 significantly increased cell viability after 24 h compared to EMD, while P5 showed significantly lower toxic effects compared to EMD and to untreated alginate gel.

Effect of Alginate Hydrogel Loaded with Synthetic Peptides on Gene Expression of Cell Adhesion Markers Expression of Itga8 was increased in cells treated with P5 when compared to control after 21 days of culture (FIG.

Figure 5A:
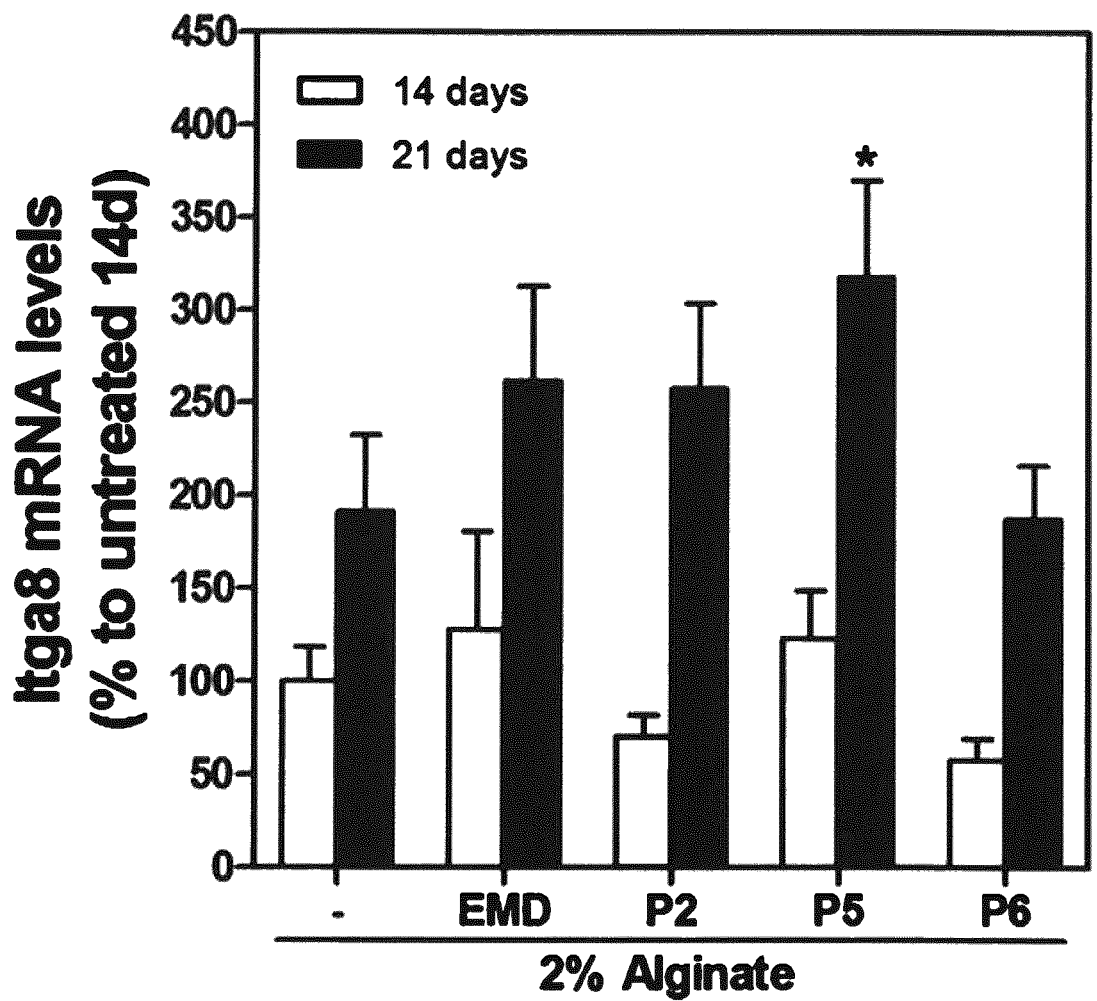
FIG. 5A-D. Expression of cell adhesion related genes after culture of MC3T3-E1 cells onto 2% of alginate hydrogels without peptide (−, control group), containing synthetic peptides or EMD (50 µg/ml) for 14 and 21 days. Data represent relative mRNA levels of target genes normalized with reference genes, expressed as a percentage of control alginate hydrogel at 14 days of culture, which was set to 100%. Values represent the mean ±SEM. Differences between groups were assessed by Student t-test; (*) p≤0.05 versus control alginate hydrogel (−), (#) p≤0.05 versus EMD.
Figure 5B:
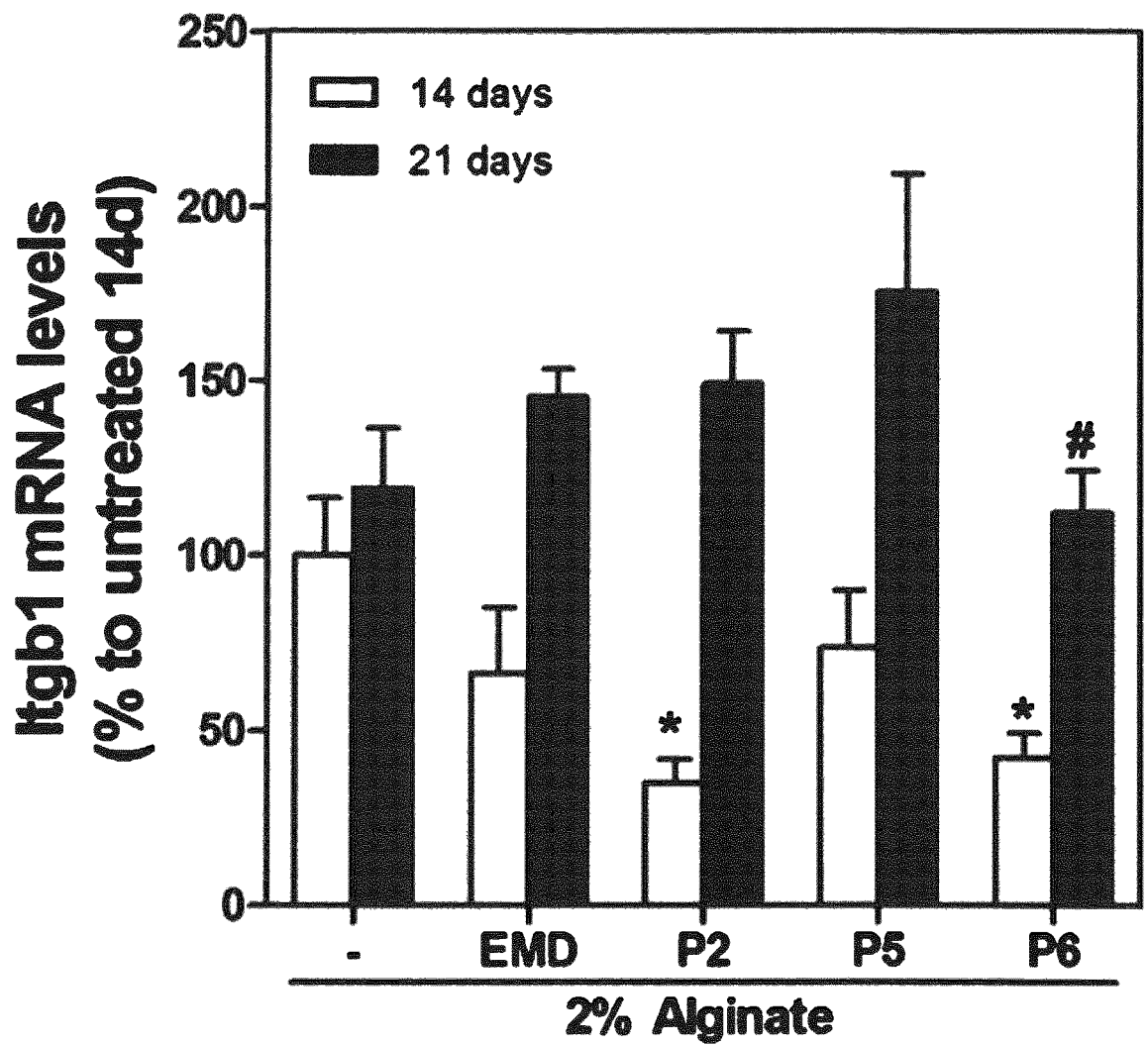
Figure 5C:
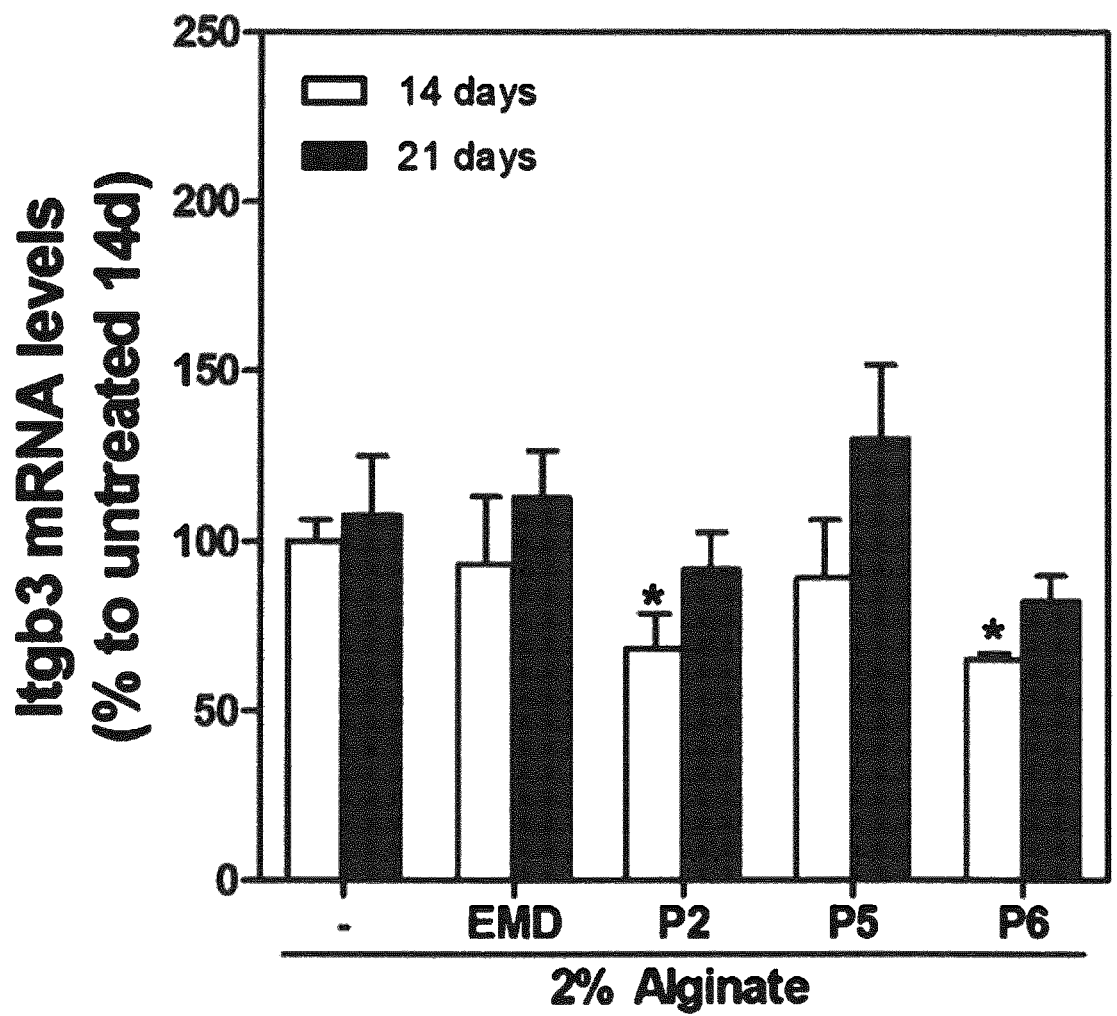
Figure 5D:
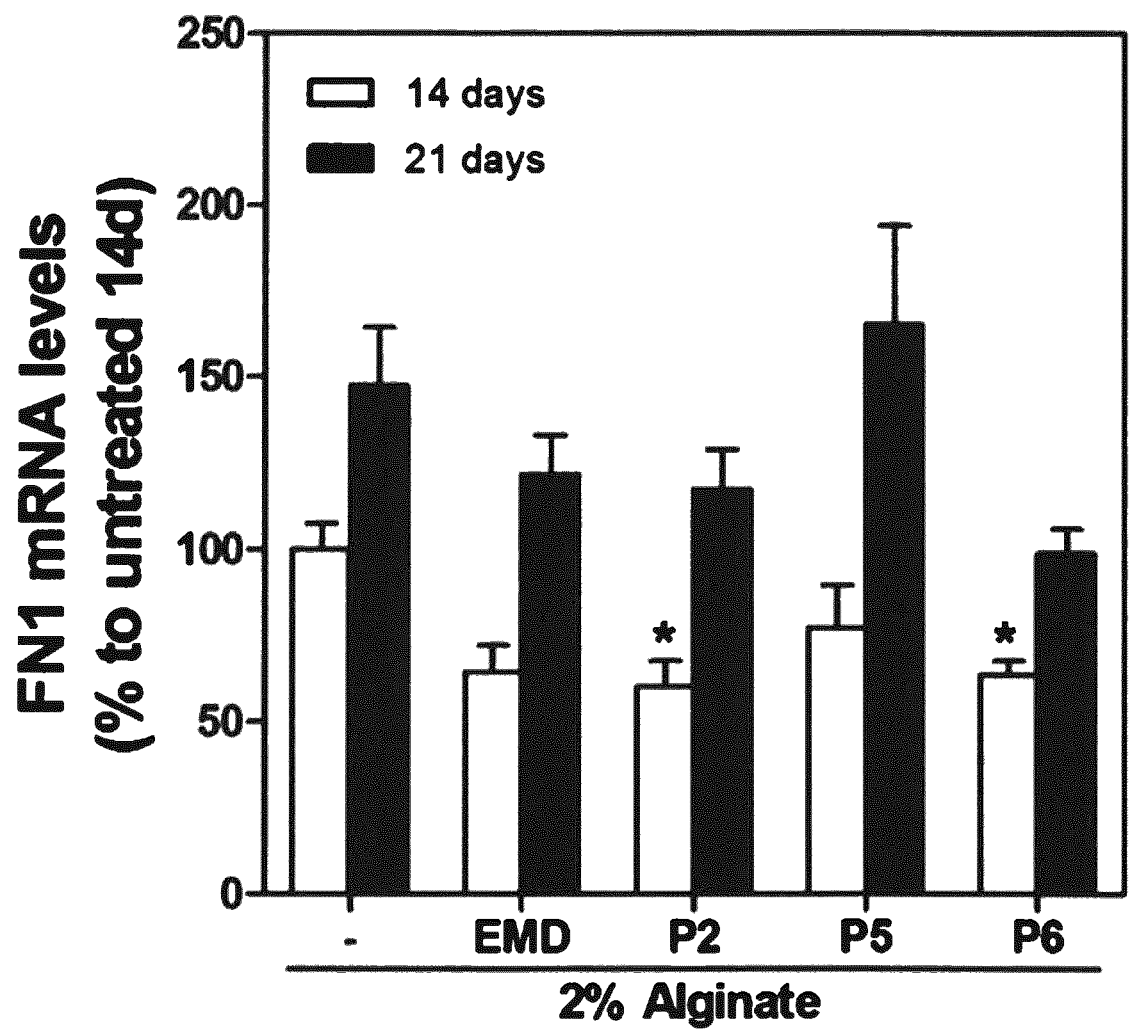

5A)). Itgb1 mRNA levels significantly decreased after treatment with P2 and P6 for 14 days compared to control. After 21 days, cells treated with P6 reduced significantly Itgb1 mRNA levels compared to EMD (FIG. 5B)). Itgb3 and Fn1 decreased significantly after 14 days of treatment with P2 and P6 compared to control (FIGS. 5C) and D)), and no differences were observed after 21 days.

Figure 6A:
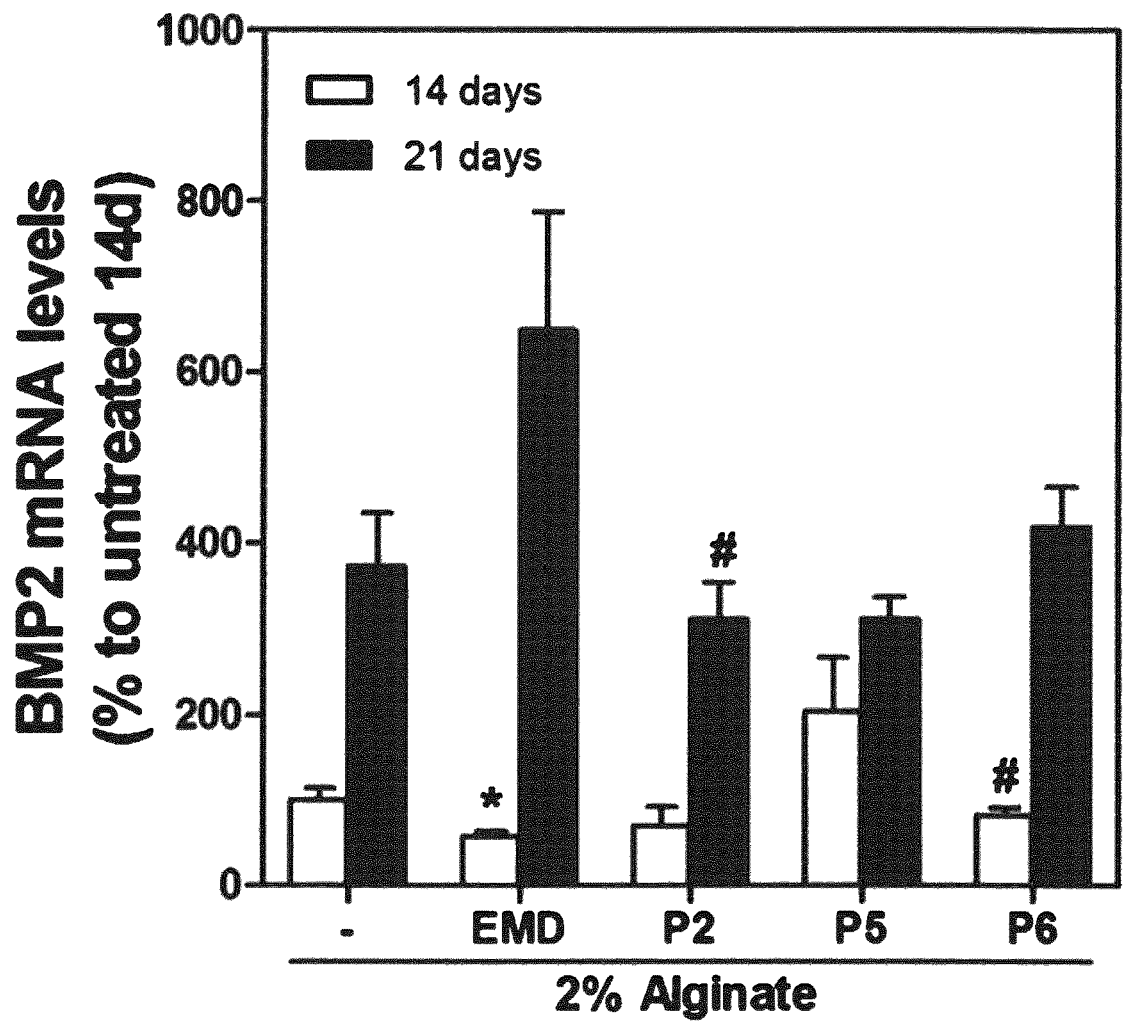
FIG. 6A-F. Expression of osteoblast differentiation related genes after culture of MC3T3-E1 cells onto 2% of alginate gels without peptide (−, control group), containing synthetic peptides or EMD (50 µg/ml) for 14 and 21 days. Data represent relative mRNA levels of target genes normalized with reference genes, expressed as a percentage of control alginate hydrogel at 14 days of culture, which was set to 100%. Values represent the mean ±SEM. Differences between groups were assessed by Student t-test; (*) p≤0.05 versus control alginate hydrogel (−), (#) p≤0.05 versus EMD.

Effect of Alginate Hydrogel Loaded with Synthetic Peptides on Gene Expression of Osteoblast Markers Bmp2 relative mRNA levels increased significantly after 14 days of treatment with P6, while decreased after 21 days of treatment with P2 compared to EMD. Though EMD treatment induced a significant decrease on Bmp2 mRNA levels after 14 days of cell culture compared to control, an increase on Bmp2 mRNA levels was found after 21 days, although differences did not reach statistical significance (FIG. 6A)).

Figure 6B:
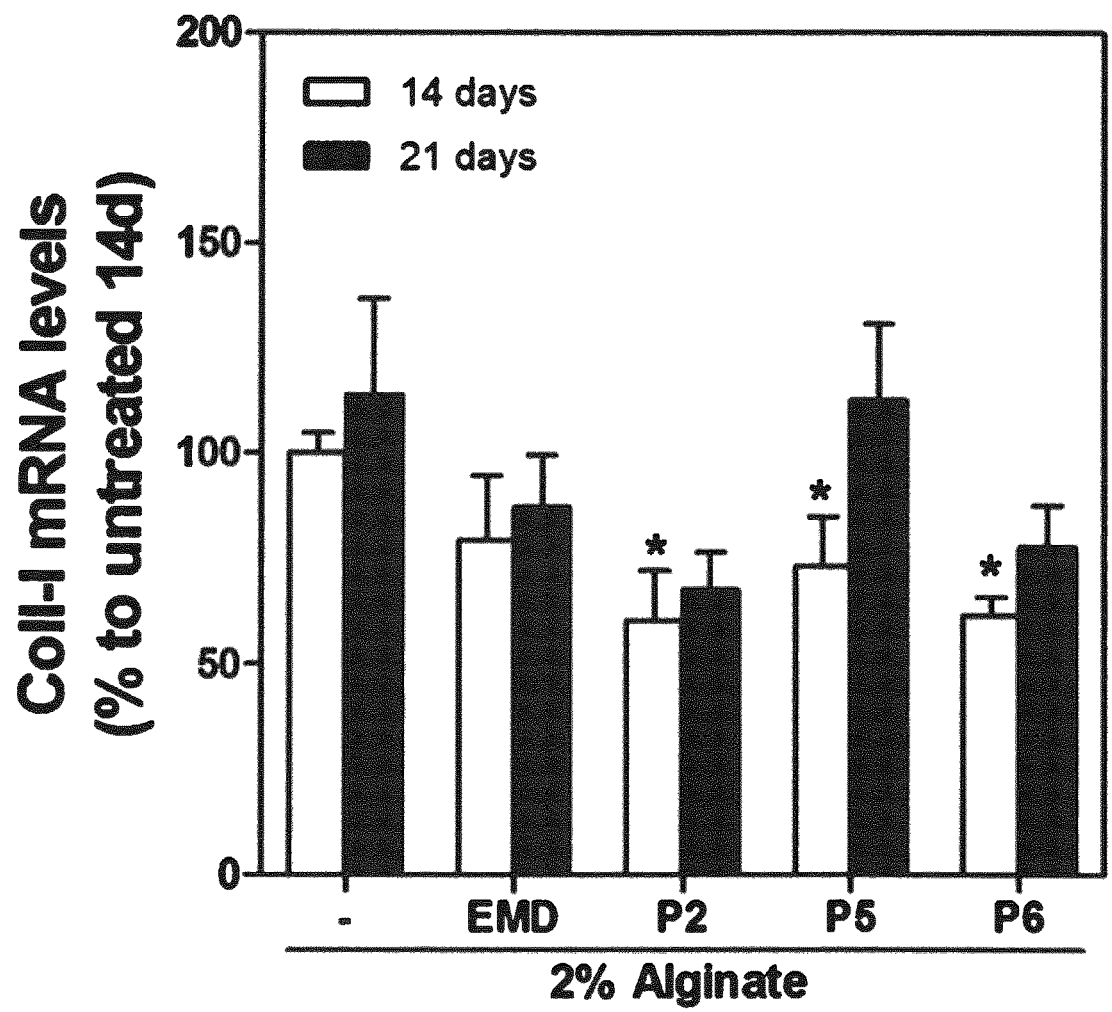
Figure 6C:
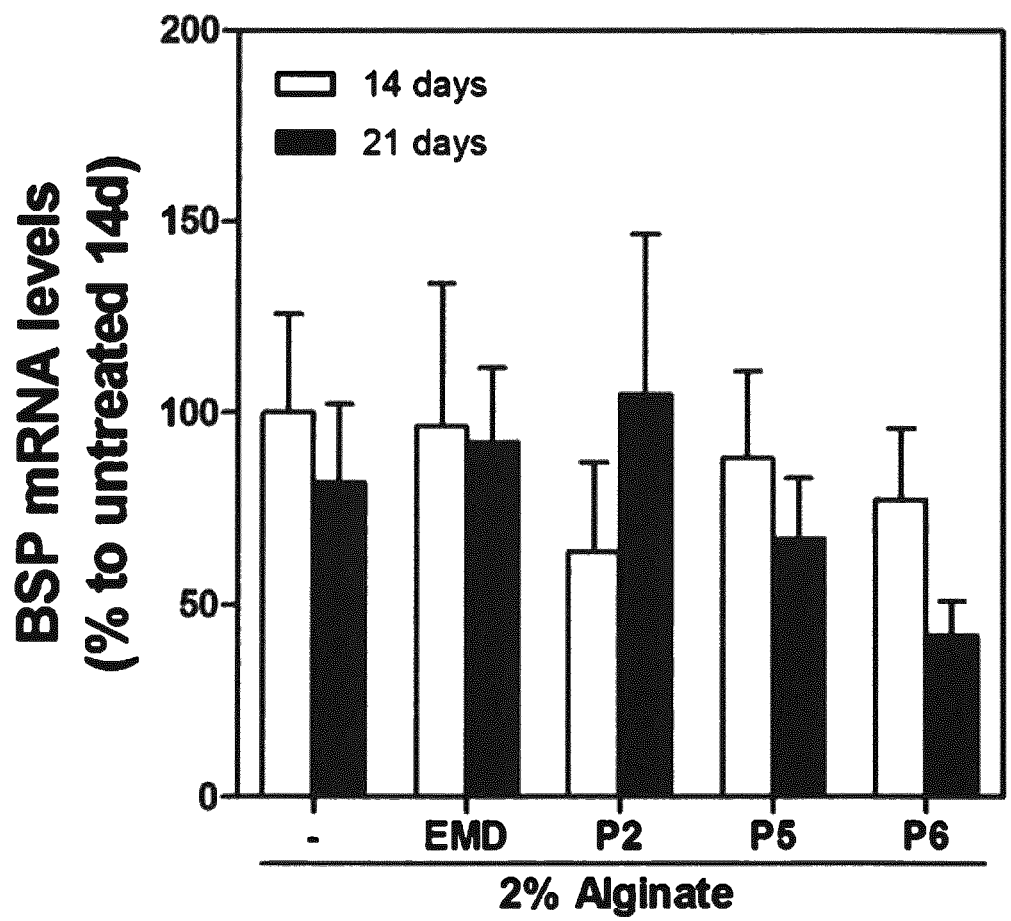
Figure 6D:
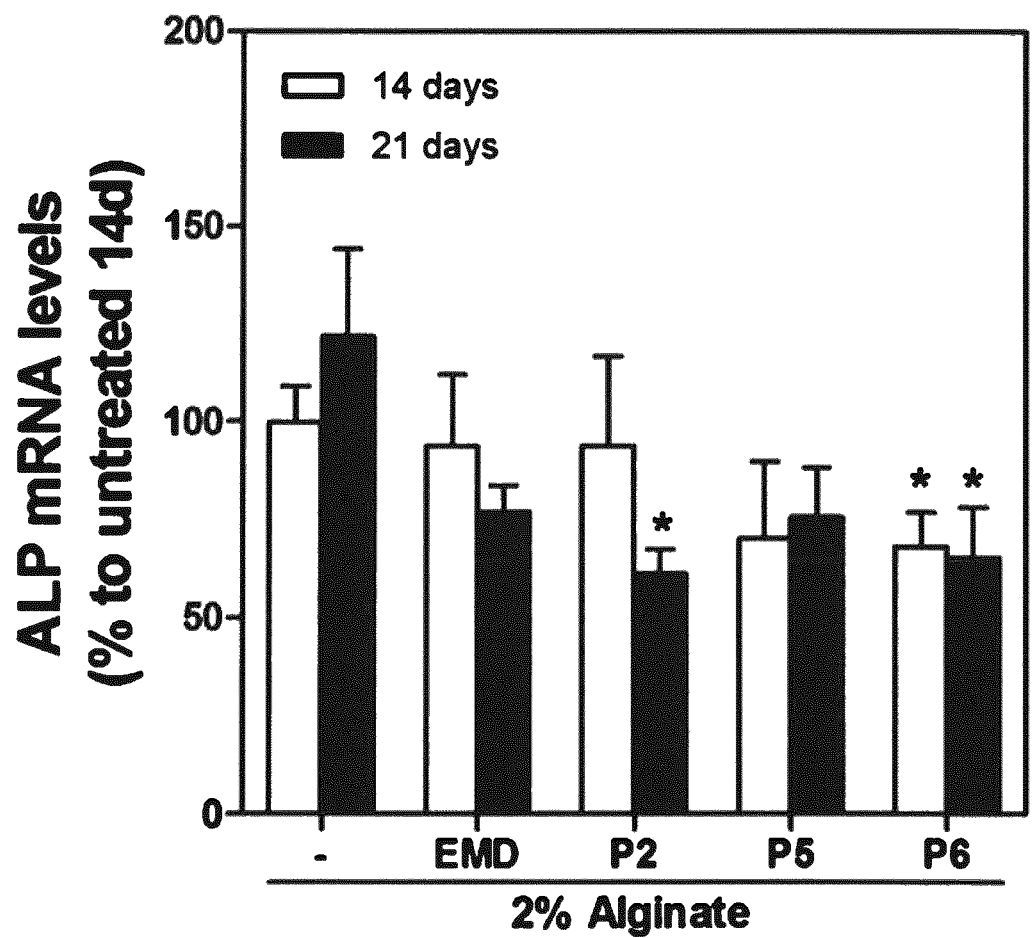
Figure 6E:
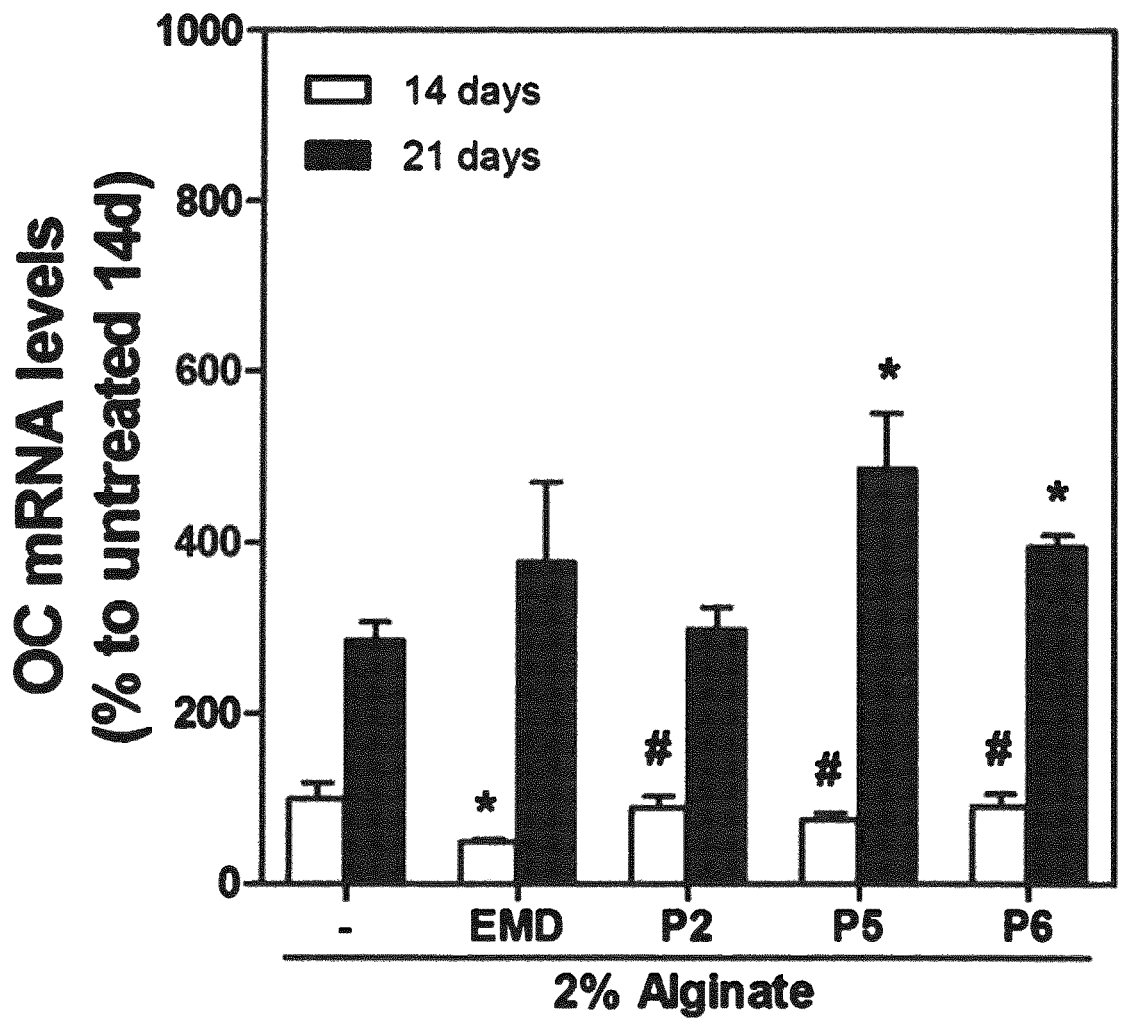
Figure 6F:
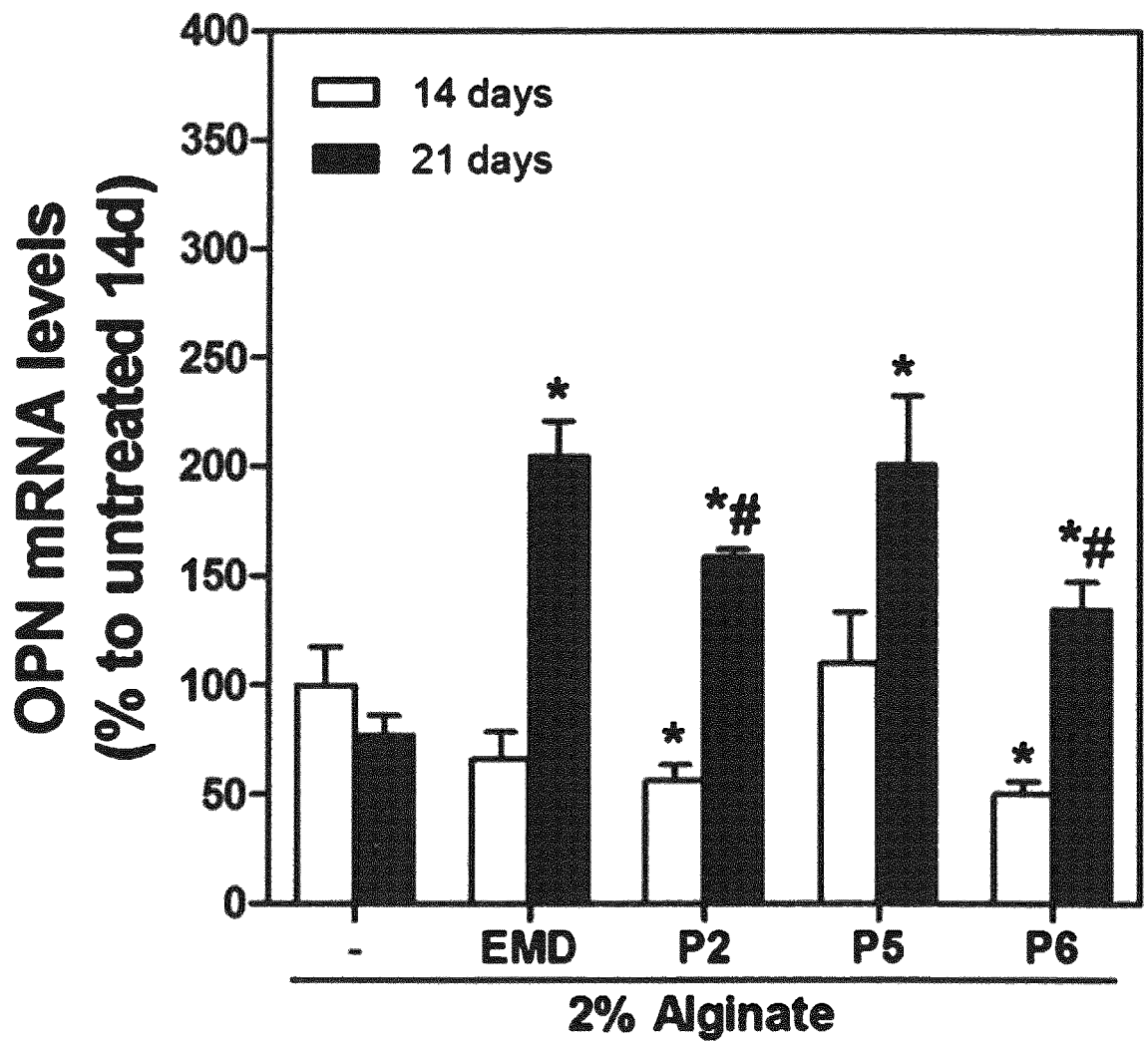

Coll-I gene expression decreased significantly after 14 days of treatment with any of the synthetic peptides compared to control (FIG. 6B)). No differences in Bsp mRNA levels were found among the different treatments (FIG. 6C). ALP mRNA levels significantly decreased after treatment with P6 for 14 days and 21 days and with P2 after 21 days of treatment compared to control (FIG. 6D)). After 14 days of cell culture, increased Oc mRNA levels were detected in cells cultured onto 2% alginate gel and containing synthetic peptides compared to cells treated with EMD. After 21 days, cells treated with P5 or P6 increased Oc mRNA levels when compared to control (FIG. 6(E)). Expression of Opn decreased significantly after 14 days of culture with P2 and P6 compared to control. After 21 days, Opn mRNA levels increased significantly with any of the synthetic peptides and EMD compared to control. EMD treatment markedly increased mRNA expression levels of Opn compared to P2 and P6 treatment (FIG. 6F)).

Discussion

Polyproline-rich synthetic peptides have previously been shown to induce bone formation and mineralization in vitro and to decrease bone resorption in vivo. The aim of this study was to develop a suitable formulation with a hydrogel for local treatment with these synthetic peptides to promote bone formation and mineralization, either alone or as a biodegradable coating for skeletal implants.

In the present study, cells were exposed to alginate gel containing different synthetic peptides and cultured for a long-term period in order to evaluate the effect of those peptides on the biological response of osteoblasts. The optimal formulation of the hydrogel has to allow the formation of a compact structure for a controlled, local and specific bioactive molecule delivery. Such features are governed by the physical property (e.g. mechanics, degradation, gel formation), the mass transport property (e.g. diffusion) and the biological interaction requirements (e.g. cell adhesion and signaling) of each specific application.

Previous studies carried out using alginate gel (Protanal LF200M, FMC polymers, Oslo, Norway) at different polymer concentrations (1%, 2%, 3%, 6% and 10%) have shown a decrease in pore size as the polymer concentration increases, resulting in the concentration of 2% as the most promising formulation to act as a peptide vehicle. Taking this in mind, 2% alginate hydrogel was ionically cross-linked with 300 mM of $CaCl_2$ and selected as the material of choice.

SEM analysis of the microstructure of both alginate gels with and without synthetic peptides after a process of lyophilization disclosed a porous and interconnected structure with a pore diameter of 42-44 μm; nevertheless, a compact structure with a pore size of approximately 1 μm diameter was observed after SEM analysis of non-lyophilized gels (data not shown). Diffusion rate of proteins is affected by the molecular weight and size of the diffusion species (defined by Stokes radii) compared to these pores and depends on the chemical nature of the protein (interactions molecule-alginate, polarization, i.e. hydrophilic drugs may diffuse very quickly while hydrophobic drugs diffuse slowly through the gel pores). Due to the fact that synthetic peptides used in the present study are small peptides with 25 amino acids length (molecular weight into the range of 2509.17-2782.34 Da), an easy diffusion rate through the gel should be expected. Accordingly, in the present study, peptide loaded into 2% alginate hydrogels exhibited a burst release during the first 24 h of incubation followed by progressive and sustained release during the 21 day period.

The efficiency of alginate gel for cell adhesion and proliferation was also examined since alginate has been described as an inert substrate with insufficient protein interaction for cell attachment, and it has been suggested that mammalian cells cannot interact with unmodified alginate hydrogels. In fact, to get a highly specific adhesive surface, most of the studies with alginate hydrogel covalently couple to the polymer an entire ECM protein or a peptide sequence capable of binding to cellular receptors. Indeed, some studies have reported that modification of alginate with an RGD-containing peptide promoted cell adhesion and spreading, whereas minimal cell adhesion was observed on unmodified alginate hydrogels. However, the present study shows that unmodified alginate hydrogel (Pronova UP LVG®) allow cell attachment and spreading. The differences among the reported studies seem to be due to the described relationship between the composition and purity of the alginate gels used and the ability of cells to proliferate on their surfaces. In the present study the alginate used contained a minimum of 60% G-fractions, therefore, allowing cell attachment and spreading. The optimal seeding density for the in vitro studies was evaluated by DNA quantification. The results showed that $100 \times 10^3$ cells/well was the density with higher efficiency in both, cell adhesion and cell proliferation and, therefore, was chosen for further studies. The alginate hydrogel showed to be non-toxic for the MC3T3-E1 cells, displaying some kind of protective effect on cell viability compared to cells cultured on tissue culture plastic. Moreover, it was validated that the synthetic peptides administered as a hydrogel formulation are non-cytotoxic, in agreement with the results obtained in previous studies after short- and long-time cell treatment.

Stable osteoblastic cell adhesion is largely mediated by integrins, heterodimeric receptors composed of α and β subunits that dimerize in specific combinations and interact with extracellular matrix proteins. It has been shown that osteoblasts express different integrin receptors depending on the material where they are grown. In addition to their role in cell adhesion, integrins regulate cytoskeleton organization and mediate signal transduction, and therefore regulate the expression of genes controlling proliferation, differentiation and matrix remodeling.

In order to investigate if the synthetic peptides may affect integrin expression and cell adhesion on the alginate hydrogels, the mRNA expression levels of Itga8, Itgb1, Itgb3 and the extracellular matrix protein Fn1 were studied. The expression of Itgb1, Itgb3 and Fn1 was significantly decreased after 14 days of treatment with synthetic peptides, especially for P2 and P6. The β1integrin subunit is found in the bone receptors for collagen, fibronectin and laminin mediating adhesion of osteoblasts to ECM whereas αvβ3- integrin would mediate the adhesion to Opn and vitronectin. Of interest is the finding that expression of αvβ3-integrin stimulates cell proliferation, and inhibits matrix mineralization in osteoblast cells; and that FN—an abundant ECM protein that binds to a large number of Integrins, including β1- and β3-integrin subunits—is as well highly expressed in the early stages of osteogenesis while during cell maturation its accumulation in the matrix is reduced. Moreover, treatment with the synthetic peptides increased significantly Itga8 expression after 21 days of treatment, and markedly when cells were treated with P5. Itga8 has been shown to interact with osteopontin (Opn), a protein secreted by osteoblasts involved in cell adhesion and proliferation, whose expression is increased after mineralization has been initiated. Here, bilateral correlation analysis of the Itga8 and the Opn mRNA expression levels showed a Pearson correlation of 0.678 ($p<0.01$). These results might indicate that cells treated with the synthetic peptides are in a later stage of cell maturation compared to the control group, and are in line with the expression results of the osteoblast markers analyzed. It has been described that the short sequence of PPXPP in the C-terminal region of peptides participates in the transactivation activity of transcription factors and/or co-activators. The mode of action of the synthetic peptides might involve interaction with a receptor capable of influencing intracellular signaling cascades, and that the exposition of their C termini containing conserved proline-rich region (PPLPP) may be of importance in the signaling activity of the synthetic peptides. The synthetic peptides show signature of compact, well-packed structures lacking secondary structure elements, as expected due to the rich content of prolines and expose their PPLPP stretch in a way suitable for interactions. While peptide 2 and peptide 6 present two distinct loops, peptide 5 has different topology of loops that makes possible a contact between C and N terminus. Therefore, the fact these structural differences in the accessibility of the C terminus and structural rigidity of this short consensus sequences (PPXPP) between different peptides could affect in the interaction with a receptor may explain the differential expression of adhesion genes.

On one hand it was found that osteocalcin, the most specific and the latest of expressed osteoblast markers with a role in mineralization, was significantly induced after 14 and 21 days of treatment with the formulated synthetic peptides compared to untreated and EMD alginate gel, i.e. in agreement with the results obtained when administered in the culture media. Accordingly, Opn, a sialoprotein produced at various stages of differentiation with higher levels expressed after mineralization has been initiated, was significantly up-regulated after 21 days of treatment with both EMD and synthetic peptides compared to control. On the other hand, at the time points studied, no differences were observed in the expression of genes related to osteogenesis (Coll-I, Bmp-2, Bsp and Alp), as these genes are regulated at earlier stages than osteocalcin during osteoblast differentiation, mainly in the proliferation and matrix maturation phase. It is interesting to note that all the studies that have been performed so far with the synthetic peptides have repetitively shown an increase in osteocalcin mRNA levels, both in vitro and in vivo. The relevance of this marker has been demonstrated in a recent in vivo study (Monjo M et al., 2012), where the best predictive marker for osseointegration of Ti implants among all was osteocalcin. It is suggested that the synthetic peptides improve the alginate hydrogel properties for cell attachment and that the cells cultured on the hydrogel formulated with synthetic peptides were at a more mature stage of the differentiation process over the cells cultured on control hydrogel and hydrogel formulated with EMD.

It may be hypothesized that the mode of action of the synthetic peptides might involve interaction with a receptor capable of influencing intracellular signaling cascades at the initial states of cell differentiation to finally stimulate osteoblast-differentiation and that the accessibility and structural rigidity of this short consensus sequence (PPXPP) may be of importance in the signaling activity of the synthetic peptides. Further, from the present results it is hypothesized that the peptides could bind to the integrins expressed on cell surface, which first could increase the osteoblast attachment on the alginate hydrogel surface and secondly modulate the expression of genes related with mature osteoblast phenotype.

Conclusion

In conclusion, the results demonstrate that 2% of alginate hydrogel is a suitable formulation for the local delivery of synthetic polyproline-rich peptides, inducing integrin alpha 8, osteopontin and osteocalcin expression in MC3T3-E1 cells. These peptide-modified alginate hydrogels may represent a new generation of injectable carriers with biologically active substance for bone tissue engineering applications and are promising for use as biodegradable coatings for skeletal implants, such as titanium dioxide scaffolds.

Example 2

Preparation of an Alginate Coated Titanium Dioxide Scaffold

Material and Methods
2.1. Preparation of Synthetic Peptide 2 (P2).

Synthetic proline-rich peptide 2 (P2) (2HN-PLVPSQ-PLVPSQPLVPSQPQPPLPP-COOH) (SEQ ID NO 1) was purchased from Eurogentec (Seraing, Belgium). One vial containing 7.2 mg of the selected synthetic peptide was delivered in a freeze-dried pellet form and dissolved to 10 mg/ml in 0.1% acetic acid in phosphate-buffered saline (PBS) (PAA Laboratories GmbH, Pasching, Austria).

Aliquots to avoid repeated freeze-thaw cycles were prepared and stored at −20° C. until use.
2.2. Preparation of 2% Alginate Containing Peptide 2.

Sodium alginate (Pronova UP LVG®)—a low viscosity alginate where minimum 60% of monomers are guluronate—was purchased from NovaMatrix (FMC BioPolymer AS, Norway).

The sodium alginate was used without further purification. Quantity (2%, w/v) of sodium alginate was dissolved in distilled water by stirring for 3 h at room temperature to get a homogenous alginate solution. A fixed concentration (50 µg/ml) of P2 was added to the solution and stirred for 1 h.
2.3. Fabrication of $TiO_2$ Scaffolds Coated with 2% Alginate Containing P2.

The porous $TiO_2$ scaffolds were produced by polymer sponge replication as previously described by (Tiainen H et al., 2010), with a size of 9 mm of diameter and 8 mm high. Then, $TiO_2$ scaffolds were coated with one layer of 2% alginate gel with or without P2. Briefly, $TiO_2$ scaffolds were submerged into 2% alginate solution with or without P2 under agitation at 100 rpm on an orbital shaker (IKA Vibrax VXR basic, Staufen, Germany) for 1 h at room temperature. Scaffolds were then centrifuged at 252×g for 1 min. Samples were immersed into 50 mM $CaCl_2$ for 1 h to allow gelation. Scaffolds were then rinsed with $dH_2O$ to remove the excess of $CaCl_2$. Finally, samples were let to dry overnight at room temperature. Scaffolds coated with one layer of 2% alginate gel (control alginate scaffold), were used as control group, whereas uncoated $TiO_2$ scaffolds (without alginate, SC) were also used as control group.

2.4. Peptide 2 Release Profile from $TiO_2$ Scaffolds Coated with 2% Alginate Gel.

$TiO_2$ scaffolds coated with 2% alginate containing peptide 2 (P2-alginate-coated scaffold) were placed into 48-well plates (Nunc GmBh & Co. Kg, Langenselbold, Germany) containing 1 ml distilled water (pH 7.4). In order to mimic cell culture conditions, the samples were agitated on an orbital shaker at 200 rpm (IKA® Schüttler MTS 2, Germany) for 6 h at 37° C. and in humidity conditions (using a distilled water container). Then, samples were maintained at 37° C. in a humidified atmosphere for up to 21 days. At prefixed time points (2d, 5d, 7d, 9d, 12d, 14d, 16d, 19d and 21d), distilled water was collected and fresh distilled water was added into each well. Sample absorbances were analyzed by UV-Vis spectrophotometer (PerkinElmer® Lambda 25 UV/Vis Systems, USA) at a wavelength of 206 nm to determine the amount of peptide released. In parallel, T102 scaffolds coated with one layer of 2% alginate gel were used as control to subtract absorbance values obtained from degradation products from alginate.

Relative absorbance units were correlated with the amount of peptide released using a linear standard curve for each time point and the cumulative P2 released was then calculated. The experiment was performed in triplicate.

2.5. Cell Culture of MC3T3-E1 on Coated and Uncoated TiO2 Scaffolds.

$TiO_2$ scaffolds (SC) uncoated and coated with 2% alginate with or without peptide (P2 and control (–)) were placed into 48-well plates (Nunc GmBH & CO. KG, Langenselbold, Germany) in sterile conditions. Cells were seeded at a density of 200,000 cells/scaffold and maintained in α-MEM (PAA Laboratories, Pasching, Austria) supplemented with 10% FBS (PAA Laboratories, Pasching, Austria) and 100 U penicillin/ml and 100 µg streptomycin/ml antibiotics (PAA Laboratories, Pasching, Austria). In order to guarantee a homogenous cell distribution inside the scaffold, an agitated seeding method was used (Takahashi Y et al., 2003). Briefly, after adding 1 ml of cell suspension to the scaffolds, plates were agitated on an orbital shaker (Unitron, Infors HT, Basel, Switzerland) for 6 h at 180 rpm at 37° C. and in humidity conditions. Then, cells were maintained at 37° C. in a humidified atmosphere of 5% $CO_2$ for up to 21 days. Culture media (1 ml) was refreshed every other day.

Culture media was collected after 48 h of treatment to test cytotoxicity (LDH activity).

To assess the ability of cell proliferation into this 3D system, the number of cells after 7 days was also studied by DNA quantification using Hoechst staining. In parallel, the cell attachment of MC3T3-E1 into the scaffold was also visualized by SEM after 7 and 21 days of culture.

Expression of markers related to osteoblast cell maturation and differentiation after 7 and 21 days of cell culture was assessed by real-time RT-PCR.

2.6. SEM Visualization of 2% Alginate-Coated TiO2 Scaffolds.

Morphology of alginate-coated $TiO_2$ scaffolds was observed using a scanning electron microscope (SEM, Hitachi S-3400N, Hitachi High-Technologies Europe GmbH, Krefeld, Germany). SEM was further used to visualize the cell adhesion into the $TiO_2$ scaffold structure after 7 and 21 days of culture. Briefly, cells were washed twice with PBS and fixed with glutaraldehyde 4% in PBS for 2 h. Then the fixative solution was removed and the cells were washed with distilled water twice. At 30 minute intervals, the cells were dehydrated by the addition of 50%, 70%, 90% and 100% ethanol solutions. Ethanol was removed and the cells were left at room temperature to evaporate the remaining ethanol.

Scaffolds were observed at 10 kV and 40 Pa using back scattered and secondary electrons detector. Images presented are from a representative area.

2.7. Cell Viability.

The lactate dehydrogenase (LDH) activity determined in the culture media after 48 h was taken as an indicator of cell survival. The activity of the cytosolic enzyme was determined according to the manufacturer's kit instructions (Roche Diagnostics, Mannheim, Germany).

Results were presented relative to the LDH activity in the medium of cells cultured in uncoated scaffolds, which were set to 100%.

2.8. Cell Number Determination.

Cells growing on the 3D scaffolds were lysed by a freeze-thaw method in deionised destilled water. Cell lysates were used for determination of DNA quantity using Hoechst 33258 fluorescence assay. Samples were mixed with 20 µg/ml of Hoechst 33258 fluorescence stain (Sigma, St. Quentin Fallavier, France) in TNE buffer, and the intensity of fluorescence was measured at excitation and emission wavelengths of 356/465 nm using a multifunction microplate reader (Cary Eclipse fluorescence spectrophotometer, Agilent Technologies, Santa Clara, United States). Relative fluorescence units were correlated with the cell number using a linear standard curve. 2.9. RNA isolation and real-time RT-PCR analysis.

Total RNA was isolated using Tripure® (Roche Diagnostics, Mannheim, Germany), according to the manufacturer's protocol. Total RNA was quantified at 260 nm using a Nanodrop spectrophotometer (NanoDrop Technologies, Wilmington, Del., USA). The same amount of total RNA (850 ng) was reverse transcribed to cDNA at 42° C. for 60 min using High Capacity RNA-to-cDNA kit (Applied Biosystems, Foster City, Calif.), according to the protocol of the supplier. Aliquots of each cDNA were frozen (−20° C.) until the PCR reactions were carried out.

Real-time PCR was performed in the Lightcycler 480® (Roche Diagnostics, Mannheim, Germany) using SYBR green detection. Real-time PCR was done for two reference genes (18SrRNA and glyceraldehyde-3-phosphate dehydrogenase (Gapdh)) and 12 target genes (integrin alpha8 (Itga8), integrin beta1 (Itgb1), integrin beta3 (Itgb3), fibronectin 1 (Fn1), osterix (Osx), bone morphogenetic protein 2 (Bmp2), collagen-I (Coll-I), interleukin-6 (Il-6), bone sialoprotein (Bsp), alkaline phosphatase (Alp), osteocalcin (Oc) and osteopontin (Opn)).

The primer sequences are detailed in table 3.

TABLE 3

Primer sequences of osteoblast markers related genes used in the real-time PCR.

| Gene | Primer sequence | |
|---|---|---|
| 18S | S 5'-GTAACCCGTTGAACCCCATT-3' | (SEQ ID NO 7) |
|  | A 5'-CCATCCAATCGGTAGTAGCG-3' | (SEQ ID NO 8) |
| Gapdh | S 5'-ACCCAGAAGACTGTGGATGG-3' | (SEQ ID NO 9) |
|  | A 5'-CACATTGGGGGTAGGAACAC-3' | (SEQ ID NO 10) |
| Itgb1 | S 5'-AGCAGGCGTGGTTGCTGGAA-3' | (SEQ ID NO 13) |
|  | A 5'-TTTCACCCGTGTCCCACTTGGC-3' | (SEQ ID NO 14) |

TABLE 3-continued

Primer sequences of osteoblast markers related genes used in the real-time PCR.

| Gene | Primer sequence | | |
|------|---|---|---|
| Itgb3 | S | 5'-AGGGGAGATGTGTTCCGGCCA-3' | (SEQ ID NO 15) |
|  | A | 5'-ACACACAGCTGCCGCACTCG-3' | (SEQ ID NO 16) |
| Fn1 | S | 5'-GCTGCCAGGAGACAGCCGTG-3' | (SEQ ID NO 17) |
|  | A | 5'-GTCTTGCCGCCCTTCGGTGG-3' | (SEQ ID NO 18) |
| Itga8 | S | 5'-TCGCCTGGGAGGAGGCGAAA-3' | (SEQ ID NO 11) |
|  | A | 5'-TCTTAACCGCTGTGCTCCCCG-3' | (SEQ ID NO 12) |
| Osx | S | 5'-ACTGGCTAGGTGGTGGTCAG-3' | (SEQ ID NO 31) |
|  | A | 5'-GGTAGGGAGCTGGGTTAAGG-3' | (SEQ ID NO 32) |
| Bmp2 | S | 5'-GCTCCACAAACGAGAAAAG-C-3' | (SEQ ID NO 33) |
|  | A | 5'-AGCAAGGGGAAAAGGACACT-3' | (SEQ ID NO 34) |
| Coll-I | S | 5'-AGAGC-ATGACCGATGGATTC-3' | (SEQ ID NO 21) |
|  | A | 5'-CCTTCTTGAGGTTGCCAGTC-3' | (SEQ ID NO 22) |
| Il-6 | S | 5'-ACTTCCATCCAGTTGCCTTC-3' | (SEQ ID NO 35) |
|  | A | 5'-TTTCCACGATTTCCCAGAGA-3' | (SEQ ID NO 36) |
| Bsp | S | 5'-GAAAATGGAGACGGCGATAG-3' | (SEQ ID NO 23) |
|  | A | 5'-ACCCGAGAGTGTGGAAAGTG-3' | (SEQ ID NO 24) |
| Alp | S | 5'-AACCCAGACACAAGCATTCC-3' | (SEQ ID NO 25) |
|  | A | 5'-GAGAGCGAAGGGTCAGTCAG-3' | (SEQ ID NO 26) |
| Oc | S | 5'-CCGGGAGCAGTGTGAGCTTA-3' | (SEQ ID NO 27) |
|  | A | 5'-TAGATGC-GTTTGTAGGCGGTC-3' | (SEQ ID NO 28) |
| Opn | S | 5'-TCTGCGGCAGGCATTCTCGG-3' | (SEQ ID NO 29) |
|  | A | 5'-GTCACTTTCACCGGGAGGGAGGA-3' | (SEQ ID NO 30) |

Each reaction contained 7 µl Lightcycler-FastStart DNA MasterPLUS SYBR Green I (containing Fast Start Taq polymerase, reaction buffer, dNTPs mix, SYBRGreen I dye and MgCl2), 0.5 µM of each, the sense and the antisense specific primers and 3 µl of the cDNA dilution in a final volume of 10 µl. The amplification program consisted of a preincubation step for denaturation of the template cDNA (10 min 95° C.), followed by 45 cycles consisting of a denaturation step (10 s 95° C.), an annealing step (8-10 s 60° C., except for Osx that was 5 s 68° C. and Alp that was 8 s 65° C.) and an extension step (10 s 72° C.).

After each cycle, fluorescence was measured at 72° C. (λex 470 nm, λem 530 nm). A negative control without cDNA template was run in each assay.

Real-time efficiencies were calculated from the given slopes in the LightCycler 480 software using serial dilutions, showing all the investigated transcripts high real-time PCR efficiency rates, and high linearity when different concentrations are used. PCR products were subjected to a melting curve analysis on the LightCycler and subsequently 2% agarose/TAE gel electrophoresis to confirm amplification specificity, Tm and amplicon size, respectively.

Relative quantification after PCR was calculated by dividing the concentration of the target gene in each sample by the mean of the concentration of the two reference genes in the same sample using the Advanced relative quantification method provided by the LightCycler 480 analysis software version 1.5 (Roche Diagnostics, Mannheim, Germany).

2.10. Statistics

All data are presented as mean values ±SEM. A Kolmogorov-Smirnov test was done to assume parametric or non-parametric distributions for the normality tests, differences between groups were assessed by Mann-Whitney-test or by Student t-test depending on their normal distribution. SPSS® program for Windows (Chicago, Ill., US), version 17.0 was used. Results were considered statistically significant at p-values ≤0.05.

Results

Peptide Release.

Figure 7:
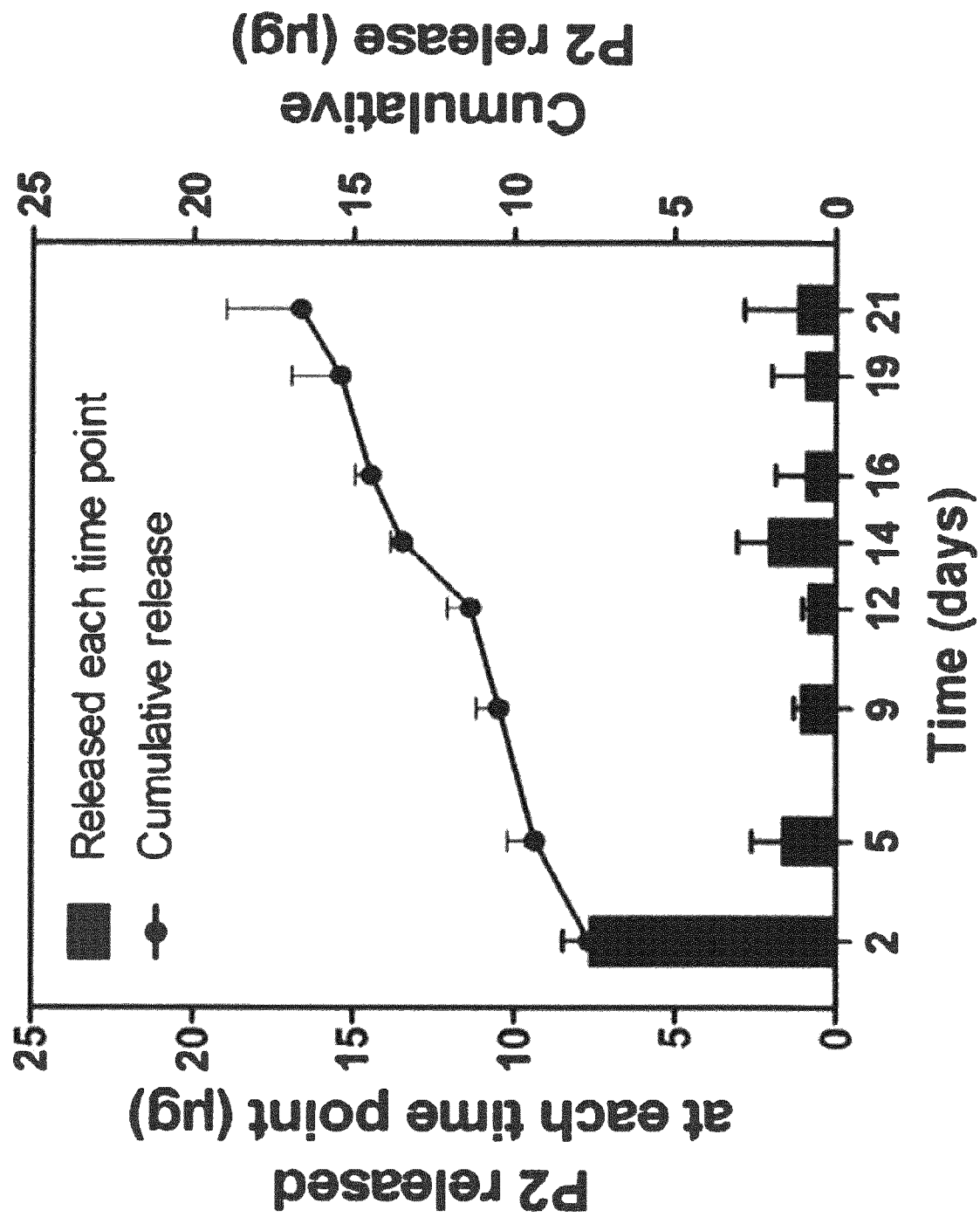
FIG. 7. Release profile of peptide 2 (SEQ ID NO 1) from P2-alginate-hydrogel coated scaffolds after 21 days of incubation at 37° C. Bar graph show the amount of peptide released after each time point. Line graph represents cumulative amount of peptide released up to 21 days. Values represent mean±SD.

Peptide release profile from P2-alginate-coated scaffolds is depicted in FIG. 7. A burst release of the peptide during the first 2 days of incubation was observed (42.8% of the cumulative amount of P2 released after 21 days). After 5 days, the amount of peptide released decreased to a 9.4% (of the cumulative amount released up to 21 days) followed by a slower but sustained peptide release over time up to 21 days of incubation. Further, the cumulative release suggests that, after 21 days of incubation, there were still P2 entrapped into the 2% alginate gel.

LDH Activity.

Figure 8:
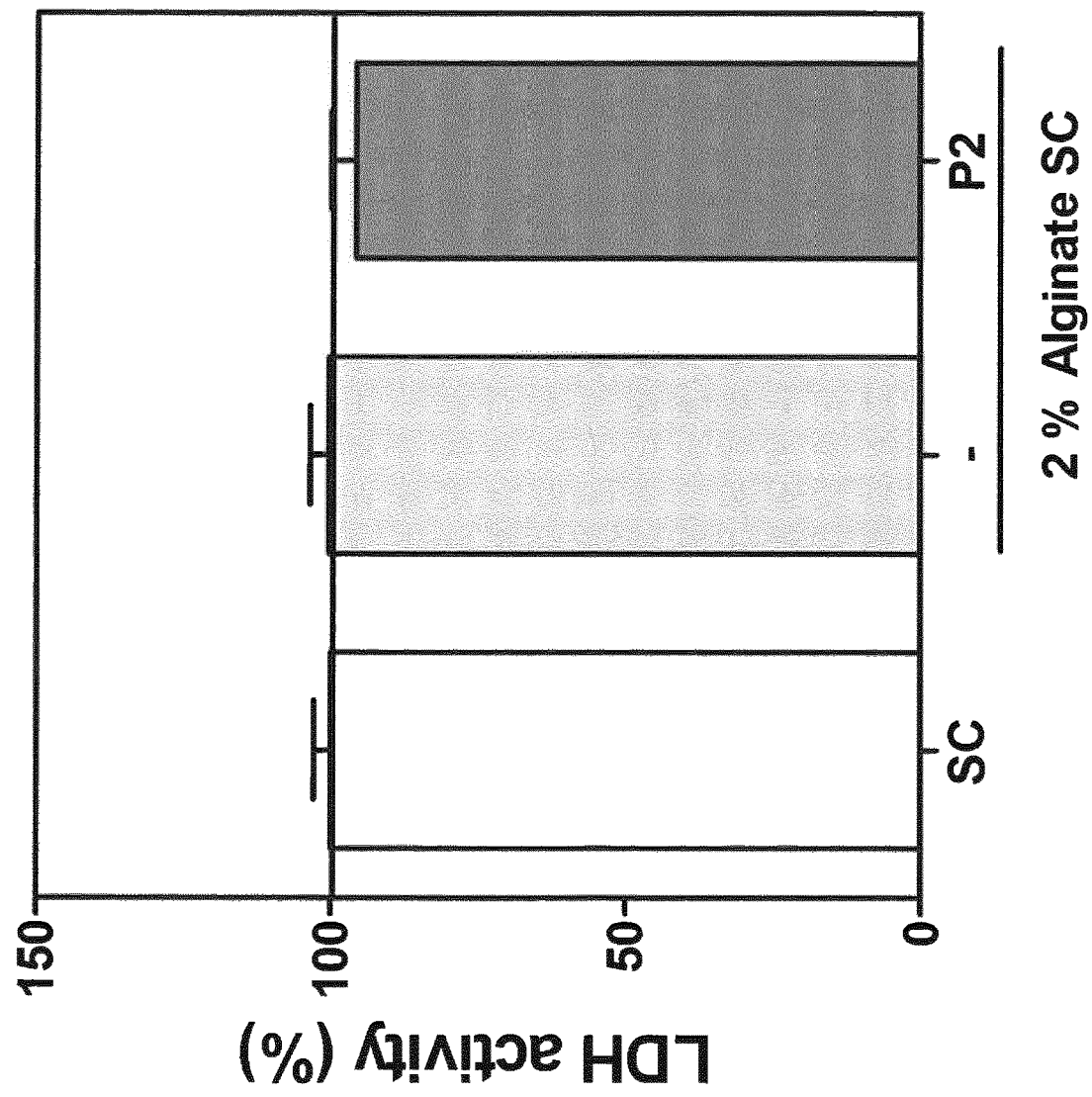
FIG. 8. LDH activity measured from culture media collected after 48 h of culture. Values represent the mean ±SEM. Mann-Whitney test (p≤0.05): (a) versus regular scaffold (SC) and (b) versus control alginate hydrogel coated scaffold (−).

As shown in FIG. 8, no toxic effects were observed for any of the experimental groups studied. Similar percentage of cell viability was determined in all the groups tested, indicating that either control alginate scaffolds (−) and P2-alginate-coated scaffolds (P2) did not show any toxic effects on cells after 48 h of cell culture.

SEM Visualization of $TiO_2$ Scaffolds Coated with 2% Alginate Gel.

Figure 9:
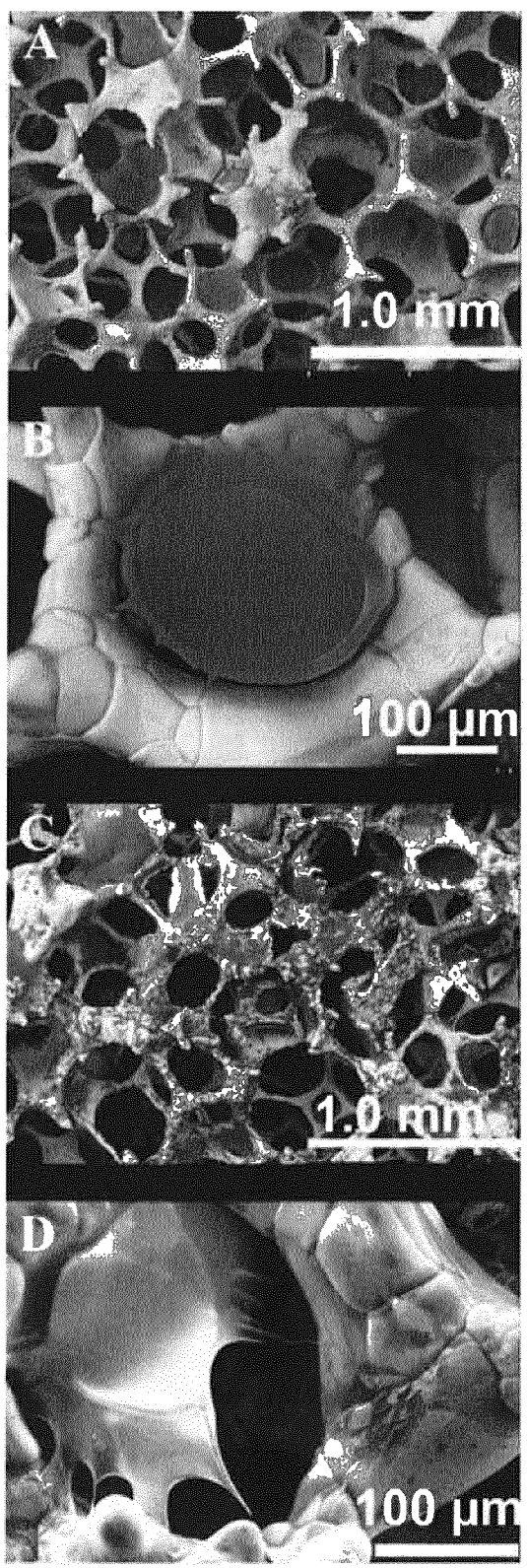
FIG. 9. SEM visualization of 2% alginate hydrogel coated $TiO_2$ scaffolds (control alginate scaffold) at 10 kV and 40 Pa. Figures A and B show the microstructure of $TiO_2$ scaffolds right after the coating process with one layer of 2% alginate hydrogel at 50× (A) and 300× (B) of magnification. Figures C and D show cells cultured on control alginate scaffolds after 7 days of culture at 50× (C) and 300× (D) of magnification.

Alginate-coated $TiO_2$ scaffolds were observed by SEM. As shown in FIGS. 9A and 9B, some pores of the $TiO_2$ scaffolds were blocked after the coating process with alginate, though, after cell seeding and 7 days of Incubation in standard cell culture conditions (37° C. and in a humidified atmosphere), almost all pores were unblocked (FIGS. 9C and 9D). Thus, certain degradation of the blocking alginate gel was seen in those pores that remained blocked right after the coating process.

Figure 10:
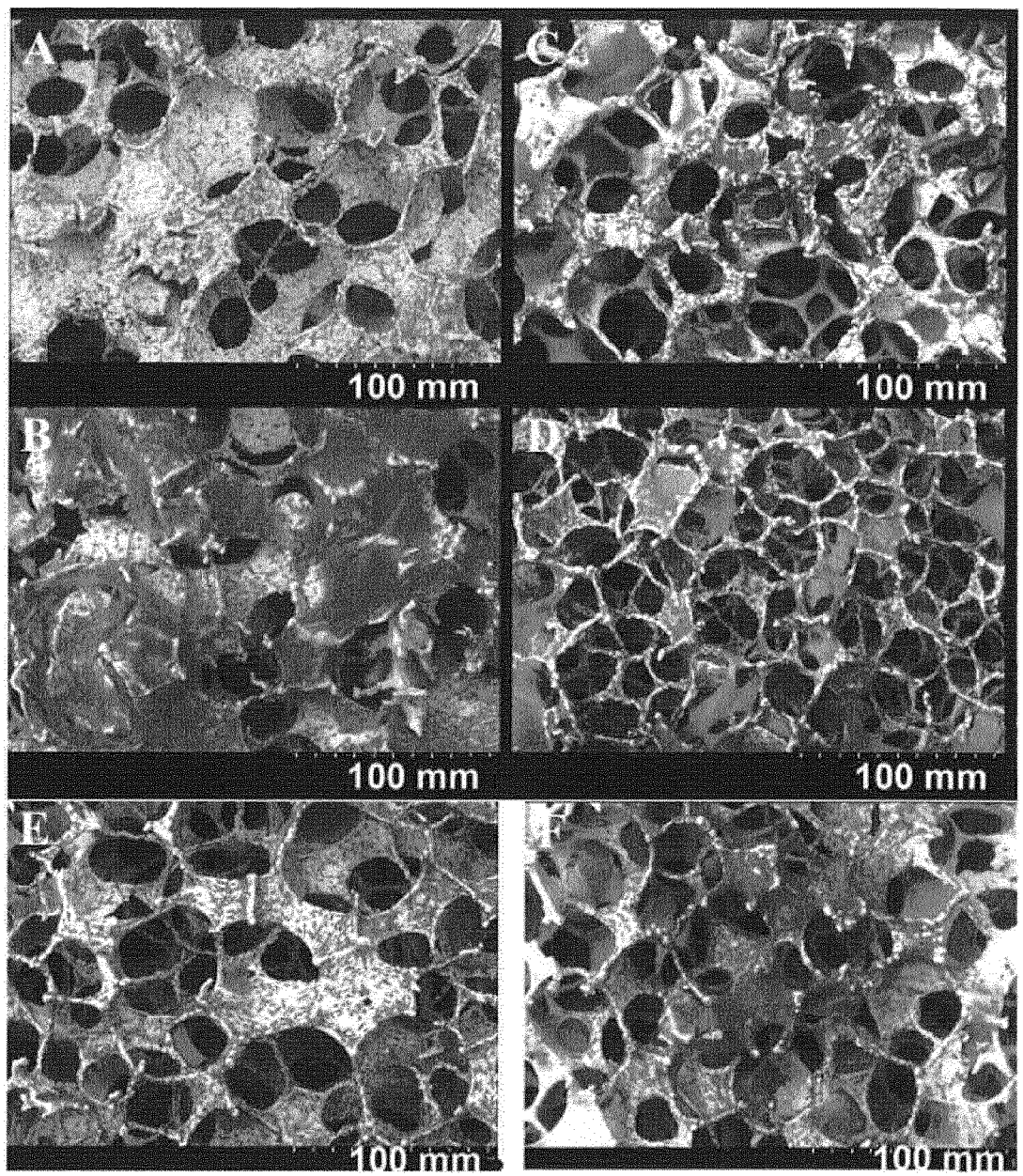
FIG. 10. SEM visualization of MC3T3-E1 cells growing on regular scaffolds (A and B), control alginate scaffolds (C and D) and P2-alginate hydrogel coated scaffolds (E and F) after 7 (A, C and E) and 21 (B, D and F) days of culture. Scaffolds were observed by SEM at 10 kV, 40 Pa and ×50 of magnification.

Although the amount of cells growing on uncoated $TiO_2$ scaffolds (SC) was higher (FIGS. 10A and 10B) than on alginate-coated $TiO_2$ scaffolds (FIG. 10C-10F), cells were able to penetrate and to adhere into the coated scaffolds with 2% alginate gel either with or without P2.

An increase from day 7 to day 21 in the number of cells growing on the scaffolds was seen for all the experimental groups.

Cell Number.

Figure 11:
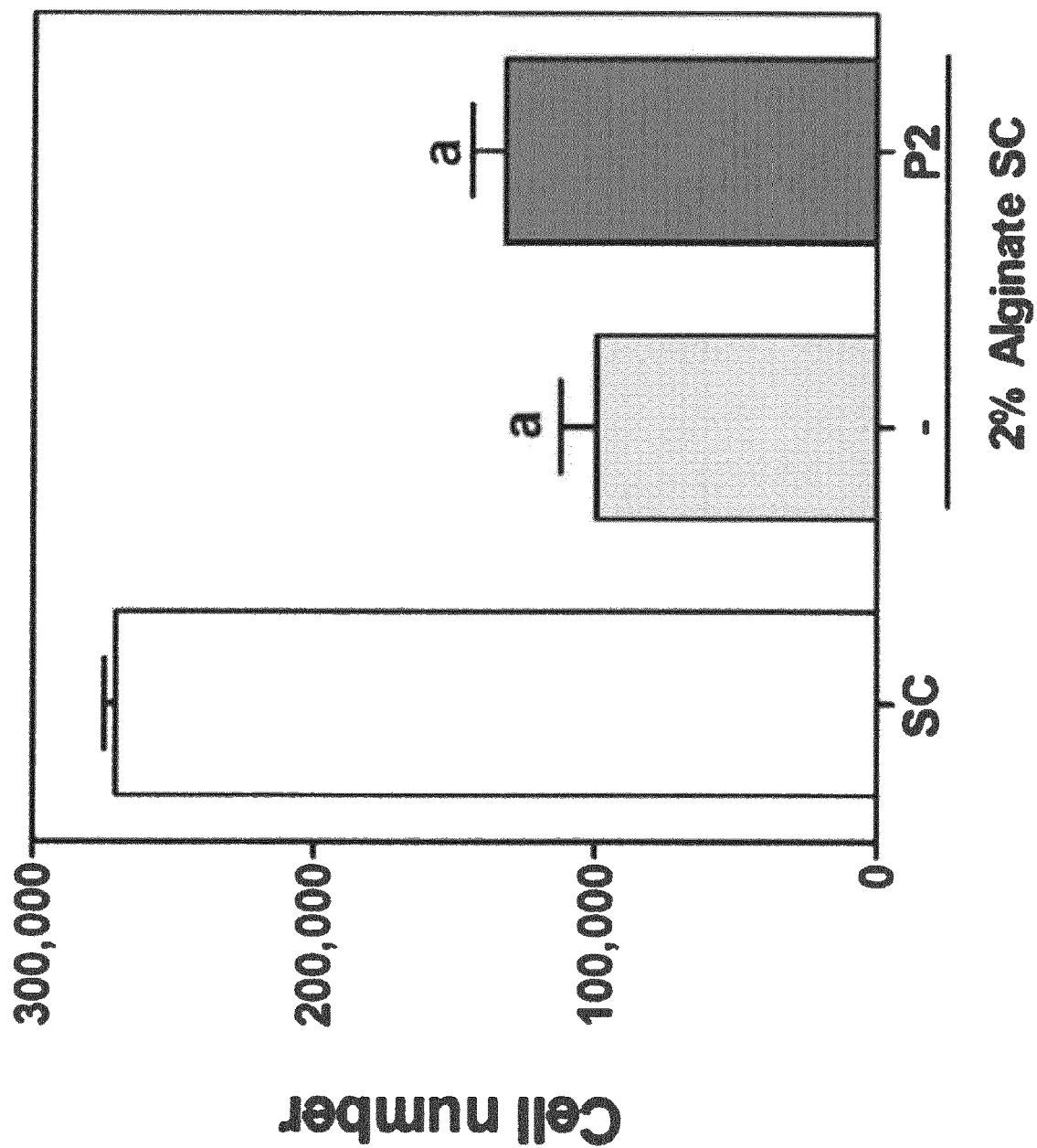
FIG. 11. Number of cells growing on the scaffolds after 7 days of culture. DNA content was analyzed by Hoechst fluorescence staining and correlated to a linear standard curve. Values represent the mean ±SEM. Values represent the mean ±SEM. Mann-Whitney test: (a) p≤0.05 versus regular scaffold (SC) and (b) versus control alginate hydrogel coated scaffold (−).
Figure 12A:
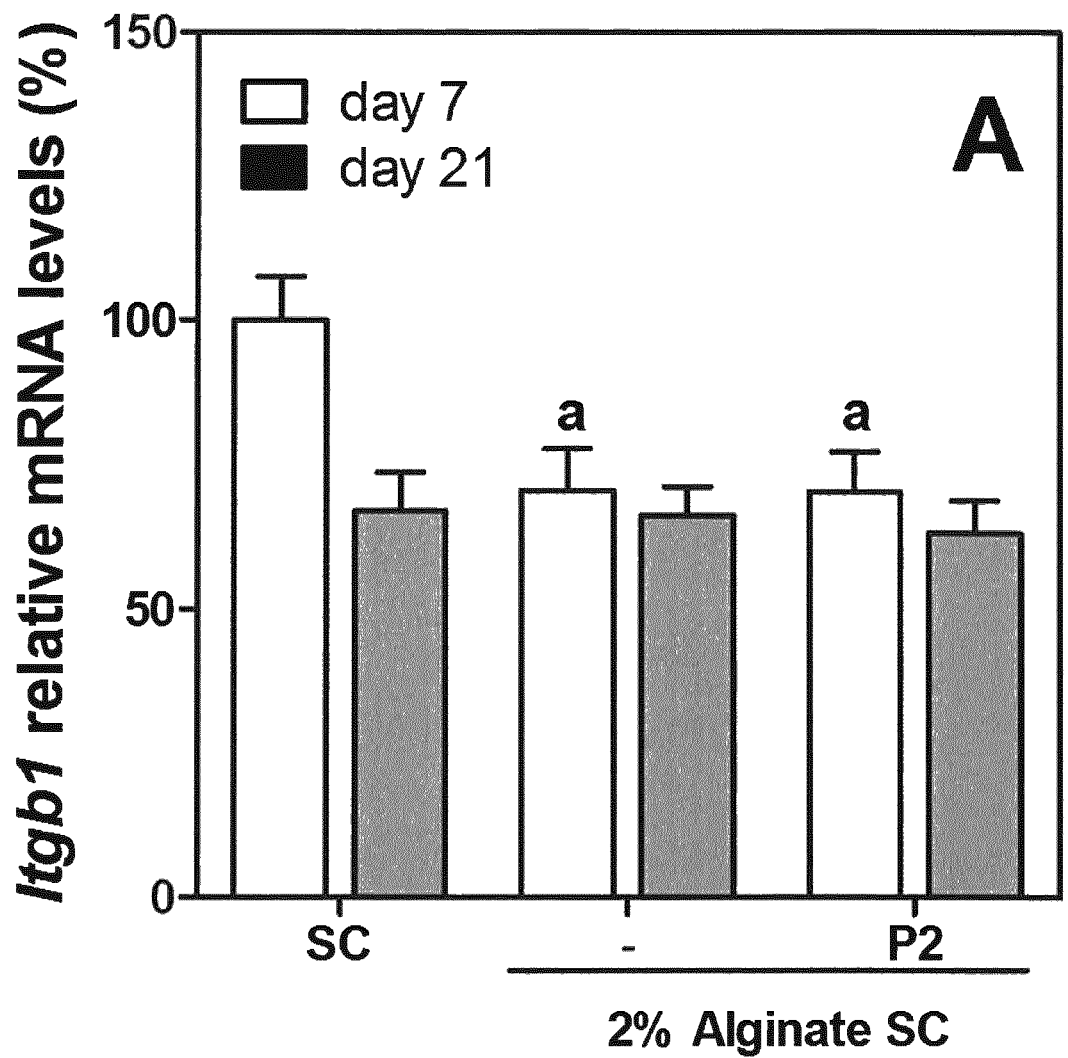
FIG. 12 A-D. Relative mRNA expression levels of Itgb1 (A), Itgb3 (B), Fn1(C) and Itga8 (D) in MC3T3-E1 cells cultured on $TiO_2$ scaffolds for 7 (□) and 21 days (■). Regular scaffolds (SC) were used as reference group. Data represent fold changes of target genes normalized with reference genes (Gapdh and 18S), expressed as a percentage of cells cultured on regular scaffolds (SC) at day 7, which were set to 100%. Values represent the mean: SEM. Student t-test: (a) p≤0.05 versus regular scaffold (SC) and (b) versus control alginate scaffold (−).
Figure 12B:
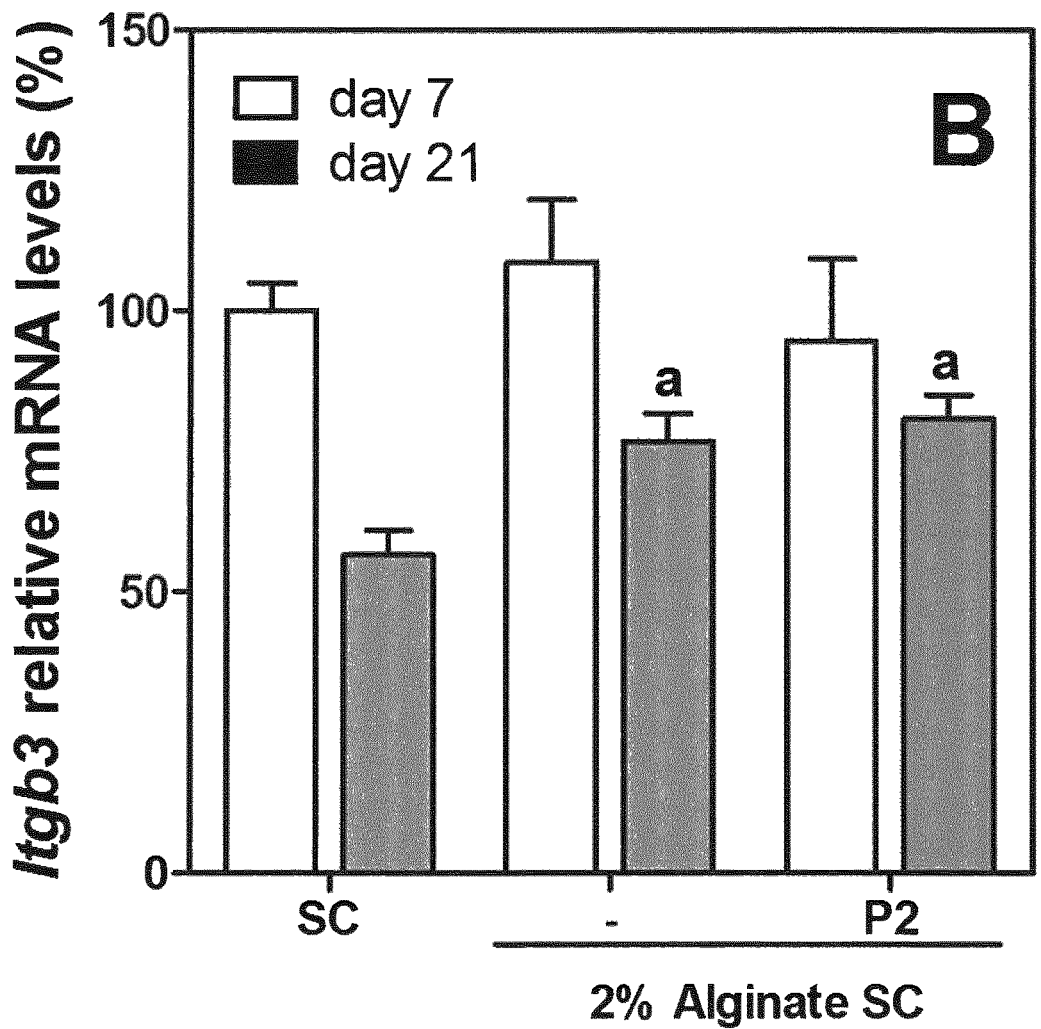
Figure 12C:
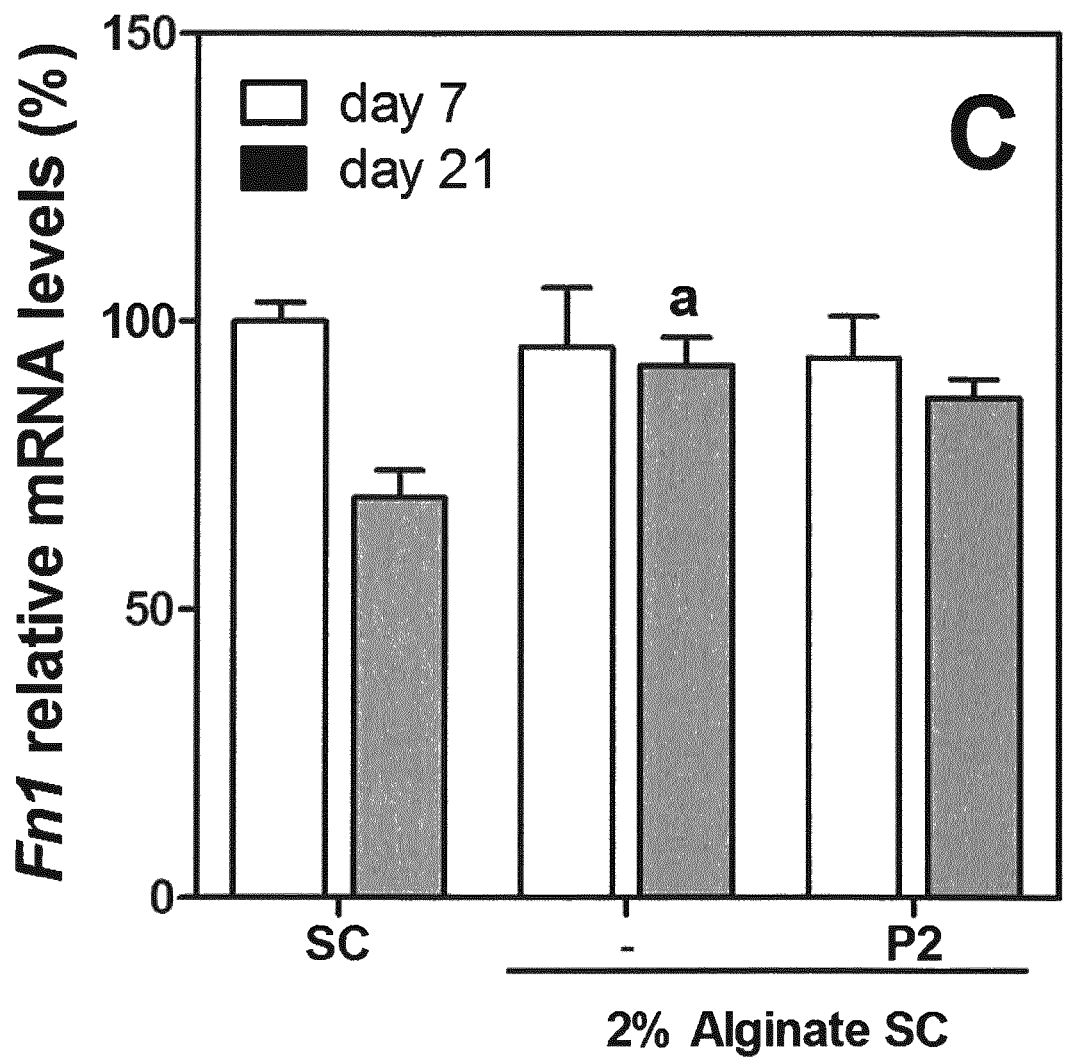
Figure 12D:
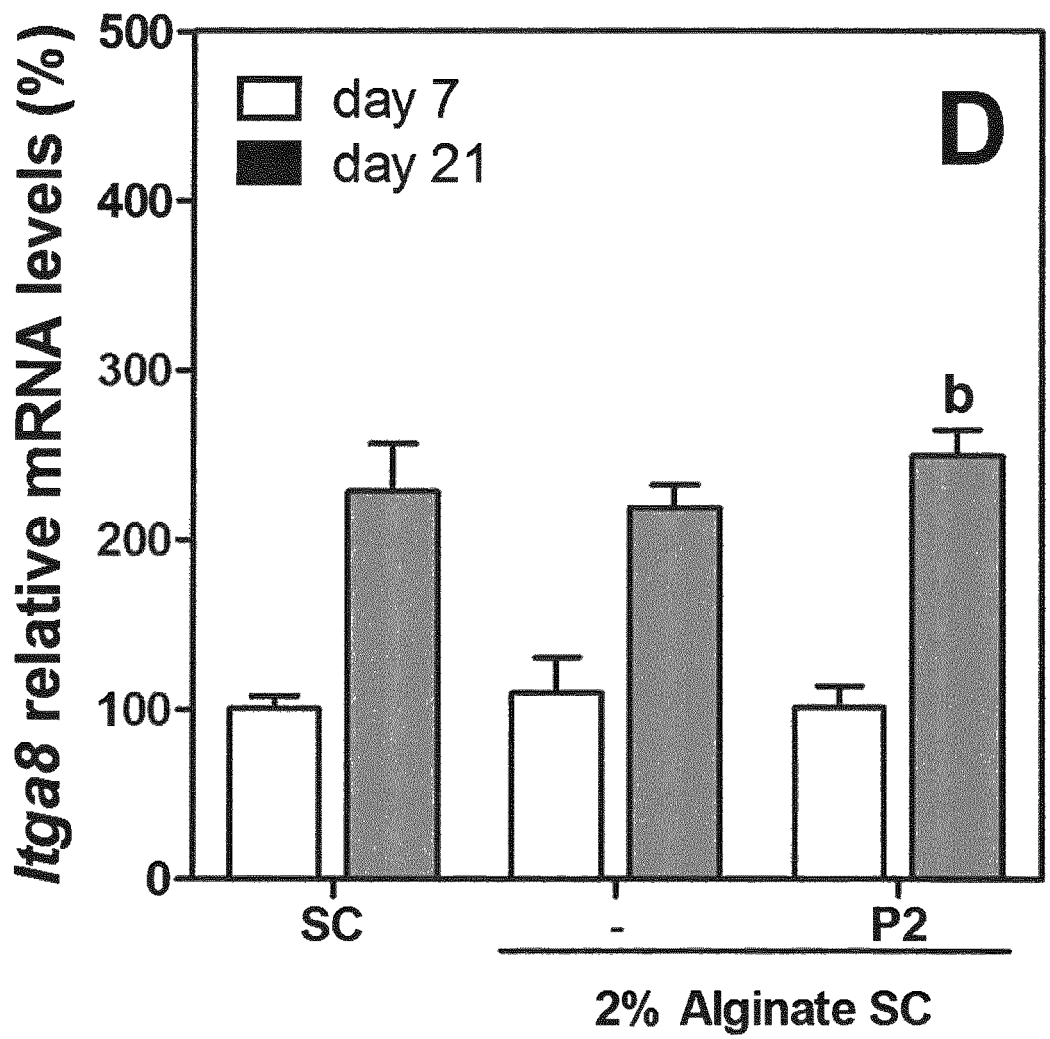
Figure 13A:
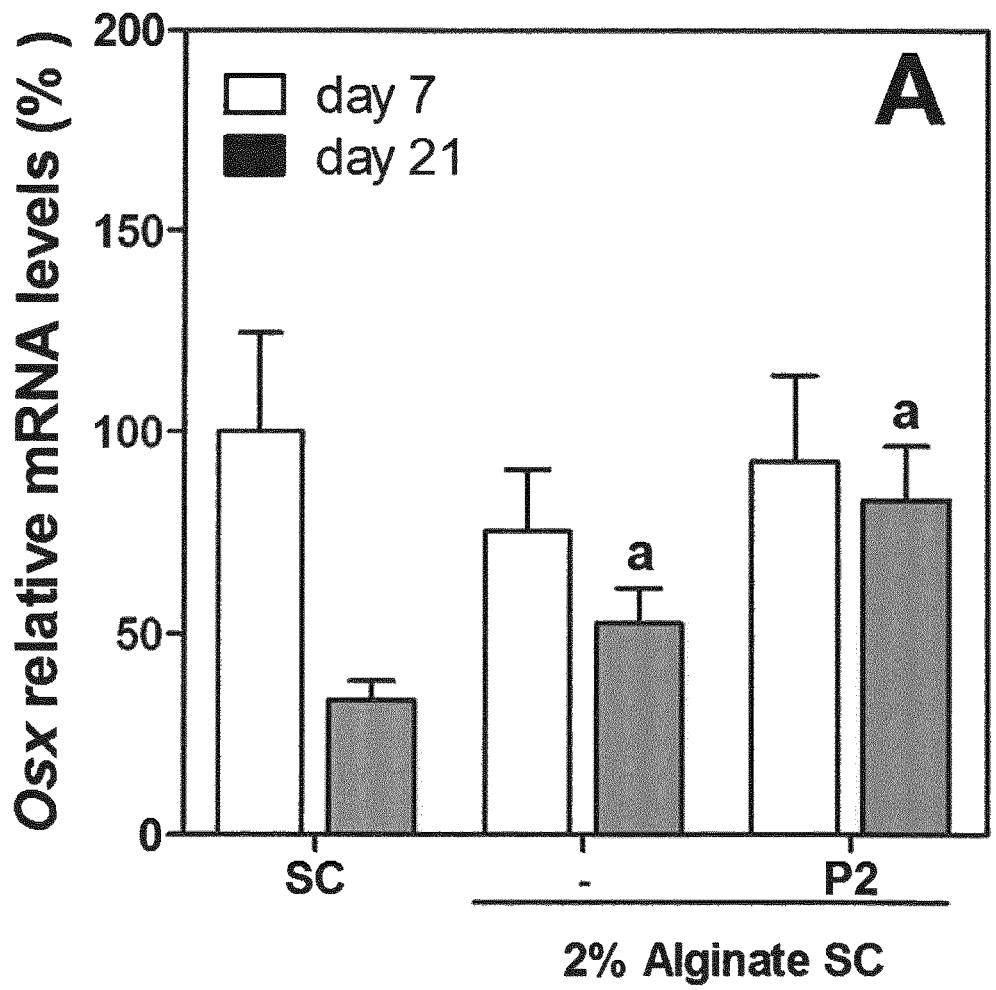
FIG. 13A-H. Relative mRNA expression levels of A) osterix (Osx), B) bone morphogenetic protein 2 (Bmp2), C) collagen-I (Coll-I), D) interleukin 6 (Il-6), E) osteopontin (Opn), F) bone sialoprotein (Bsp), G) alkaline phosphatase (Alp) and H) osteocalcin (Oc) in MC3T3-E1 cells cultured on $TiO_2$ scaffolds for 7 (□) and 21 days (■). Regular scaffolds (SC) were used as reference group. Data represent fold changes of target genes normalized with reference genes (Gapdh and 18S), expressed as a percentage of cells cultured on regular scaffolds (SC) at day 7, which were set to 100%. Values represent the mean +SEM. Student t-test: (a) p≤0.05 versus regular scaffold (SC) and (b) versus control alginate scaffold (−).
Figure 13B:
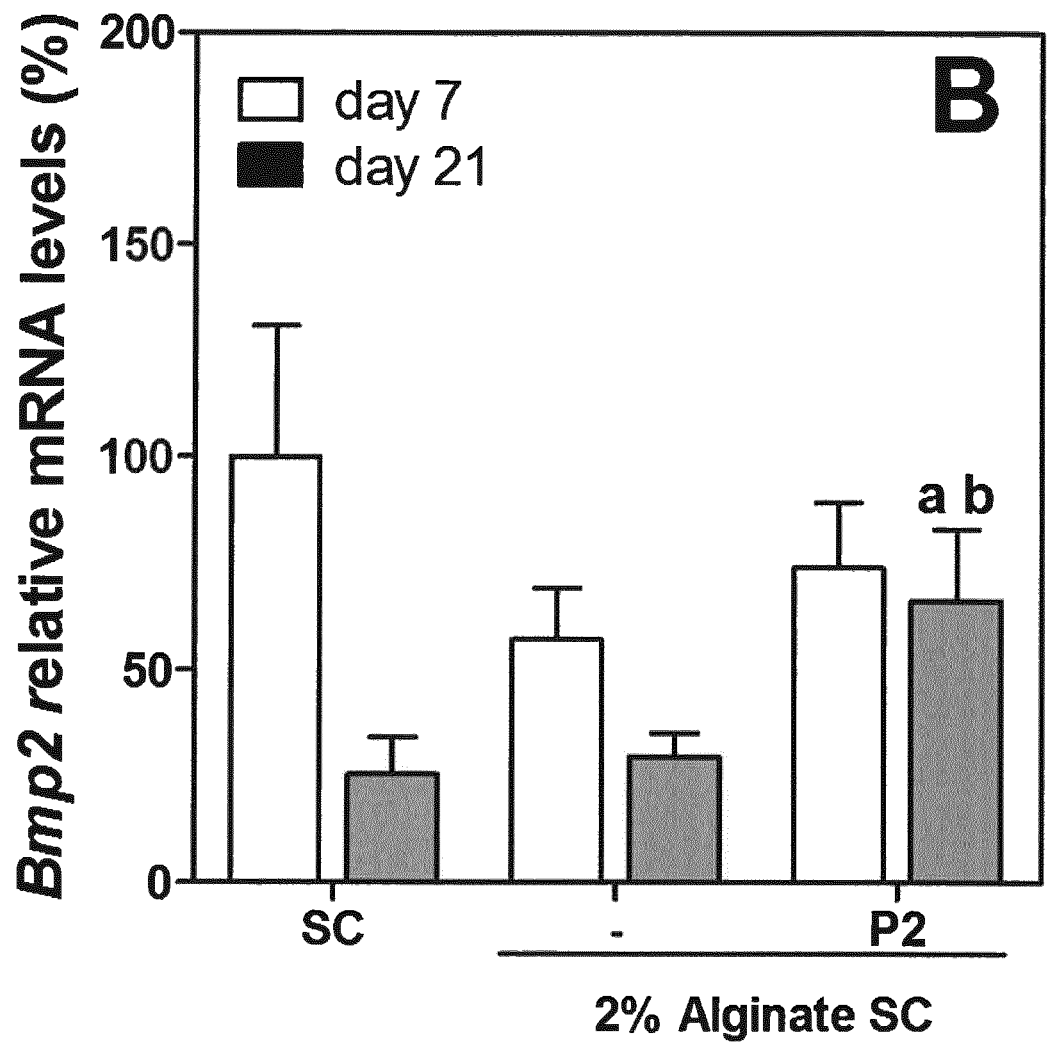
Figure 13C:
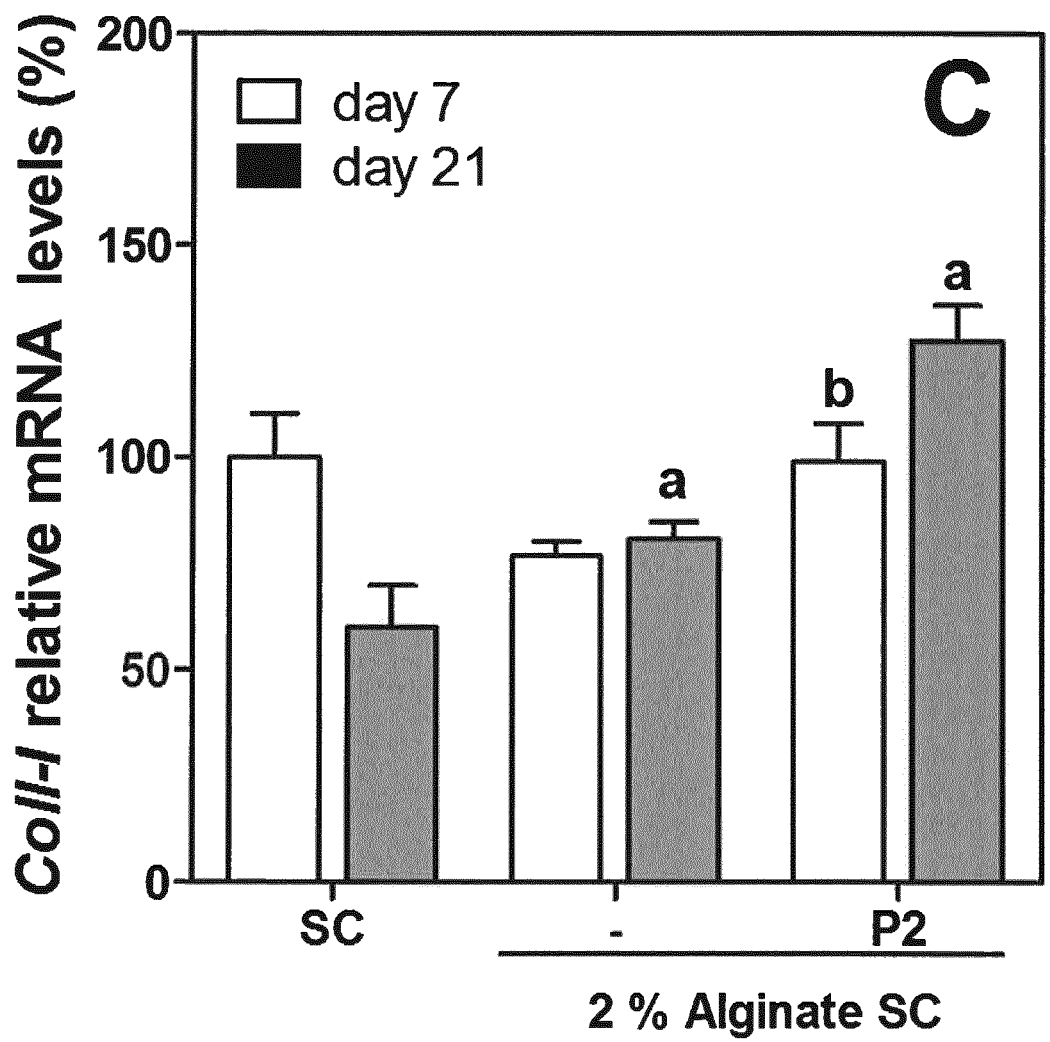
Figure 13D:
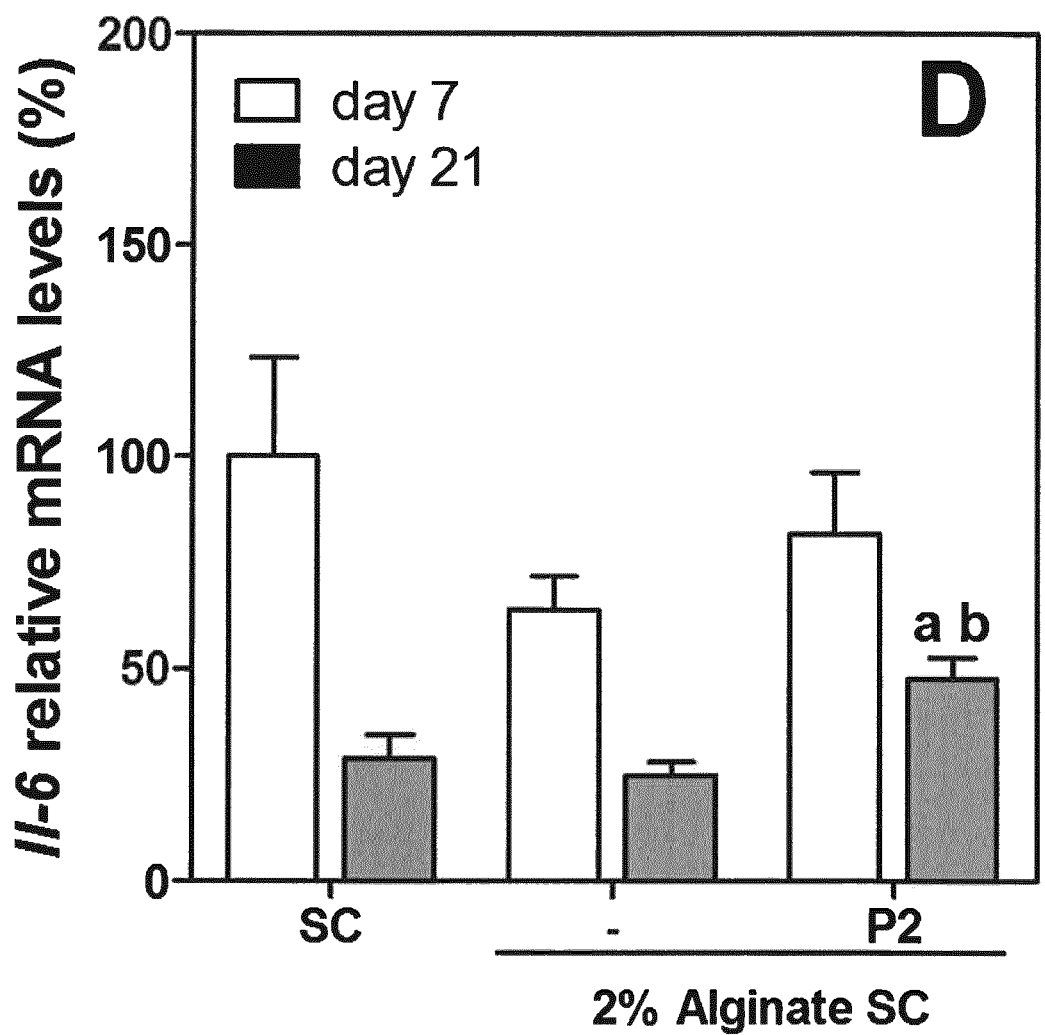
Figure 13E:
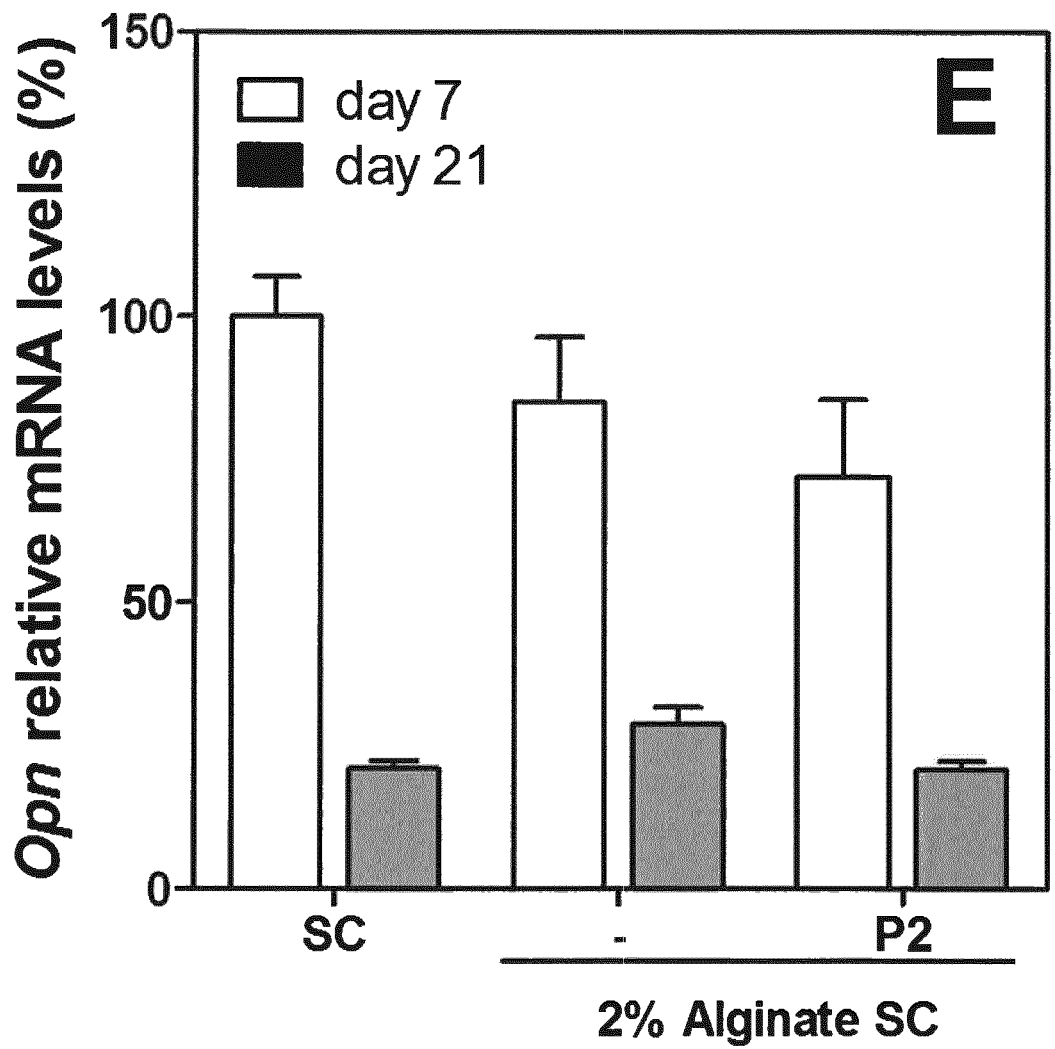
Figure 13F:
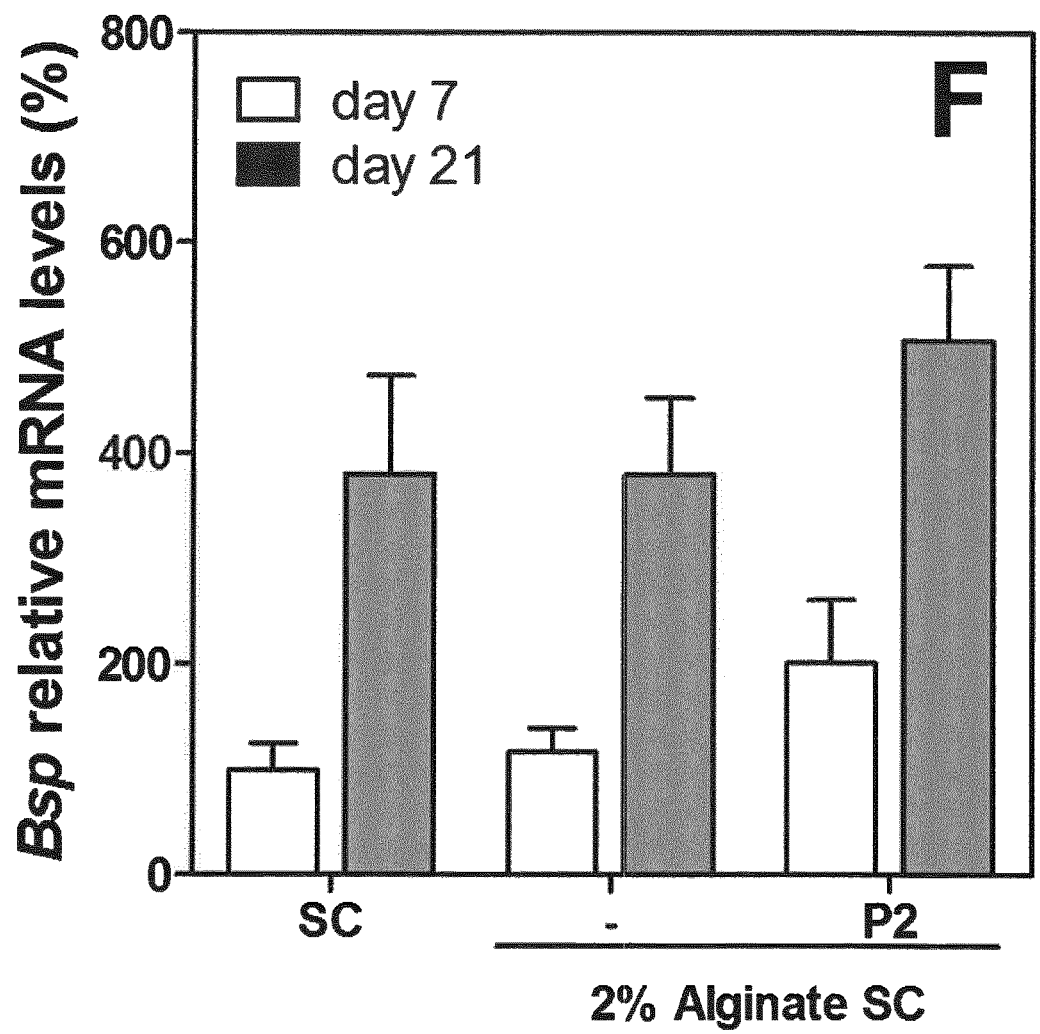
Figure 13G:
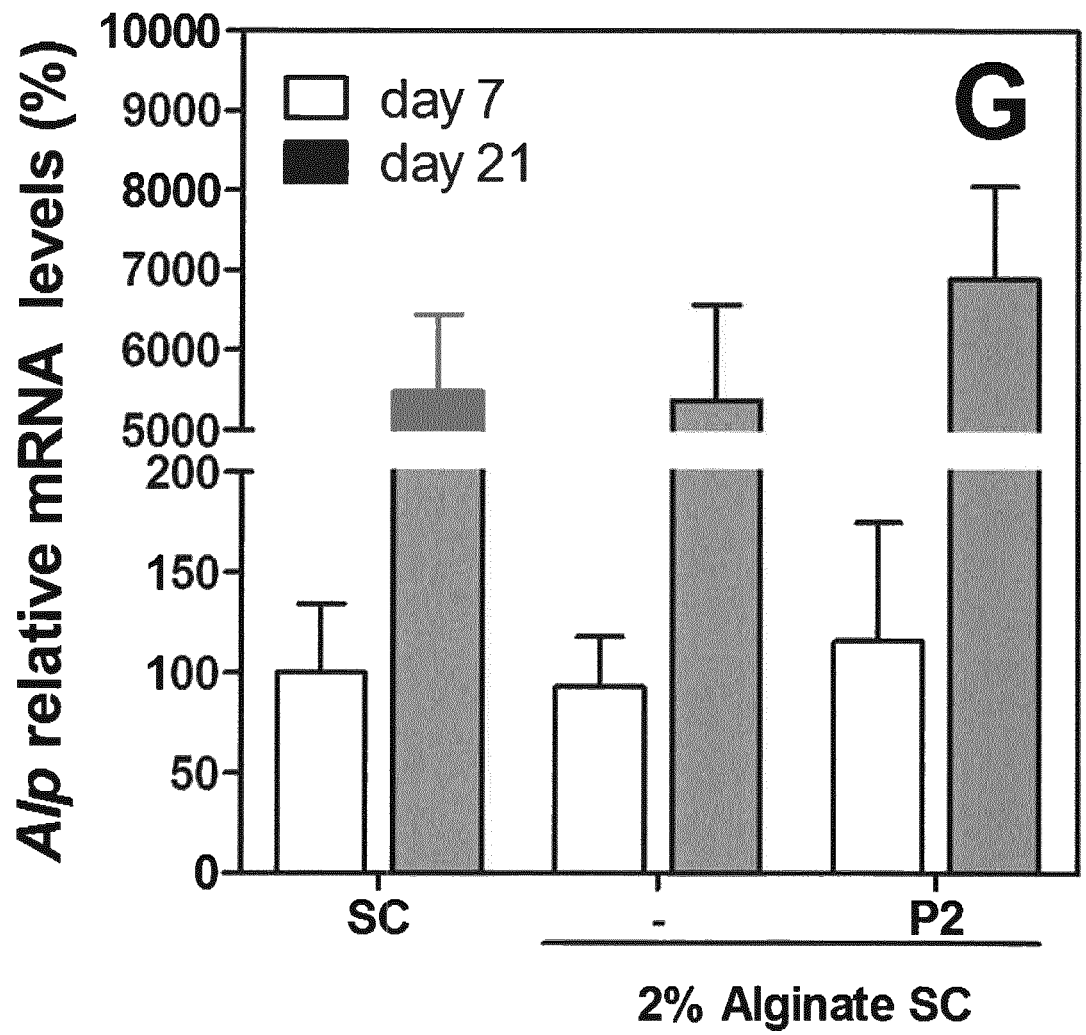
Figure 13H:
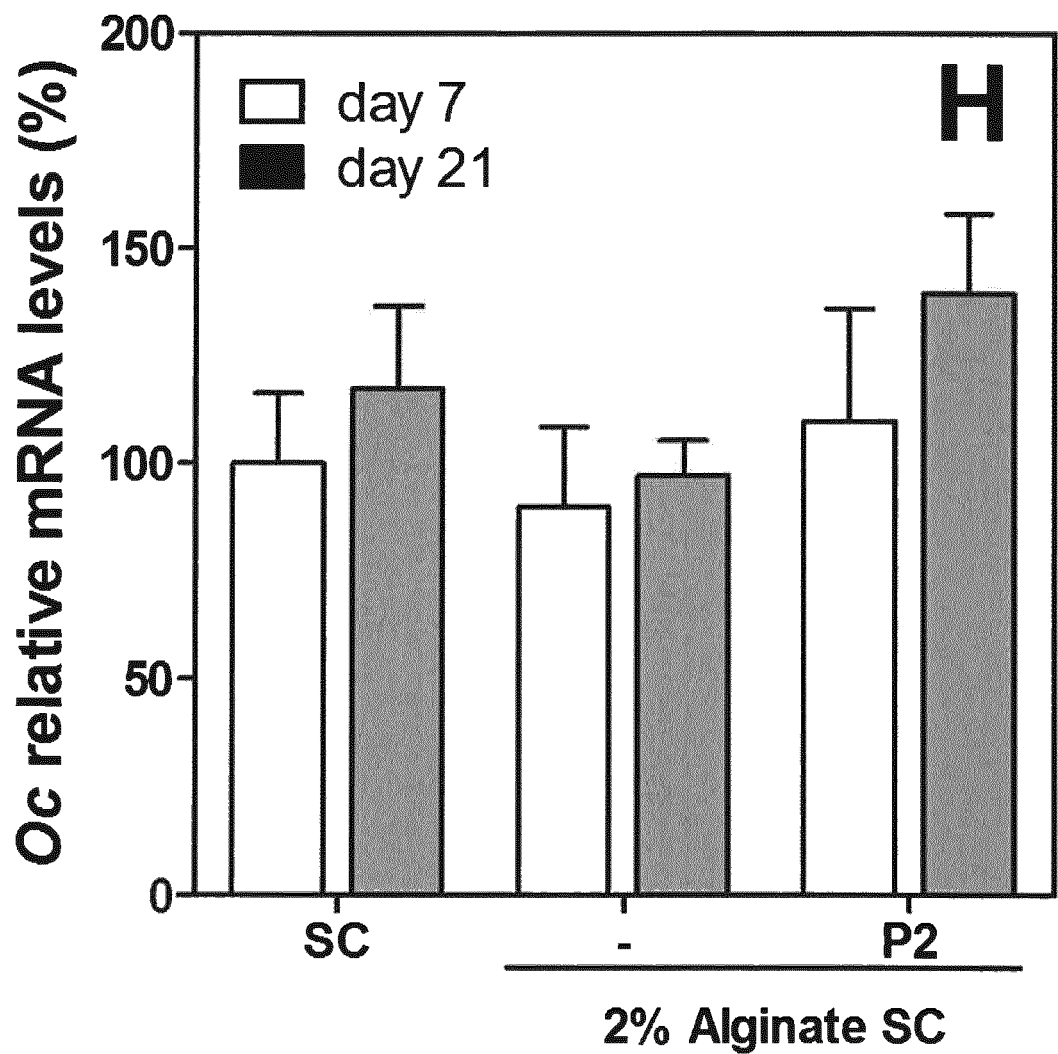

DNA quantification was used to determine the number of cells growing on the $TiO_2$ scaffolds after 7 days of culture (FIG. 11). In accordance to SEM images, after 7 days of culture, the number of cells was significantly lower in any of the alginate-coated $TiO_2$ scaffolds compared to $TiO_2$ scaffolds (SC). Thus, compared to SC, a 61% and a 49% reduction in cell number was found on alginate-coated scaffolds without and with P2, respectively. Although data did not reach statistical significance, scaffolds coated with P2 showed 32% more cells than the alginate control scaffolds (−).

Gene Expression of Cell Adhesion-Related Markers.

As shown in FIG. 12, relative mRNA levels of Itb1 were significantly decreased in cells growing onto alginate-coated scaffolds (either with or without P2) compared to $TiO_2$ scaffolds (SC) after 7 days of culture. Nevertheless, after 21 days of cell culture no differences were observed among groups. After 21 days, Itgb3 mRNA levels were increased in cells growing on alginate-coated scaffolds (either with or without P2) compared to $TiO_2$ scaffolds (SC). Higher mRNA levels of Fn1 were found in cells growing on 2% alginate-coated scaffolds after 21 days, and in cells growing on P2-alginate-coated scaffolds compared to uncoated scaffolds, although for the last group data did not reach statistical significance. Itga8 mRNA was significantly increased in cells growing on P2-alginate-coated scaffolds compared to control alginate scaffolds after 21 days of culture.

Gene Expression of Several Osteoblast Differentiation Markers.

FIG. 13 shows relative mRNA levels for several osteoblast differentiation marker genes. After 21 days of culture, osterix mRNA levels were increased in cells growing on alginate-coated scaffolds (either with or without P2) compared to uncoated scaffolds. Bmp-2 and Il-6 mRNA levels were significantly increased in cells cultured on P2-alginate-coated scaffolds compared to both uncoated scaffolds and alginate-coated scaffolds after 21 days of cell culture. Coll-I mRNA levels, a marker related with cell proliferation, were significantly increased in cells cultured on P2-alginate-coated scaffolds compared to alginate-coated scaffolds after 7 days of cell culture. After 21 days of culture Coll-I was significantly increased in both alginate-coated scaffolds and P2-alginate-coated scaffolds compared to uncoated scaffolds. No significant differences were observed in Opn, Bsp, Alp and Oc mRNA expression levels among experimental groups at any of the time points studied.

Discussion

In the present experiment, the suitability of a titanium dioxide scaffold coated with an alginate coating, with and without a biologically active substance for the use in load-bearing bone tissue applications to promote bone formation and mineralization was demonstrated. $TiO_2$ scaffolds have been reported to have strength up to 2.6 MPa in compressive strength (Tiainen H et al. 2010) and showed excellent mechanical resistance in a pig in vivo study.

In bone tissue engineering, the structure of the scaffold must provide an optimal microenvironment for osteogenesis. The scaffold porosity, pore network interconnectivity, the surface-area-to-volume ratio and the physico-chemical properties of the surface determines cell migration and differentiation, bone ingrowth, vascularization, and mass transfer between the cells and the environment. The use of highly porous $TiO_2$ scaffolds using an agitated cell seeding method has proved to achieve a good attachment and distribution of mouse preosteoblastic cells. In the present study, $TiO_2$ scaffolds coated with one layer of 2% alginate displayed a microstructure suitable for their use as scaffold for three-dimensional cell growth.

Although a few pores remained blocked right after the coating process, almost all pores were unblocked after 7 days of Incubation at 37° C. due to biodegradability properties of alginate, thus providing opening windows for cells to penetrate and migrate into the structure. No differences on cell viability were observed between coated and uncoated $TiO_2$ scaffolds. A burst release of P2 during the first hours of incubation was found, followed by progressive and sustained release during the 21-days period, following the same pattern as in alginate hydrogels alone.

$TiO_2$ scaffolds provided an appropriate surface for osteoblasts to adhere, migrate and proliferate. Although the amount of cells into alginate-coated $TiO_2$ scaffolds was lower than in uncoated $TiO_2$ scaffolds, scaffolds coated with alginate supported cell progression and differentiation. These results are in accordance with previous studies reporting that the alginate is an inert substrate for cell attachment and that synthetic peptides rich in proline sequences increase properties for cell attachment of the alginate hydrogel. Thus, although not significantly, $TiO_2$ scaffolds coated with 2% alginate containing synthetic peptide 2 showed a trend to improve cell attachment (+32%) after 7 days compared to alginate-coated $TiO_2$ scaffolds.

It has been reported that biomaterial composition regulates cell attachment and cytoskeletal organization with long-term effects on osteoblast cell maturation and mineralization. In accordance to the efficiency in cell attachment observed by SEM and DNA quantification onto the different groups, Itgb1 mRNA levels were decreased in cells growing on alginate-coated $TiO_2$ scaffolds compared to those growing on uncoated scaffolds. Further, Itgb3 and Fn1 mRNA levels (which are highly expressed at early stages of osteogenesis and reduced through the cellular maturation process) were significantly increased in cells growing into alginate-coated $TiO_2$ scaffolds compared to the uncoated scaffolds after 21 days of culture. Moreover, expression of Itga8, an integrin that plays a role during the mineralization stage through the binding to osteopontin, was induced by P2-alginate-coated scaffolds compared to alginate-coated scaffolds, suggesting that P2 might influence mineralization processes. Integrins are not only involved in the attachment of cells to the material surface but also mediate signal transduction pathways inducing bone formation and mineralization. Interestingly, expression of genes like Itgb3, Fn1, Coll-I and Osx that are related to early stages of osteoblast differentiation, and which are normally upregulated at short term and downregulated thereafter, were increased in the later time point studied (21 days) in cells grown into alginate-coated $TiO_2$ scaffolds compared to cells growing on uncoated scaffolds. It is possible that the temporal sequence of early markers related to osteoblast differentiation varies when MC3T3-E1 cells are growing on uncoated scaffolds or on alginate-coated scaffolds, so that cells growing onto alginate-coated surfaces showed an improved cell differentiation over proliferation compared to uncoated $TiO_2$ scaffolds, probably due to the initial difficulties of cell adhesion onto the alginate. Although alginate coating seems to impair cell adhesion and proliferation on the scaffolds, the acquisition of a mature and organized matrix (ECM) competent for mineralization was confirmed by a marked increase in Alp and Bsp mRNA levels from day 7 to 21 days for any of the groups. Once the synthesis, organization and maturation of the ECM has finalized, Oc expression is upregulated leading to mineralization. The results showed a slight increase in Oc mRNA levels after 21 days of culture, therefore, it can be concluded that cells were just at the beginning of the mineralization process. Moreover, in accordance to our results with gene expression levels of Opn and Bsp, the increased relation Bsp/Opn mRNA in osteoblastic cells could be indicative for the stimulation of ECM mineralization, as previously reported with MC3T3-E1 cells seeded on uncoated $TiO_2$ scaffolds.

The addition of P2 to alginate improved the properties for cell proliferation and differentiation compared to alginate-coated scaffolds, as it can be appreciated by the amount of cells measured by DNA content and the higher expression levels of Bmp2, Coll-I and Il-6. So far the synthetic peptides rich in polyproline sequences have repetitively shown an increase in osteocalcin mRNA levels, both in vitro and in in vivo studies where titanium implants were coated with the peptide, and further when loaded into an alginate hydrogel for their use as a carrier for local delivery. Thus, taken together, this allows us to suggest that P2-alginate-coated scaffolds would promote higher cell differentiation and mineralization in an in vivo environment.

Conclusion

In conclusion, the results demonstrate that alginate-coated $TiO_2$ scaffolds can act as a matrix for delivery of biologically active substances, such as a synthetic peptide rich in proline sequences inducing osteoblast cell differentiation. The combination of the physical and osteoconductive properties of $TiO_2$ scaffolds with osteogenic effects of a biologically active substance, such as a synthetic proline-rich peptides, on bone formation and mineralization may represent a new strategy for bone tissue regeneration in load-bearing applications.

Example 3

Fabrication of $TiO_2$ Scaffolds Coated with Chitosan Gel Containing P2

The porous $TiO_2$ scaffolds were produced by polymer sponge replication as previously described by (Tiainen H et al., 2010), with a size of 9 mm of diameter and 8 mm high. Then, scaffolds were coated with one layer of 2% chitosan at pH 5.5 with or without P2 (SEQ ID NO 1). Chitosan is the deacetylated derivative of chitin, a natural component of shrimp and crab shells. It is a biocompatible, pH-dependent cationic polymer, which is soluble in water up to pH 6.2. Briefly, $TiO_2$ scaffolds were submerged into solution with or without P2 under agitation at 100 rpm on an orbital shaker (IKA Vibrax VXR basic, Staufen, Germany) for 1 h at room temperature. Scaffolds were then centrifuged at 252×g for 1 min. Samples were immersed into an aqueous solution having of pH 8.0 to allow gelation. Basification of chitosan aqueous solutions above this pH leads to the formation of a hydrated gel-like precipitate. Phase separation ensues from the neutralization of chitosan amine groups and the consequent elimination of repulsive interchain electrostatic forces, which subsequently allow for extensive hydrogen bonding and hydrophobic interactions between chains. Scaffolds were then rinsed with $dH_2O$ to remove the excess.

Finally, samples were let to dry overnight at room temperature.

Example 4

Fabrication of $TiO_2$ Scaffolds Coated with Pluronic Gel Containing P2

The porous $TiO_2$ scaffolds were produced by polymer sponge replication as previously described by (Tiainen H et al., 2010), with a size of 9 mm of diameter and 8 mm high. Then, scaffolds were coated with one layer of 20% Poloxamer 407 (Pluronic® F127) with or without P2 (SEQ ID NO 1). $TiO_2$ scaffolds were submerged into solution with or without P2 (SEQ ID NO 1) under agitation at 100 rpm on an orbital shaker (IKA Vibrax VXR basic, Staufen, Germany) for 1 h at 10° C. Scaffolds were then centrifuged at 252×g for 1 min at 10*C. Samples were then placed at 37° C. to allow gelation.

Example 5

Fabrication of $TiO_2$ Scaffolds Coated with Poly(Acrylic Acid) (PAA) Gel Containing P2

The porous $TiO_2$ scaffolds were produced by polymer sponge replication as previously described by (Tiainen H et al., 2010), with a size of 9 mm of diameter and 8 mm high. Then, scaffolds were coated with one layer of 3% high molecular weight poly(acrylic acid) (PAA) with or without P2 (SEQ ID NO 1). PAA is a bioadhesive polymer. $TiO_2$ scaffolds were submerged into the PAA solution with or without P2 (SEQ ID NO 1) under agitation at 100 rpm on an orbital shaker (IKA Vibrax VXR basic, Staufen, Germany) for 1 h at 4° C. Scaffolds were then centrifuged at 252×g for 1 min at 4° C. Samples were then placed at 37° C. to allow gelation.

Example 6

Fabrication of $TiO_2$ Scaffolds Coated with Methylcellulose and Hydroxypropyl Methylcellulose (HPMC) Hydrogel Containing P2

The porous $TiO_2$ scaffolds were produced by polymer sponge replication as previously described by (Tiainen H et al., 2010), with a size of 9 mm of diameter and 8 mm high. Then, scaffolds were coated with one layer of 8% methylcellulose and hydroxypropyl methylcellulose (HPMC) and 1 wt % NaCl with or without P2 (SEQ ID NO 1) $TiO_2$ scaffolds were then submerged into solution with or without P2 (SEQ ID NO 1) under agitation at 100 rpm on an orbital shaker (IKA Vibrax VXR basic, Staufen, Germany) for 1 h at 10° C. Scaffolds were then centrifuged at 252×g for 1 min at 10° C. Samples were then placed at 37° C. to allow gelation.

Example 7

Fabrication of $TiO_2$ Scaffolds Coated with Poly(Acrylic Acid) (PAA)-g-Poloxamer Gel Containing P2

The porous $TiO_2$ scaffolds were produced by polymer sponge replication as previously described by (Tiainen H et al., 2010), with a size of 9 mm of diameter and 8 mm high. Then, scaffolds were coated with one layer of 2.5% PAA-g-poloxamer graft copolymers with or without P2 (SEQ ID NO 1). $TiO_2$ scaffolds were submerged into solution with or without P2 (SEQ ID NO 1) under agitation at 100 rpm on an orbital shaker (IKA Vibrax VXR basic, Staufen, Germany) for 1 h at 3° C. at pH 7.4. Scaffolds were then centrifuged at 252×g for 1 min at 3° C. Samples were placed at 37° C. to allow gelation.

Example 8

Fabrication of $TiO_2$ Scaffolds Coated with PEO and P(EO-Co-PO) Gel Containing P2

The porous $TiO_2$ scaffolds were produced by polymer sponge replication as previously described by (Tiainen H et al., 2010), with a size of 9 mm of diameter and 8 mm high. Then, scaffolds were coated with one layer of aqueous solution of PEO (5 ml, 5% w/v) or P(EO-co-PO) containing photoiniator 4-benzoylbenzyl) trimethylammoniumchloride (BBTMAC) (5% of the polymer mass was poured into a $TiO_2$ scaffold with or without P2 (SEQ ID NO 1). $TiO_2$ scaffolds were then be submerged into solution with or without P2 (SEQ ID NO 1) under agitation at 100 rpm on an orbital shaker (IKA Vibrax VXR basic, Staufen, Germany) for 0.5 h at room temperature. Scaffolds were then centrifuged at 252×g for 1 min at room temperature. Samples were then UV irradiated in a Dimax light curing system, model 5000 Flood, for 2 minutes to allow gelation at 200-400 nm.

Example 9

Preparation of an Alginate Coated Titanium Dioxide Scaffold for Local Delivery of Simvastatin 1. Summary Highly porous titanium dioxide ($TiO_2$) scaffolds were submerged into simvastatin (SIM) (i.e. a biologically active substance) containing alginate solution. Microstructure of scaffolds, visualized by scanning electron microscopy and Periodic acid-Schiff staining, revealed an evenly distributed alginate layer covering the surface of $TiO_2$ scaffold struts. Progressive and sustained SIM release was observed for up to 19 days. No cytotoxic effects on osteoblasts were observed by scaffolds with SIM when compared to scaffolds without SIM. Expression of osteoblast markers (collagen type I alpha 1, alkaline phosphatase, osteoprotegerin, osteocalcin and vascular endothelial growth factor A) was quantified using real-time RT-PCR. Secretion of osteoprotegerin, vascular endothelial growth factor A and osteocalcin was analysed by multiplex immunoassay (Luminex). The relative expression and secretion of osteocalcin was significantly increased by cells cultured on scaffolds with 10 µM SIM when compared to scaffolds without SIM after 21 days. In addition, secretion of vascular endothelial growth factor A was significantly enhanced from cells cultured on scaffolds with both 10 nM and 10 µM SIM when compared to scaffolds without SIM at day 21. In conclusion, the results indicate that SIM-coated $TiO_2$ scaffolds can support a sustained release SIM and induce osteoblast differentiation. The combination of the physical properties of $TiO_2$ scaffolds with the osteogenic effect of SIM may represent a new strategy for bone regeneration in defects where immediate load is wanted or unavailable. This example is therefore an exemplary embodiment demonstrating that the alginate coated titanium dioxide scaffolds of the present document can be used to deliver a biologically active substance, such as for providing a positive effect on osteoblast cell growth.

2. Materials and Methods 2.1. Fabrication of $TiO_2$ Scaffolds Coated with Alginate Hydrogel Containing SIM Porous $TiO_2$ scaffolds, with a size of 9 mm in diameter and 8 mm in height, were produced by polymer sponge replication as previously described (Tiainen H et al. 2010). In short, polymer foams were impregnated with $TiO_2$ slurry, dried and subsequently sintered at 1500° C. for 40 hours. A second layer of $TiO_2$ slurry was added to the scaffolds and re-sintered at the same temperature as previously mentioned. Total surface area of the scaffolds, determined by micro-computed tomography (1172 micro-CT imaging system, Skyscan, Kontich, Belgium), was 20.295 $cm^2$. Produced scaffolds were sterilized by autoclaving at 121° C. for 20 minutes. SIM (Krebs Biochemicals & Industries, Andhra Pradesh, India) was dissolved in 100% ethanol before being added to 2% (w/v) Pronova UP LVG sodium alginate (FMC BioPolymer, Sandvika, Norway) in milliQ water at desired concentrations to create SIM containing alginate-coated $TiO_2$ scaffolds. Alginate solution with or without SIM was sterilized before use with a 0.22 µm pore size syringe filter (TPP Techno Plastic Products AG, Trasadingen, Switzerland).

The $TiO_2$ scaffolds were submerged into alginate solution with or without SIM under agitation at 100 rpm on an orbital shaker for 1 hour at room temperature followed by centrifugation at 300×g for 1 minute to remove the excess alginate solution. Subsequently, scaffolds were immersed into 50 mM $CaCl_2$ with or without SIM under agitation at 100 rpm on an orbital shaker for 1 hour. Alginate-coated scaffolds were finally rinsed with milliQ water to remove the excess $CaCl_2$ and air-dried overnight. Scaffolds coated with 2% alginate hydrogel without SIM, were used as a control group.

2.2. Characterization of $TiO_2$ Scaffolds Coated with Alginate Hydrogel Containing SIM The alginate-coated scaffolds were gold-sputtered (Cressington sputter coater 108 auto, Cressington Scientific Instruments, Watford, England) and their microstructure was visualized by scanning electron microscopy (SEM) (TM-1000, Hitachi High-Technologies, Tokyo, Japan) with back-scattered secondary ions at 15 kV accelerating voltage. Alginate coating was further assessed by Periodic acid-Schiff (PAS) staining. In brief, scaffolds were washed with milliQ water and oxidized in 1% periodic acid solution (Sigma-Aldrich, St. Louis, Mo., USA) for 5 minutes. Then, the scaffolds were rinsed with milliQ water and placed into Schiff reagent (Sigma-Aldrich, St. Louis, Mo., USA) for 15 minutes. Finally, the scaffolds were soaked in lukewarm tap water for 5 minutes and subsequently photographed (Nikon digital camera D700, Sendai Nikon Corporation, Miyagi, Japan).

2.3. Quantification of SIM Release from Alginate-Coated $TiO_2$ Scaffolds

Alginate-coated scaffolds and SIM (2.4 mM, 0.6 mM) containing alginate-coated scaffolds were kept at 37° C. in 1 ml milliQ water in a humidified atmosphere for up to 19 days to determine the release profile of SIM. At prefixed time points (0.25 days, 2 days, 4 days, 6 days, 8 days, 10 days, 13 days, 15 days, 17 days, 19 days) the milliQ water was replaced, and the amount of SIM released was quantified using UV-Vis spectrophotometer (PerkinElmer Lambda 25 UV/Vis System, PerkinElmer, Waltham, Mass., USA). The sample absorbance at a wavelength of 238 nm was analyzed and the relative absorbance units were correlated with the amount of SIM released for each time point using a linear standard curve. Absorbance values from scaffolds coated with alginate without SIM were used as control to subtract background values obtained from alginate degradation products. The experiment was performed in triplicate.

2.4. Cell Culture and Seeding of Primary Human Osteoblasts

Primary human osteoblasts (Cambrex Bio Science, Walkersville, Md., USA) from three donors, two from femur (16- and 10-year-old males) and one from tibia (41-year-old male) were cultured in osteoblast culture medium supplemented with 10% fetal bovine serum, 0.1% gentamicin sulfate and amphotericin-B antibiotics and 0.1% ascorbic acid (Lonza Walkersville, Md., USA) in 75 cm2 culture flasks at 37° C. in a humidified atmosphere of 5% CO2. Cells from passages 7-9 were seeded on scaffolds at a density of 400.000 cells/ml. In order to ensure a homogenous cell distribution throughout the scaffold, an agitated seeding method was used (Takahshi et al 2003). Scaffolds soaked with culture medium were placed in 48-well culture plates. After adding 1 ml of cell suspension to the scaffolds, plates were agitated on an orbital shaker at 200 rpm for 6 hours at 37° C. Cell-seeded scaffolds were transferred to new culture plates in 1 ml culture medium and maintained at 37° C. in a humidified atmosphere of 5% $CO_2$ for up to 21 days. The culture medium was replaced every other day. Collected medium was saved for use in cytotoxicity, alkaline phosphatase (ALP) activity and protein expression assays. Scaffolds were harvested after 7, 14 and 21 days of culture for use in real-time RT-PCR and immunocytochemistry.

2.5. Cytotoxicity Assay

The cytotoxicity of the SIM containing scaffolds was estimated based on the activity of the cytostolic enzyme lactate dehydrogenase (LDH) in the culture medium. The LDH activity was determined in medium collected every other day up til 14 days, according to the manufacturer's cytotoxicity detection kit instructions (Roche Diagnostics, Mannheim, Germany). 50 µl of sample was incubated with the kit reaction mixture for 30 minutes in the dark at room temperature. The absorbance of the samples was measured at 492 nm in a plate reader (Biochrom Asys Expert 96 Microplate Reader, Biochrom, Holliston, Mass., USA).

2.6. ALP Activity Assay

The ability of ALP to hydrolyze P-nitrophenyl phosphate (pNPP) substrates (Sigma-Aldrich, St. Louis, Mo., USA) into the yellow end-product, p-nitrophenol, was used to quantify the ALP activity in the culture medium after 2, 8, 14 and 21 days of culture. 25 µl of medium was taken from each sample and incubated with 100 µl pNPP solution in a 96-well plate for 30 minutes in the dark at room temperature, subsequently 50 µl of 3M NaOH was added to each well to stop the reaction. The absorbance was measured at 405 nm in a plate reader (Biochrom Asys Expert 96 Microplate Reader, Biochrom, Holliston, Mass., USA) and the ALP activity was quantified using a standard curve based on calf intestinal alkaline phosphatase (Promega, Madison, Wis., USA).

2.7. Immunoassay: Quantification of Secreted Proteins

Aliquots of the collected culture medium were up-concentrated 8-fold using a modified PES 3K centrifugal filter (VWR, Radnor, Pa., USA) according to the manufacturer's instructions. Multianalyte profiling of protein levels in the concentrated cell culture medium was performed on the Luminex 100/200 system (Luminex, Austin, Tex., USA) using xMAP technology. Acquired fluorescence data was analyzed by the xPONENT 3.1 software (Luminex, Austin, Tex., USA). The amount of osteoprotegerin (TNFRSF11B), osteocalcin (BGLAP) and vascular endothelial growth factor A (VEGFA) in the culture medium was measured using the human bone panel and human cytokine/chemokine kits (Millipore, Billerica, Mass., USA) after 2, 8, 14 and 21 days of culture. All analyses were performed according to the manufacturer's protocols.

2.8. RNA Isolation and Real-Time RT-PCR Analysis

Total RNA was isolated from cell-seeded scaffolds using the Qiagen RNA mini-kit (Qiagen, Hilden, Germany) with slight modifications to the manufacturer's protocol. Briefly, scaffolds were immersed into lysis buffer for 1 hour at 4° C. followed by agitation on an orbital shaker at 300 rpm for 10 minutes at room temperature. Subsequently, the scaffolds were discarded and the lysate buffer was sonicated (Sonics Vibracell VC130PB, CT, USA) at 2 W for 30 seconds. The remaining procedures followed the protocol provided by the manufacturer.

cDNA was synthesized with RevertAid First Strand cDNA Synthesis Kit (Fermentas, St. Leon-Rot, Germany) using oligo dT primers. Real-time PCR was performed in the CFX 384□ Real-Time System (Bio-Rad, Hercules, Calif., USA) using SsoAdvanced□ SYBR® Green Supermix. Three-step amplification (40 cycles: 5 seconds 95° C., 60 seconds 60'C, 30 seconds 72'C) was implemented. No amplification control and no template control were used. Real-time RT-PCR was done for glyceraldehyde-3-phosphate dehydrogenase (GAPDH), collagen type I alpha 1 (COL1A1), alkaline phosphatase (ALPL), osteoprotegerin (TNFRSF11B), osteocalcin (BGLAP) and vascular endothelial growth factor A (VEGFA). The primer sequences are listed in Table 4. Real-time RT-PCR data was analyzed using the efficiency corrected $\Delta\Delta CT$ method (Pfaffl et al. 2001).

TABLE 4

Primer sequences used for real-time RT-PCR assays

| Gene | Primer sequence |
|---|---|
| GAPDH | Left: CTCTGCTCCTCCTGTTCGAC (SEQ ID NO: 37)<br>Right: ACGACCAAATCCGTTGACTC (SEQ ID NO: 38) |
| COL1A1 | Left: CATCTCCCCTTCGTTTTTGA (SEQ ID NO: 39)<br>Right: CCAAATCCGATGTTTCTGCT (SEQ ID NO: 40) |
| ALPL | Left: GACAAGAAGCCCTTCACTGC (SEQ ID NO: 41)<br>Right: AGACTGCGCCTGGTAGTTGT (SEQ ID NO: 42) |
| TNFRSF11B | Left: TGGGAGCAGAAGACATTGAA (SEQ ID NO: 43)<br>Right: GTGTCTTGGTCGCCATTTTT (SEQ ID NO: 44) |
| VEGFA | Left: TCTTCAAGCCATCCTGTGTG (SEQ ID NO: 45)<br>Right: ATCTGCATGGTGATGTTGGA (SEQ ID NO: 46) |
| BGLAP | Left: GCAAGTAGCGCCAATCTAGG (SEQ ID NO: 47)<br>Right: GCTTCACCCTCGAAATGGTA (SEQ ID NO: 48) |

2.9. Immunocytochemistry and Confocal Laser Scanning Microscopy

After 21 days of culture, scaffolds were cut in half by use of a scalpel and fixed in 4% paraformaldehyde (PFA)/4.6% D-Mannitol for 15 minutes and subsequently stored in 1% PFA/4.6% D-Mannitol until further processing. Fixed scaffolds were submitted to heat induced epitope retrieval by heating to 95° C. in 0.05% citraconic anhydride in milliQ water (pH 7.4) for 15 minutes, incubated with monoclonal mouse anti-human collagen type I antibody (I-8H5, MP Biomedicals, Santa Ana, Calif., USA) diluted to 1 µg/ml in 1.25% bovine serum albumin (BSA) in phosphate buffered saline (PBS) with 0.2% Triton X for 1 hour at room temperature, followed by incubation for 30 minutes at room temperature in Cy3-conjugated donkey anti-mouse IgG (Jackson ImmunoResearch, West Grove, Pa., USA) diluted in 2.5% BSA/0.05% Tween-20/PBS at a concentration of 2 mg/ml. Cell-seeded whole mount stained scaffolds were counterstained using DAPI, placed on a coverslip and covered with Dako fluorescent mounting medium (Dako, Glostrup, Denmark). Confocal laser scanning microscopy was performed on a FluoView 1000 confocal laser scanning microscope (CLSM) (Olympus, Center Valley, Pa., USA). The scaffold surfaces were visualized using the CLSM in reflection mode. Images were analyzed using ImageJ (NIH, Bethesda, Md., USA).

2.10. Statistics

The data obtained by cytotoxicity, ALP activity, gene expression and protein secretion analyses passed normality test (Shapiro-Wilk) and was compared between groups using Holm-Sidak test following a parametric one way ANOVA (SigmaPlot 12.3, Systat Software, San Jose, Calif., USA). A probability of ≤0.05 was considered significant.

Figure 14:
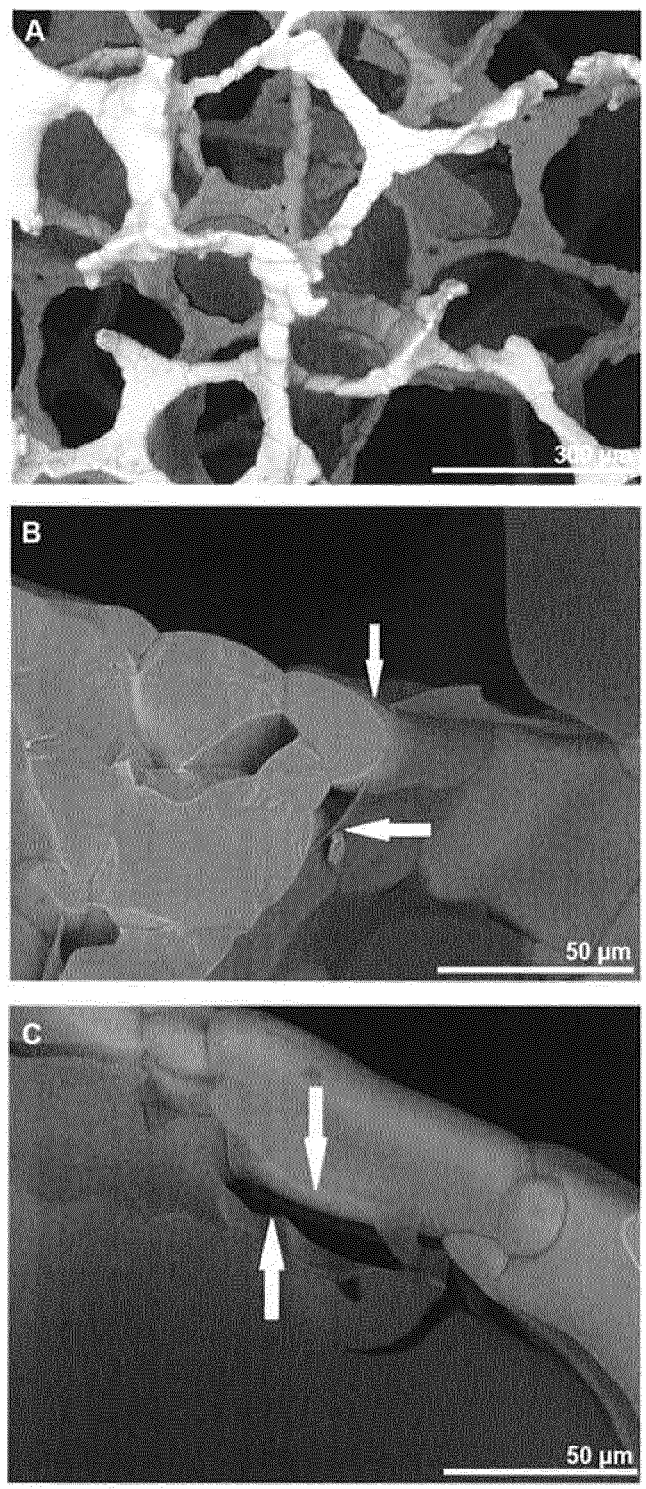
FIG. 14. Scanning electron microscope characterization of alginate-coated $TiO_2$ scaffolds. Scanning electron microscope visualization of alginate layer (arrows) coating the strut surface of $TiO_2$ scaffolds at 250× (A) and 1500× (B, C) of magnification.
Figure 15:
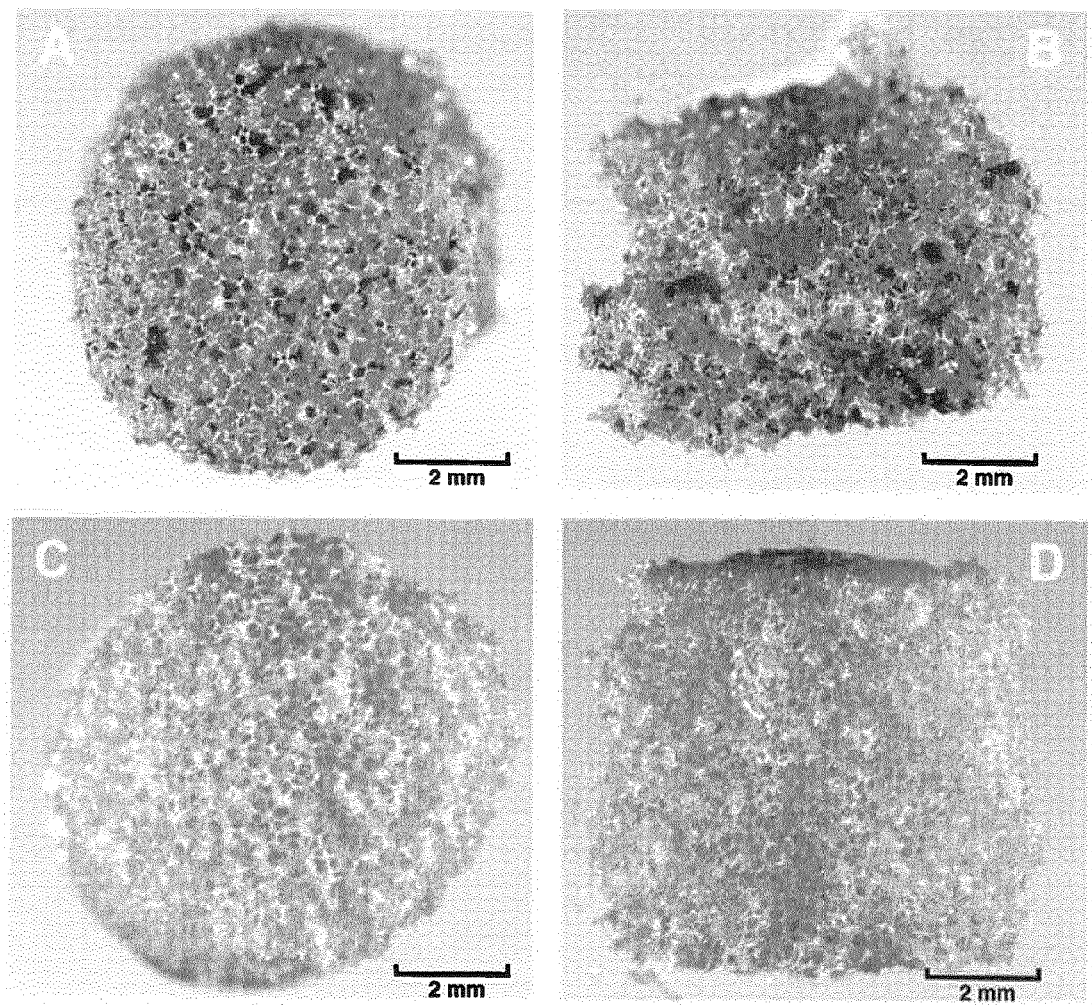
FIG. 15. Periodic acid-Schiff visualization of alginate-coated and uncoated $TiO_2$ scaffolds. Periodic acid-Schiff staining of alginate-coated (A, B) and uncoated (C, D) $TiO_2$ scaffolds. The alginate (red) is distributed throughout the scaffold as seen in the view from the top (A) and in the middle (B).

3. Results
3.1. Characterization of TiO$_2$ Scaffolds Coated with 2% Alginate Hydrogel SEM analysis of the alginate-coated scaffolds revealed that the immersion-centrifugation technique resulted in an even distribution of the alginate, coating the surface of the TiO$_2$ scaffold struts (FIG. 14; A-C). Only minor variations were seen in the distribution of the alginate, as visualized by PAS staining on the top of (FIG. 15A) and in the middle of (FIG. 15 B) the TiO$_2$ scaffold.

3.2. Simvastatin Release

Figure 16:
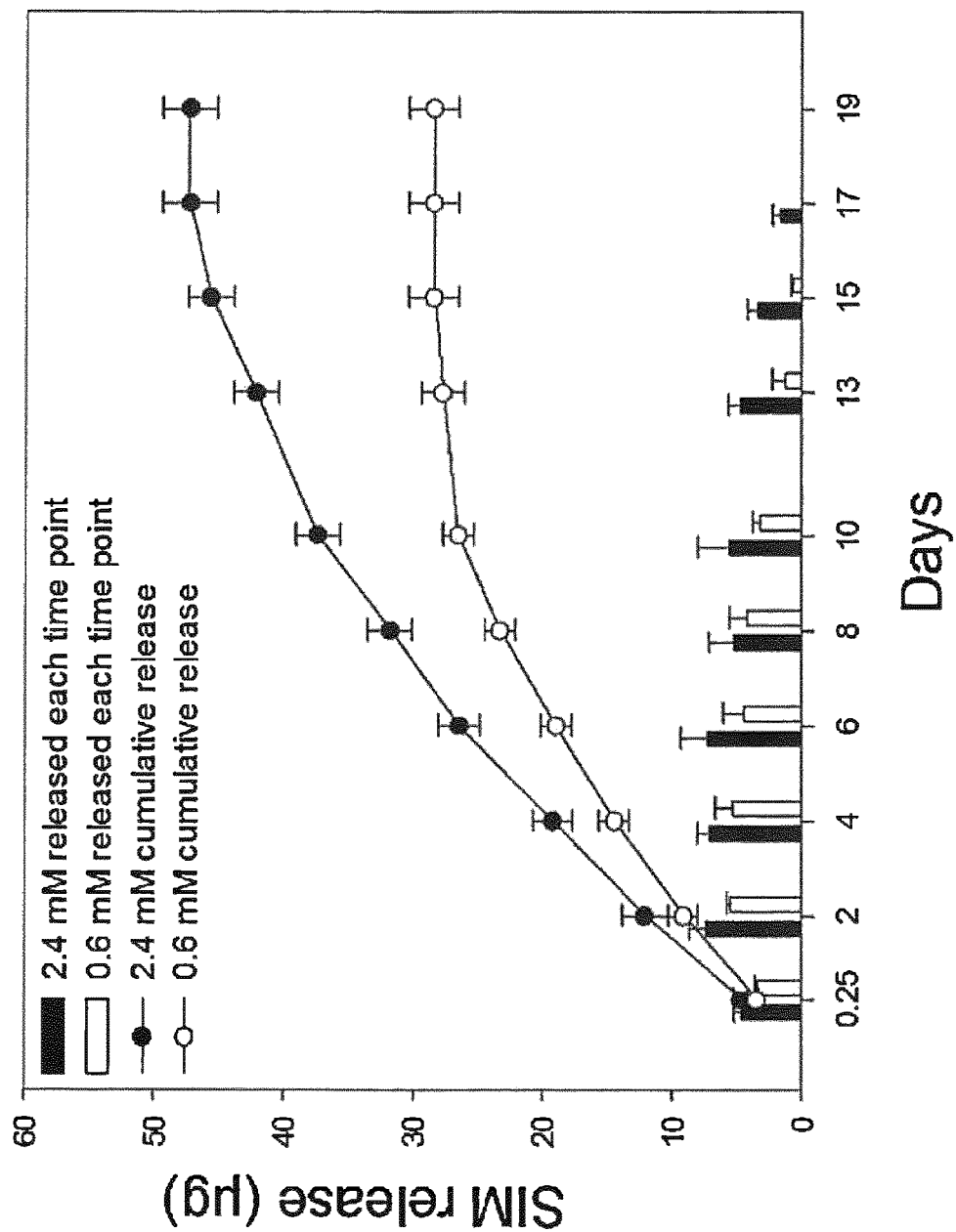
FIG. 16. Simvastatin release. Release profile of SIM from alginate-coated $TiO_2$ scaffolds containing 2.4 mM and 0.6 mM SIM after 19-day incubation at 37° C. Bar graph shows the amount of SIM released after each time point. Line graph represents cumulative amount of SIM released up to 19 days. Values represent the mean±SD.

The release of SIM was investigated for scaffolds with 2.4 mM and 0.6 mM SIM. A slow sustained release of SIM was detected for both concentrations. However, scaffolds with 2.4 mM SIM resulted, in a longer, 17-day release period compared to the 15-day release seen for scaffolds with 0.6 mM SIM (FIG. 16). The cumulative release suggested that SIM remained entrapped in the alginate even after 19 days of incubation. Continued release could not be detected as the concentration after this point was below the detection limit.

3.3. LDH Activity

Figure 17A:
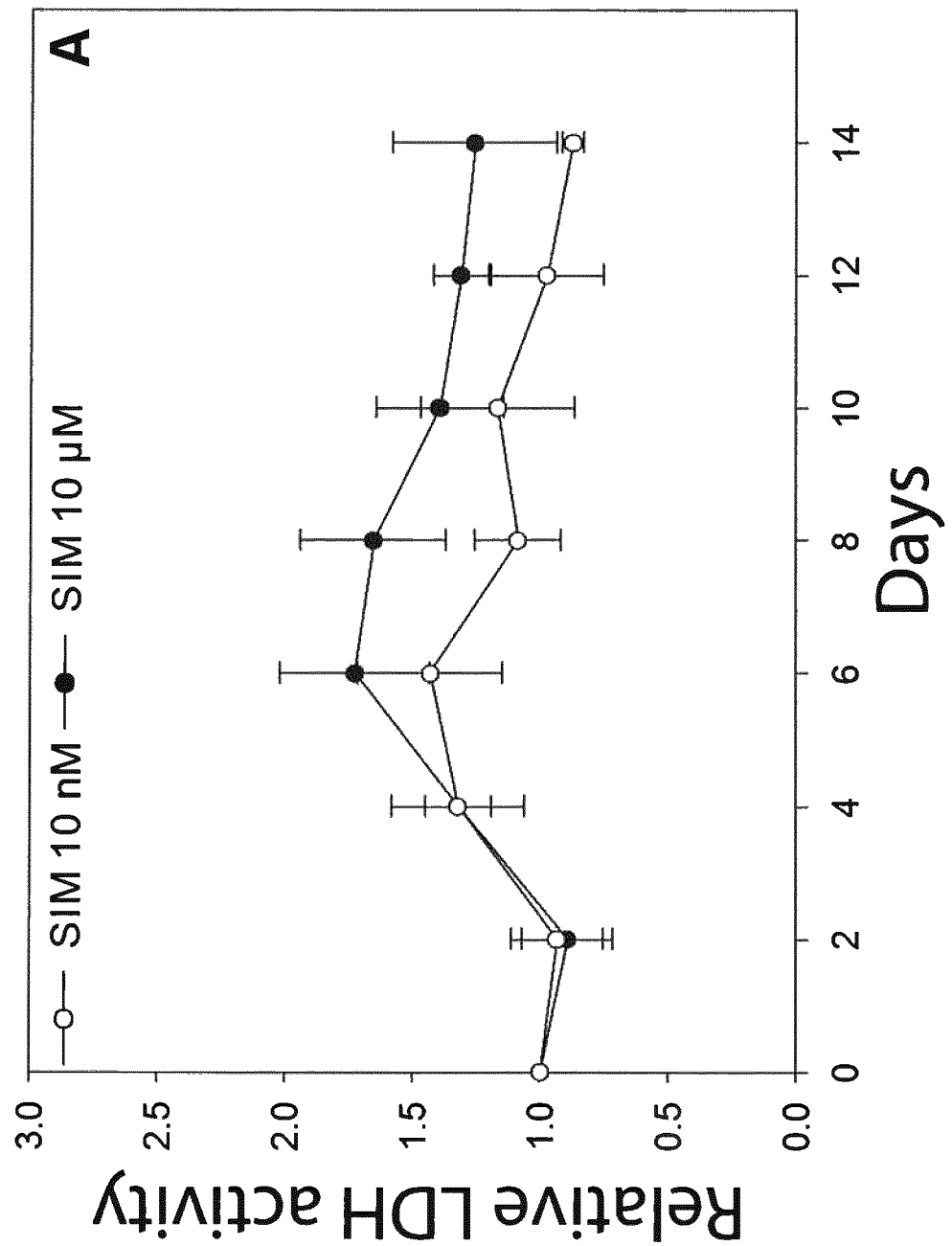
FIG. 17A-C. Lactate dehydrogenase activity assay. LDH activity in culture medium from scaffolds with 10 nM and 10 μM SIM is shown compared to scaffolds without SIM for donor 1 (A), donor 2 (B) and donor 3 (C) measured every other day up til 14 days. Neither of the SIM concentrations caused a significant increase in LDH activity compared to the effect of alginate-coated scaffolds without SIM. Values represent the mean ±SD.
Figure 17B:
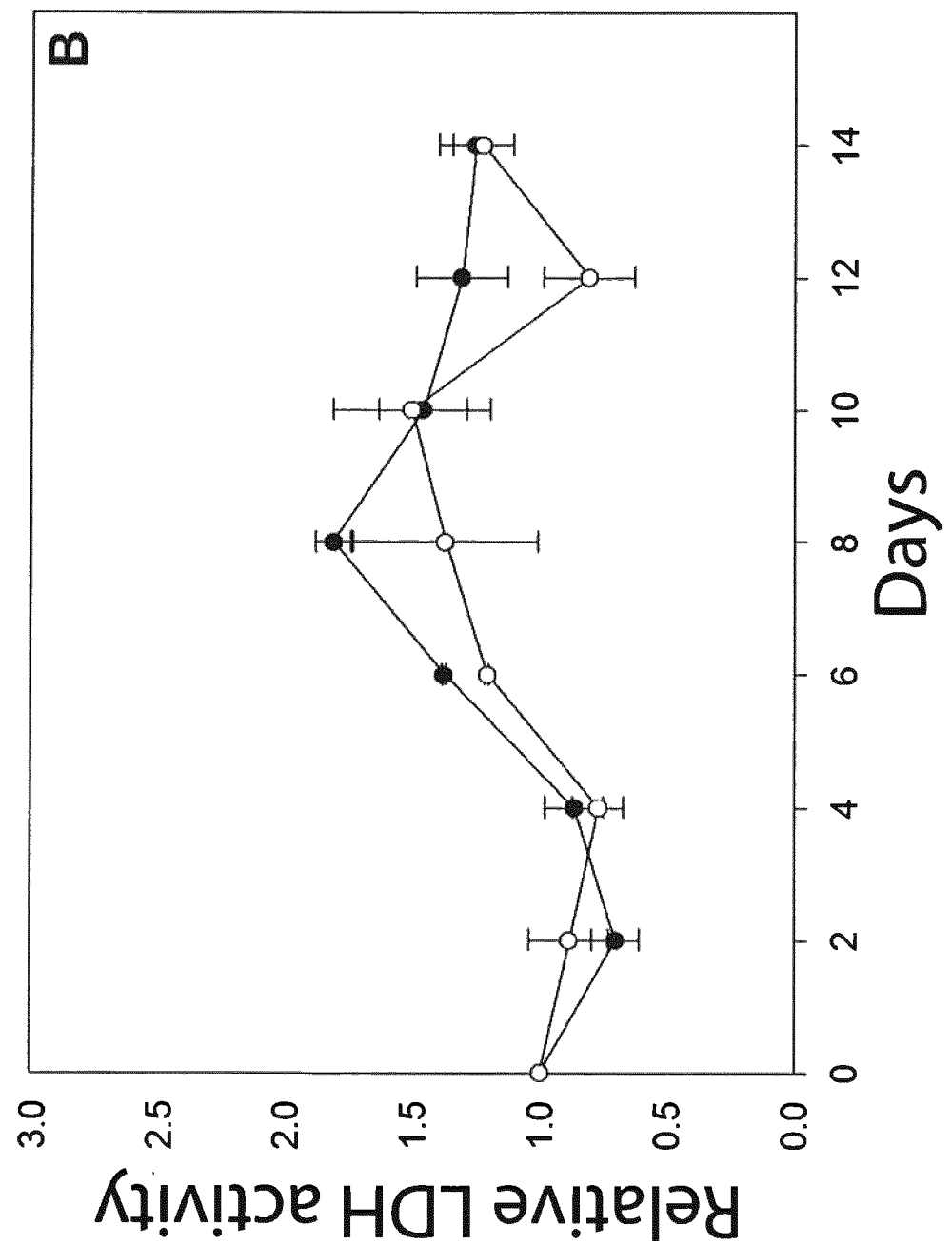
Figure 17C:
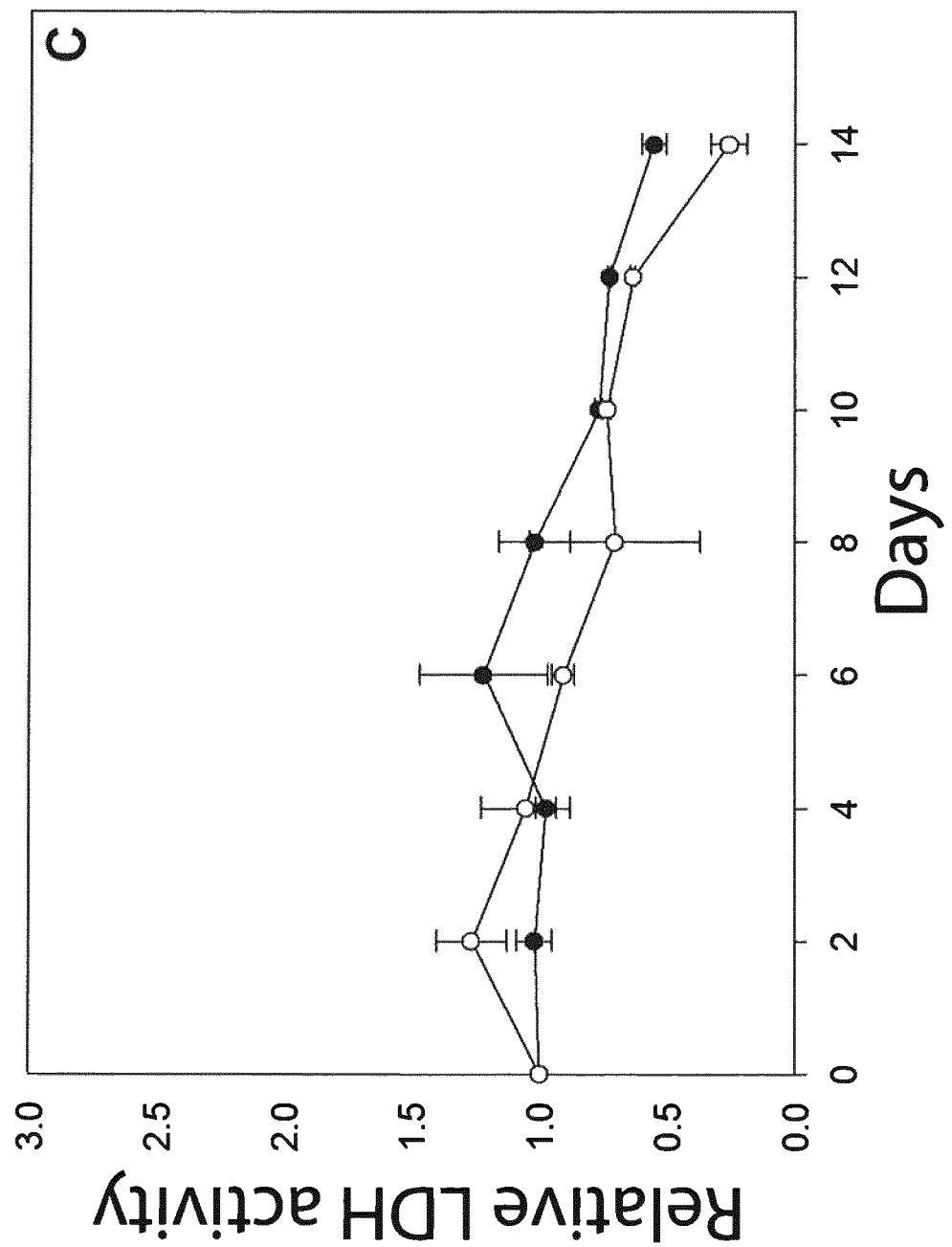

The cytotoxic effect of SIM from alginate-coated scaffolds was tested for a wide range of concentrations (2.4 mM, 0.6 mM, 24 µM, 10 µM, 1 µM, 0.1 µM, and 10 nM). SIM was found to be highly cytotoxic for osteoblasts at higher concentrations (above 10 µM), when cells were seeded on the scaffolds (data not shown). A 14-day cytotoxicity study was performed for lower concentrations of SIM (10 µM and 10 nM) to investigate the effect on osteoblast viability when exposed to SIM for a sustained time period. A higher LDH activity was generally detected in the medium from scaffolds with 10 µM SIM compared to scaffolds with 10 nM SIM throughout the 14-day period. Neither of the SIM concentrations caused a significant increase in LDH activity compared to the effect of alginate-coated scaffolds without SIM. Some variation was seen in the LDH activity profiles, indicating donor dependent differences in the cellular response to SIM (FIG. 17; A-C).

Figure 18A:
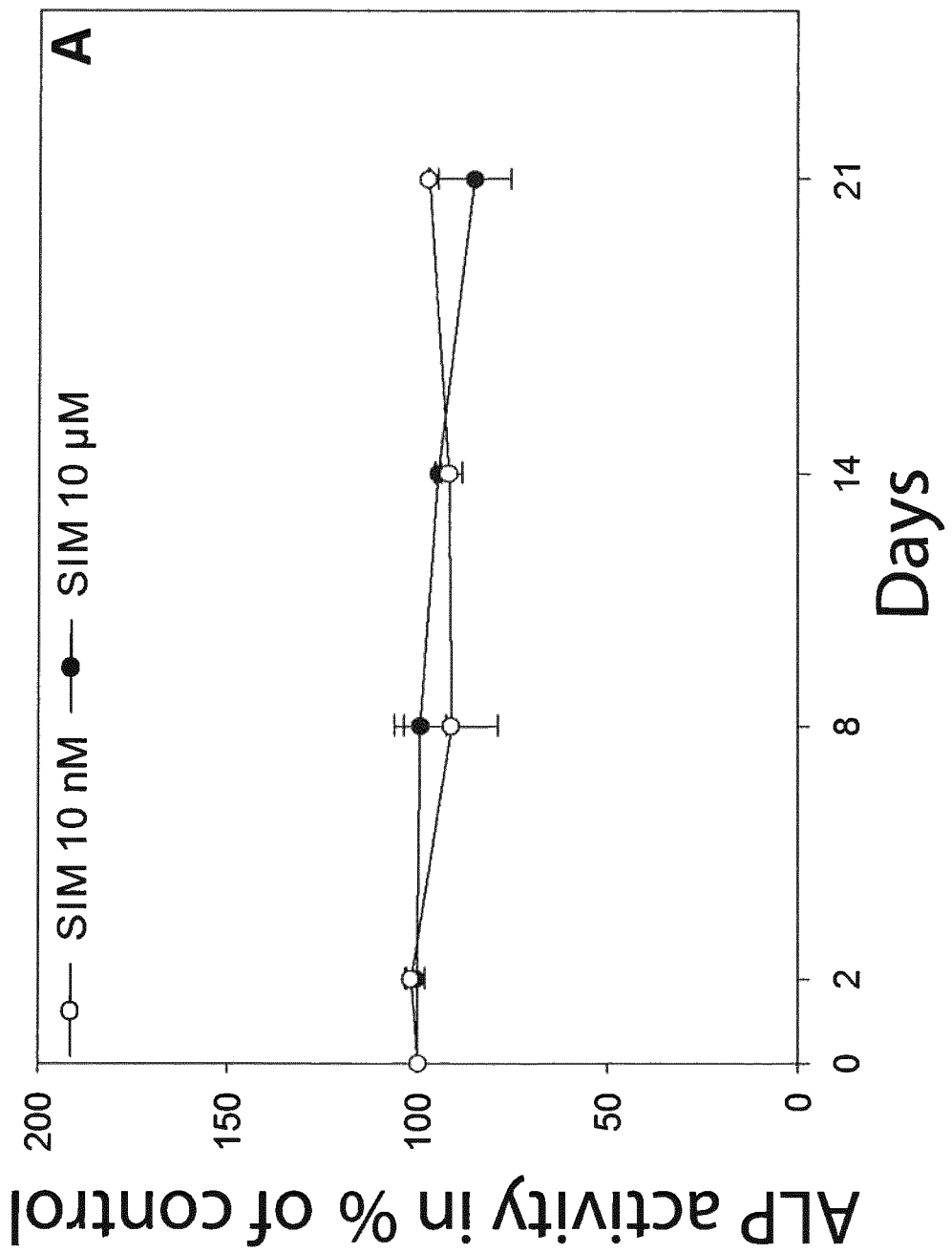
FIG. 18A-C. Alkaline phosphatase activity assay. ALP activity (y axis) in culture medium from scaffolds with 10 nM and 10 μM SIM is shown in percentage of control, scaffolds without SIM, for donor 1 (A), donor 2 (B) and donor 3 (C) at 2, 8, 14 and 21 days. ALP activity did not significantly change in the culture medium at any of the time points measured either for scaffolds with 10 nM or 10 μM SIM when compared to scaffolds without SIM. Values represent the mean ±SD.
Figure 18B:
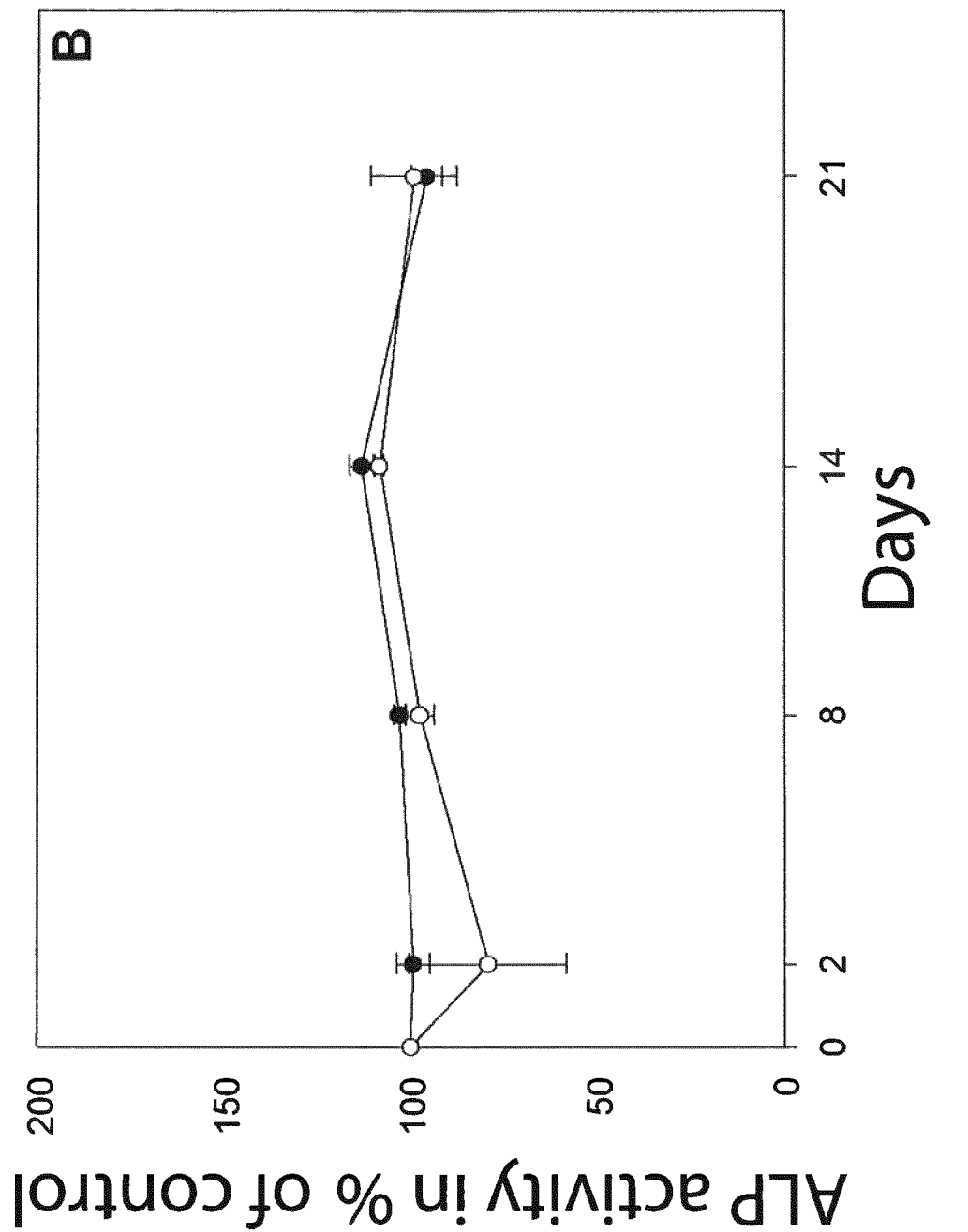
Figure 18C:
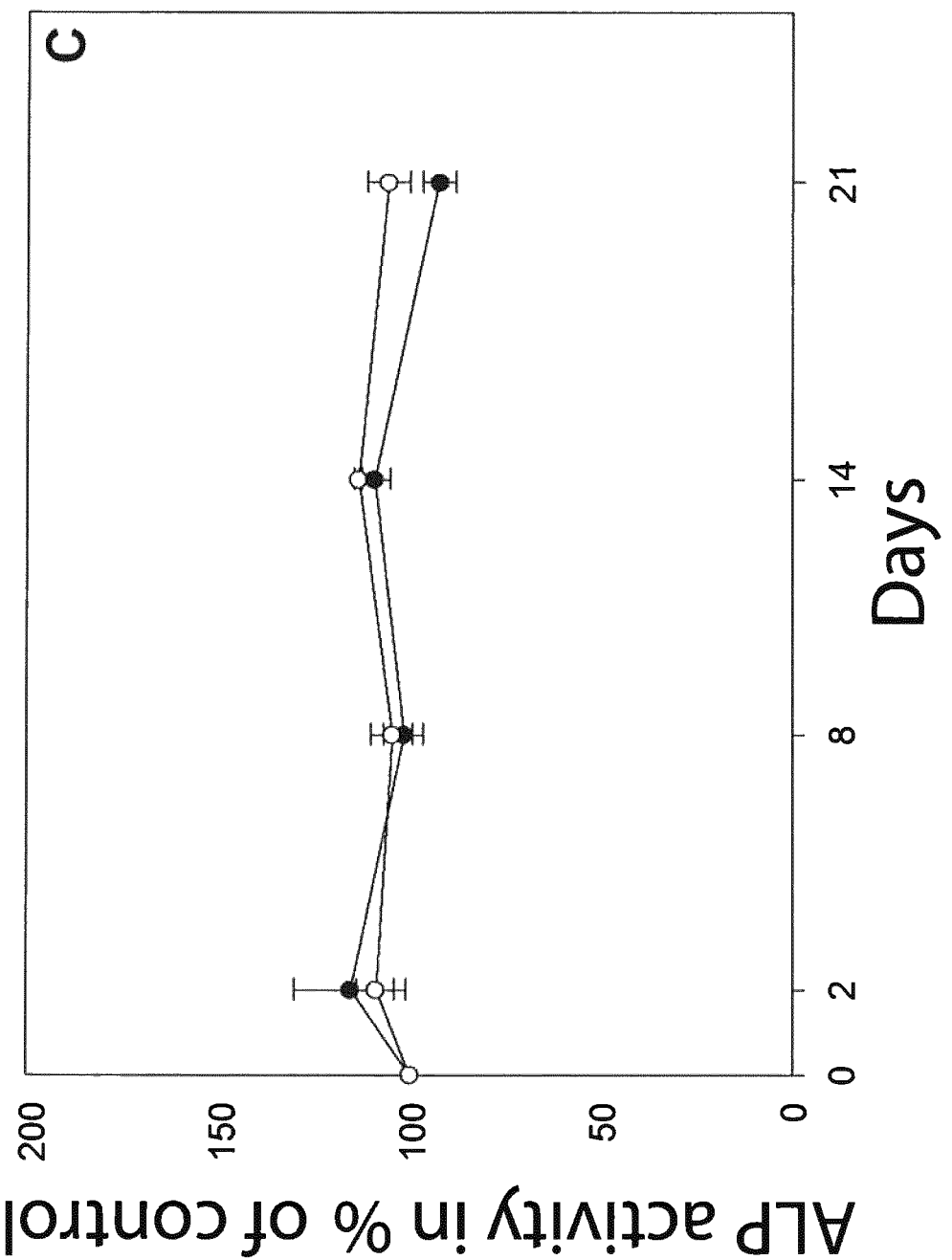

3.4. Effect of SIM Containing Alginate-Coated TiO$_2$ Scaffolds on Osteoblast Differentiation Culturing osteoblasts on SIM containing scaffolds did not significantly change the ALP activity in the culture medium at any of the time points measured either for scaffolds with 10 nM or 10 µM SIM when compared to scaffolds without SIM (FIG. 18; A-C).

Figure 19A:
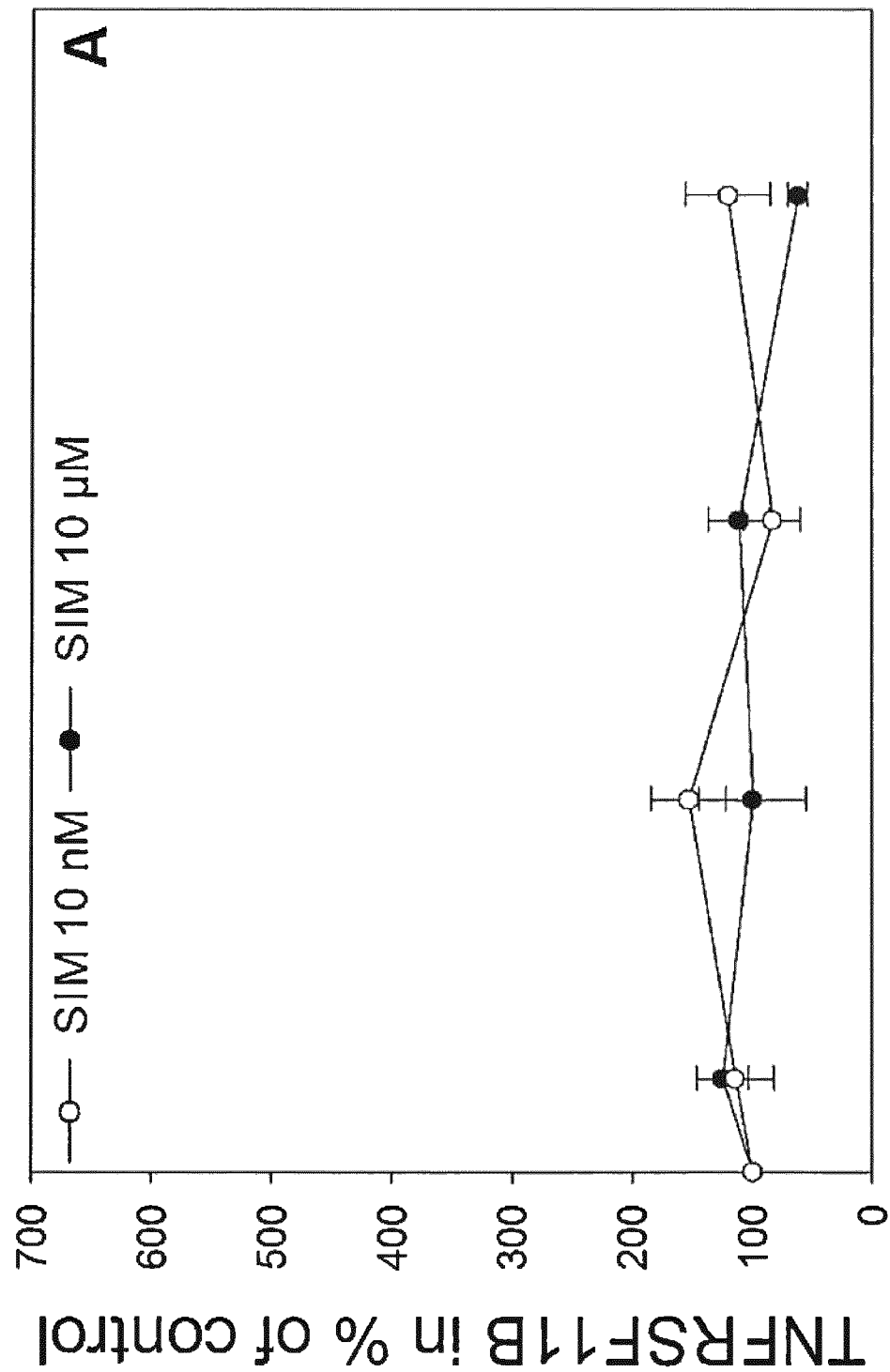
FIG. 19A-C. Immunoassay: Quantification of secreted proteins. Secretion of TNFRSF11B, VEGFA and BGLAP to cell culture medium from scaffolds with 10 nM and μM SIM is shown in percentage of control, scaffolds without SIM, at 2, 8, 14 and 21 days. Values represent the mean ±SD.
Figure 19B:
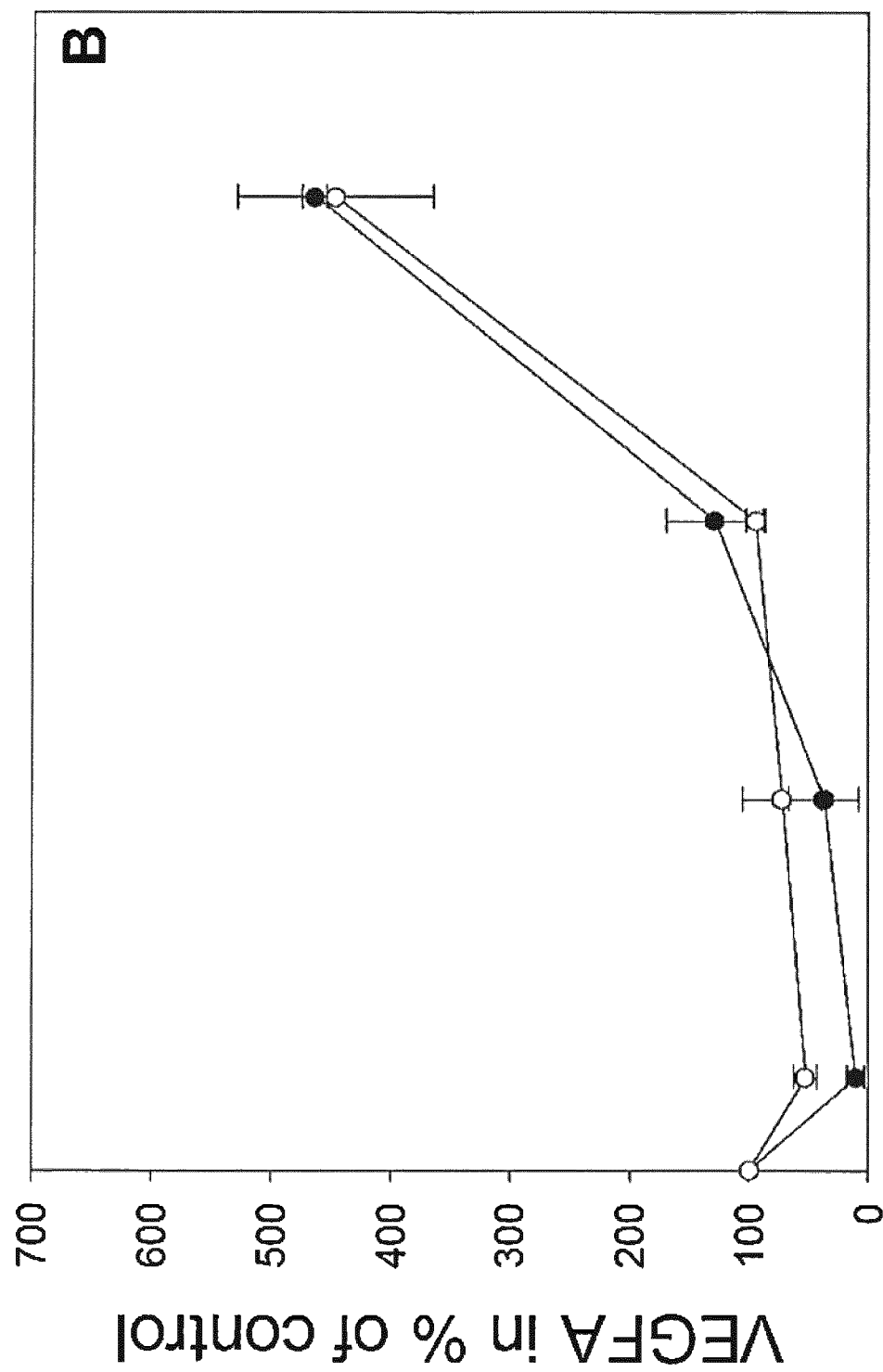
Figure 19C:
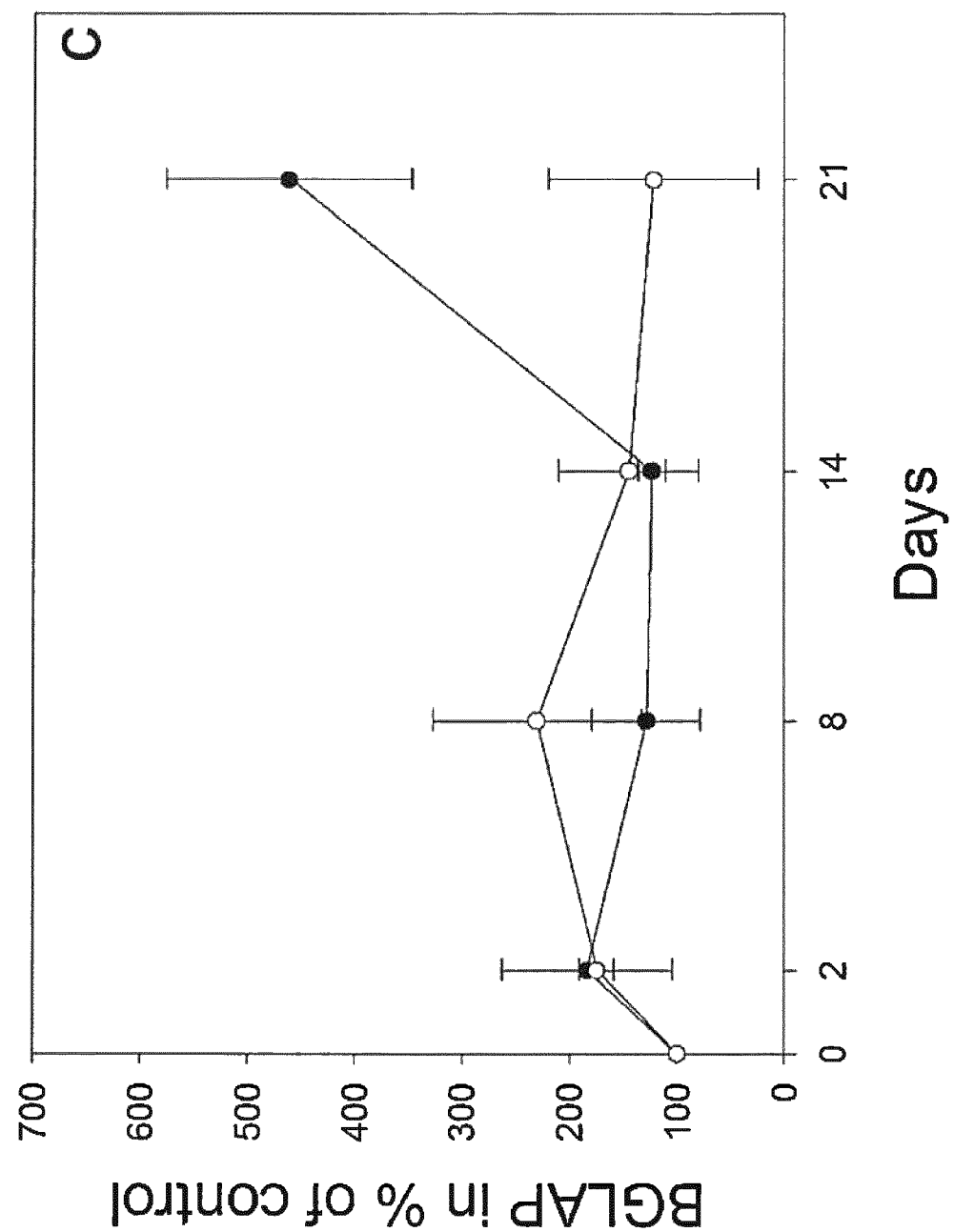

No significant differences were seen in the TNFRSF11B content of the culture medium at any time points either from scaffolds with 10 nM or 10 µM SIM when compared to scaffolds without SIM (FIG. 19A). However, the content of VEGFA in the culture medium was significantly increased from cells cultured on scaffolds with both 10 nM and 10 µM SIM when compared to scaffolds without SIM at day 21 (FIG. 19B). The secretion of BGLAP was significantly enhanced from cells on scaffolds with 10 µM SIM when compared to scaffolds without SIM, whereas no significant difference was seen for cells cultured on scaffolds with 10 nM SIM compared to scaffolds without SIM after 21 days of culture (FIG. 19C).

Figure 20:
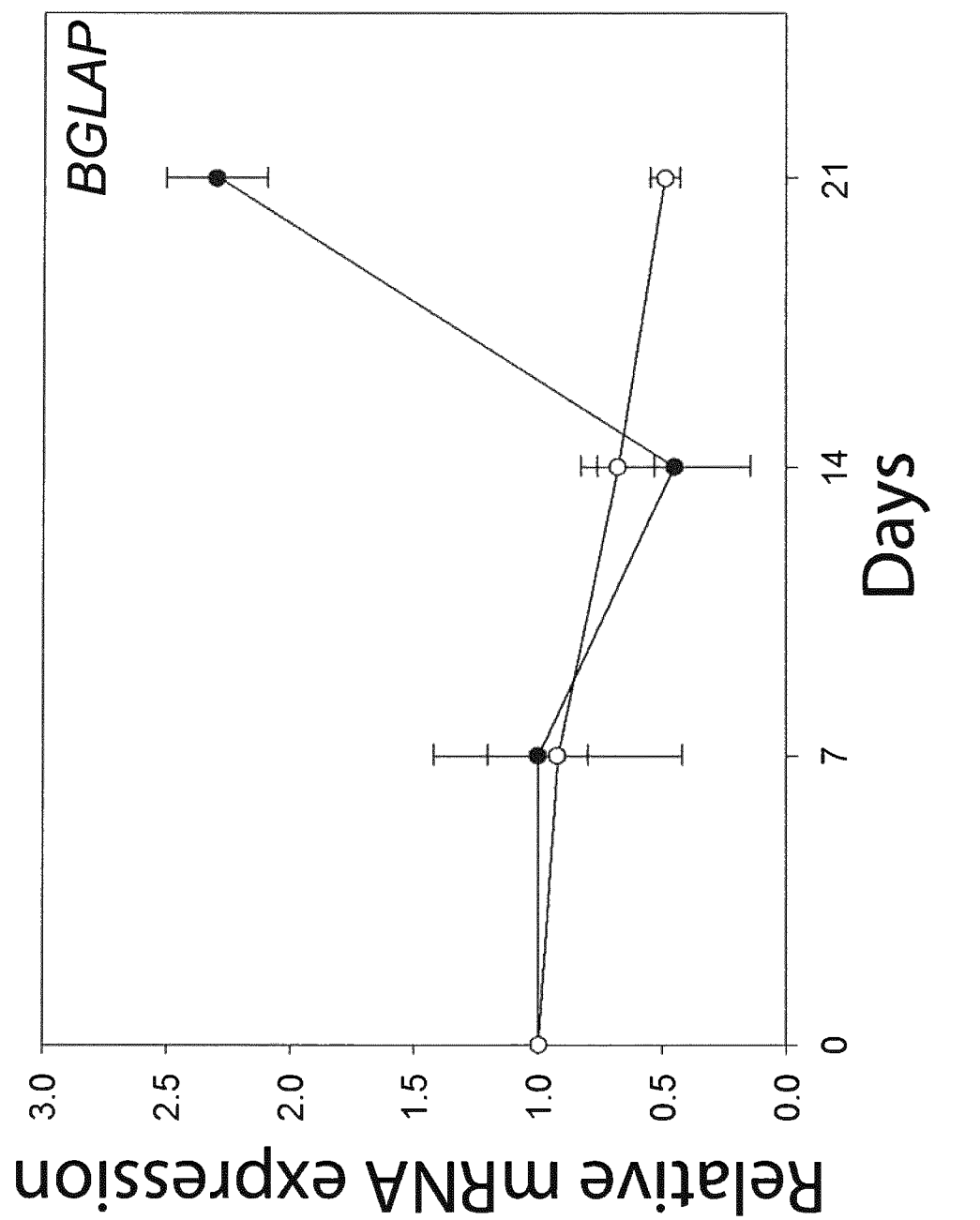
FIG. 20. Real-time RT-PCR analysis. Relative mRNA expression levels for BGLAP are shown in cells cultured on scaffolds with 10 nM and 10 μM SIM compared to scaffolds without SIM and normalized to reference gene GAPDH at 7, 14 and 21 days. Values represent the mean ±SD.
Figure 21A:
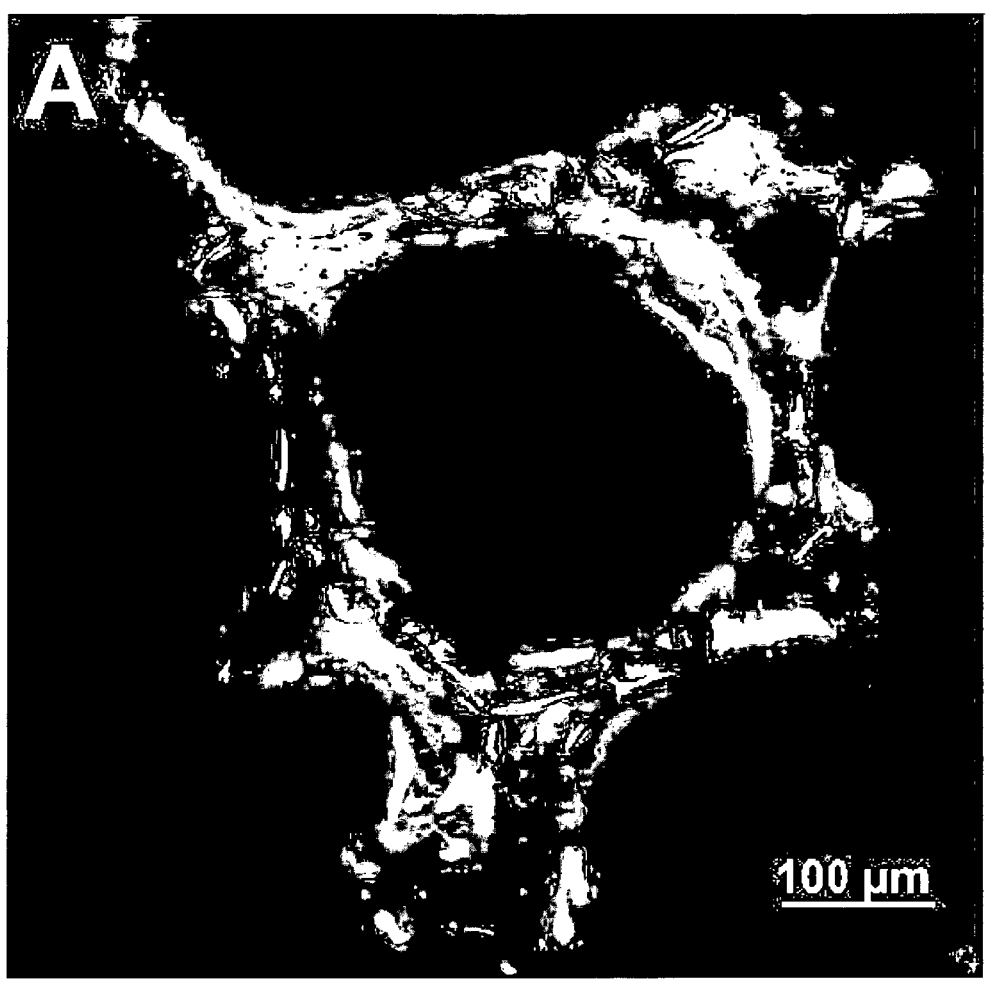
FIG. 21A-C. Confocal laser scanning microscopy visualization of type I collagen deposition in alginate-coated $TiO_2$ scaffolds with or without simvastatin. Fluorescence immunocytochemlcal analysis of type I collagen in primary human osteoblasts cultured on alginate-coated TiO2 scaffolds. Type I collagen is detected in the majority of the cells cultured on scaffolds with 10 nM SIM (A), 10 μM SIM (B) and without SIM (C). Extracellular collagen fibrils are only seen in scaffold without SIM (C). Type I collagen, DNA, $TiO_2$ scaffold surface.
Figure 21B:
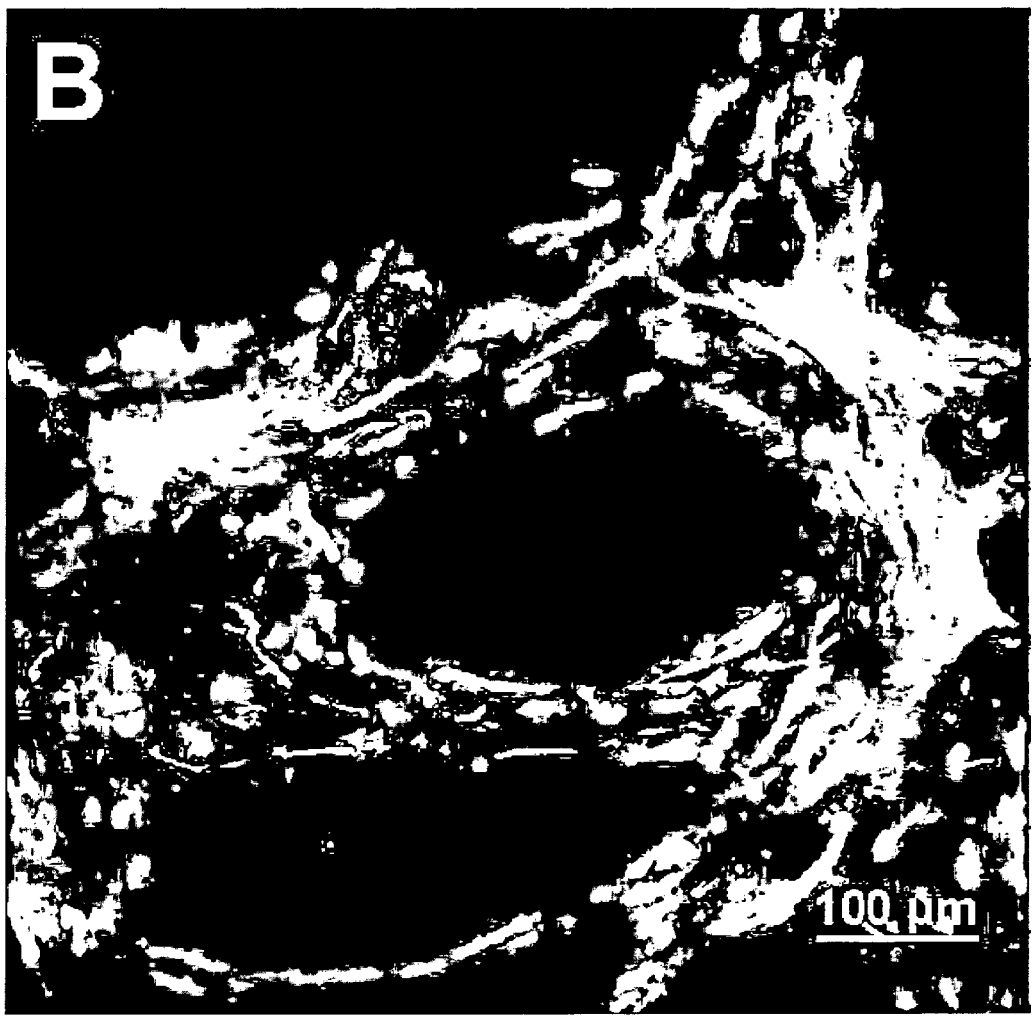
Figure 21C:
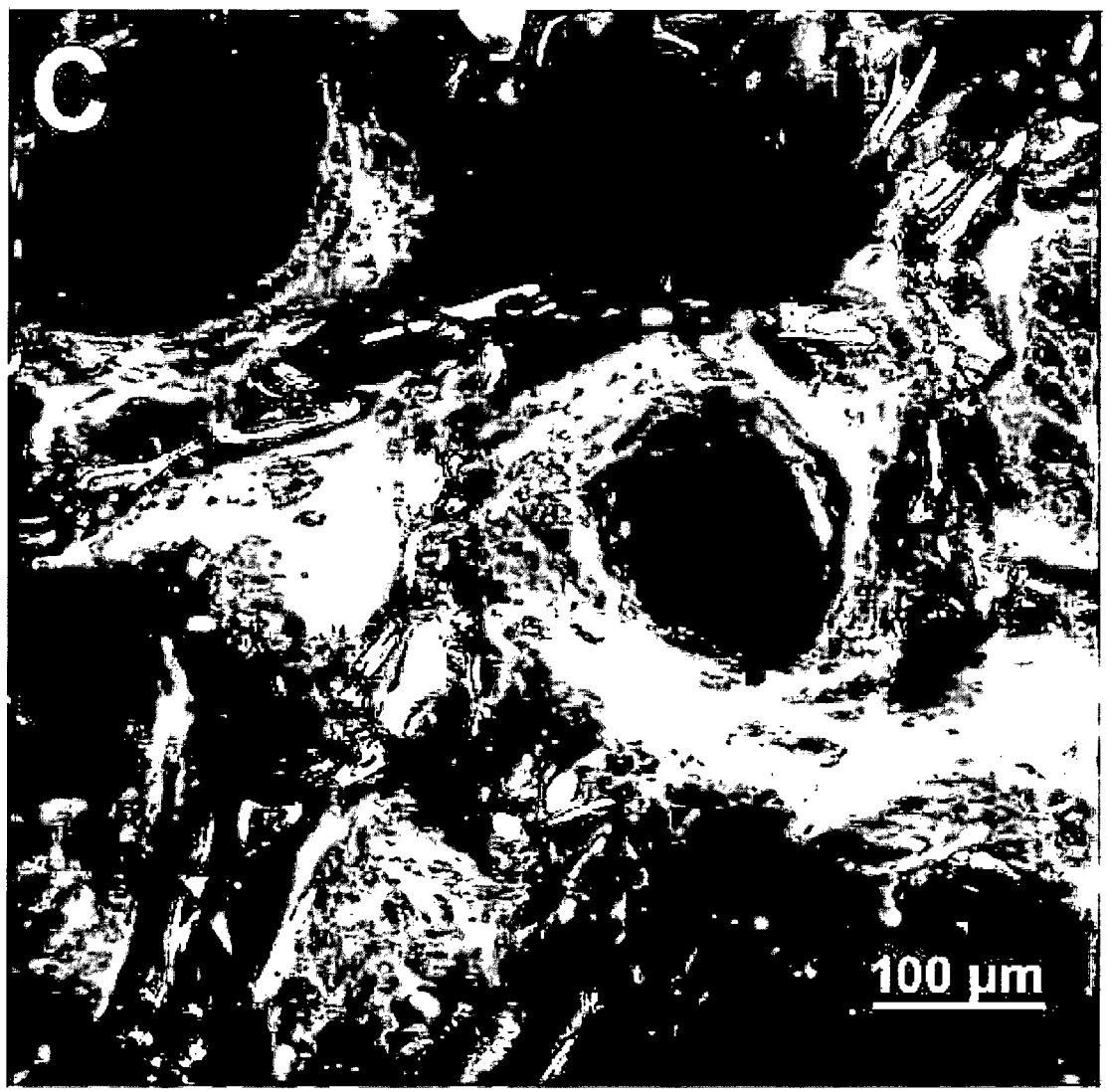

After 21 days of culture, the relative expression of BGLAP was significantly increased in cells cultured on scaffolds with 10 µM SIM when compared to scaffolds without SIM and normalized to GAPDH. No significant differences were observed in the expression of ALPL, COL1A1, TNFRSF11B or VEGFA mRNA levels among experimental groups at any of the time points studied (FIG. 20). To evaluate the effect of SIM on the deposition of type I collagen, CLSM visualization was performed on stained scaffolds. Type I collagen was detected intracellular in the majority of cells in all scaffolds. However, extracellular collagen fibrils were almost absent in scaffolds with SIM regardless of the concentration (FIG. 21; A-B), while rich networks of type I collagen fibrils were seen in the scaffolds without SIM (FIG. 21; C).

5. Conclusion

In conclusion, the study shows that alginate-coated TiO$_2$ scaffolds can act as a matrix for SIM delivery inducing osteoblast cell differentiation. Scaffolds coated with alginate containing 10 µm SIM had low cytotoxicity and significantly increased the secretion of VEGFA and BGLAP from osteoblasts cultured on the scaffolds. The combination of the local osteogenic effect of SIM and the physical properties of the TiO$_2$ scaffolds may represent a new strategy for bone tissue regeneration in load-bearing bone.

Example 10

Preparation of an Alginate Coated Titanium Dioxide Scaffold for Local Delivery of Emdogain (EMD) and for Support of Human Adipose-Derived Mesenchymal Stem Cells 1. Materials and Methods
1.1. Fabrication of Titanium Dioxide Scaffolds Porous TiO$_2$ scaffolds, with a size of 9 mm in diameter and 4 mm in height, were produced by polymer sponge replication as previously described (Tiainen et al 2010). In short, polymer foams were impregnated with TiO$_2$ slurry, dried and subsequently sintered at 1500° C. for 40 hours. Produced scaffolds were sterilized by autoclaving at 121° C. for 20 minutes.

1.2. Isolation, Characterization and Cell Culture of Human Adipose-Derived Mesenchymal Stem Cells hAD-MSC were isolated from subcutanous fat tissues. To confirm their mesenchymal character, the cells were characterized with respect to their expression of surface antigens and the ability to selectively differentiate into osteogenic, chondrogenic and adipogenic lineages in response to environmental stimuli. The following marker proteins were assessed:
CD14(−), CD19(−), CD34(+), CD45(−), CD44(+), CD73 (+), CD90(+), CD105(+), HLA-DR(−) and IgG(−). The osteogenic differentiation phenotype of the cells was assessed by runt-related transcription factor 2 (RUNX2), collagen type I alpha 1 (COL1A1), alkaline phosphatase (ALPL) activity/mRNA expression, and histological evaluation with alizarin red staining. Chondrogenic differentiation was analyzed by evaluating SRY (sex determining region Y)-box 9 (SOX9), collagen type II alpha 1 (COL2A1) and aggrecan (ACAN) mRNA expression. Adipogenic differentiation was determined by peroxisome proliferator-activated receptor gamma (PPARG) mRNA expression, and histological visualization with oil red staining.

1.3. Cell Culture of Primary Human Osteoblasts hOSTs (Cambrex Bio Science, Walkersville, Md., USA) from three male donors, one from tibia and two from femur, respectively, were cultured in osteoblast culture medium supplemented with 10% foetal bovine serum, 0.1% gentamicin sulfate and amphotericin-B antibiotics and 0.1% ascorbic acid (Lonza Walkersville, Md., USA) in 75 cm$^2$ culture flasks at 37° C. in a humidified atmosphere of 5% CO$_2$. At the time of cell seeding, the hOSTs from tibia had reached passage 9 and the hOSTs from the two femur donors had reached passage 6 and 8, respectively.

1.4. Seeding of Human Adipose-Derived Mesenchymal Stem Cells and Primary Human Osteoblasts Scaffolds pre-soaked with culture medium were placed in 24-well culture plates, and the cell suspension was added drop-wise on the top of the scaffolds at a density of $2 \times 10^5$ cells/scaffold in 1 ml of culture medium. In order to ensure a homogenous cell distribution throughout the scaffold, an agitated seeding method was used (Takahashi et al 2003). After seeding, the plates were agitated on an orbital shaker at 200 rpm for 6 hours at 37° C. in humidity conditions. Cell-seeded scaffolds were transferred to new culture plates in 1 ml culture medium and maintained at 37° C. in a humidified atmosphere of 5% $CO_2$. The next day, all cell-seeded scaffolds were soaked twice in 4.6% D-Mannitol solution followed by centrifugation at 300×g for 1 minute. Then, the cell-embedded scaffolds were treated differently according to the respective groups. The uncoated scaffolds in the control group were immediately transferred to new culture plates in 1 ml culture medium and maintained at 37° C. in a humidified atmosphere of 5% $CO_2$ up to 21 days. The scaffolds in the alginate group without EMD were coated with alginate hydrogel by soaking for 10 minutes in a freshly made solution consisting of 300 µl 2% (w/v) Pronova UP LVG sodium alginate (FMC BioPolymer, Sandvika, Norway), 600 µl 2% (w/v) Pronova UP LVG calcium alginate (FMC BioPolymer, Sandvika, Norway), 600 µl 0.003% (w/v) citric acid/4.6% D-Mannitol and 300 µl 4.6% D-Mannitol followed by centrifugation at 300×g for 1 minute to remove the excess alginate solution. The alginate-coated scaffolds were stabilized in a 50 mM $CaCl_2$ solution and transferred to new culture plates in 1 ml culture medium and maintained at 37° C. in a humidified atmosphere of 5% $CO_2$ up to 21 days. The scaffolds in the alginate group with EMD were treated in the same way as scaffolds in the alginate group without EMD, except that 600 µl 0.003% (w/v) citric acid/4.6% D-Mannitol contained an additional 150 µg/ml of EMD (Lot number: EMD 9121, Institut Straumann, Basel, Switzerland), resulting in final EMD concentration of 50 µg/ml for the entire alginate solution. Triplicates of each donor, each treatment, and for two harvest timepoints were included, in total 54 scaffolds. The medium was changed every other day and saved for use in cytotoxicity, alkaline phosphatase (ALP) activity, total protein content and expression assays. Scaffolds were harvested after 14 and 21 days of culture for use in real-time RT-PCR and immunocytochemistry.

1.5. Visualization of Cell-Seeded Scaffolds Coated with Alginate Hydrogel

The alginate coating was visualized by Periodic acid-Schiff (PAS) staining. In brief, scaffolds were washed with milliQ water and oxidized in 1% periodic acid solution (Sigma-Aldrich, St. Louis, Mo., USA) for 5 minutes. Then, the scaffolds were rinsed with milliQ water and placed into Schiff reagent (Sigma-Aldrich, St. Louis, Mo., USA) for 15 minutes. Finally, the scaffolds were soaked in lukewarm tap water for 5 minutes and subsequently photographed. Further, the adherence of hAD-MSC in the alginate coating was assessed by PAS/Pan-Cadherin double staining after 2 days of culture. Scaffolds were cut in half by a scalpel and fixed in 4% paraformaldehyde (PFA)/4.6% D-Mannitol for 15 minutes and subsequently stored in 1% PFA/4.6% D-Mannitol until further processing. Fixed scaffolds were first stained according to PAS method and followed by Pan-Cadherin staining. In short, PAS stained scaffolds were incubated with monoclonal mouse anti-human Pan cadherin antibody (I-8H5, MP Biomedicals, Santa Ana, Calif., USA) diluted to 4 µg/ml in 1.25% bovine serum albumin (BSA) in phosphate buffered saline (PBS) with 0.2% Triton X for 1 hour at room temperature, followed by incubation for 30 minutes at room temperature in Cy3-conjugated donkey anti-mouse IgG (Jackson ImmunoResearch, West Grove, Pa., USA) diluted in 2.5% BSA/0.05% Tween-20/PBS at a concentration of 2 µg/ml. Cell-seeded whole mount stained scaffolds were counterstained using DAPI, placed on a coverslip and covered with Dako fluorescent mounting medium (Dako, Glostrup, Denmark). Confocal laser scanning microscopy was performed on a FluoView 1000 confocal laser scanning microscope (CLSM) (Olympus, Center Valley, Pa., USA). The scaffold surfaces were visualized using the CLSM in reflection mode. Images were analyzed using ImageJ (NIH, Bethesda, Md., USA).

1.6. Cytotoxicity Assay

The cytotoxicity of the cell-seeded scaffolds was estimated based on the activity of the cytosolic enzyme lactate dehydrogenase (LDH) in the culture medium. The LDH activity was determined in medium collected every other day until 14 days of culture, according to the manufacturer's cytotoxicity detection kit instructions (Roche Diagnostics, Mannheim, Germany). 50 µl of sample was incubated with 50 µl of the kit reaction mixture for 30 minutes in the dark at room temperature. The absorbance of the samples was measured at 492 nm in a plate reader (Biochrom Asys Expert 96 Microplate Reader, Biochrom, Holliston, Mass., USA).

In addition, hAD-MSC viability was visualized by acridine orange/ethidium bromide staining at 2 day of culture. Scaffolds were cut in half by a scalpel and fixed in 4% paraformaldehyde (PFA)/4.6% D-Mannitol for 15 minutes and subsequently stored in 1% PFA/4.6% D-Mannitol until further processing. Confocal laser scanning microscopy was performed on a FluoView 1000 CLSM (Olympus, Center Valley, Pa., USA). The scaffold surfaces were visualized using the CLSM in reflection mode. Images were analyzed by ImageJ (NIH, Bethesda, Md., USA).

1.7. Total Protein Content Assay

The total protein content of the cell-seeded scaffolds was determined in the culture medium after 2, 8, 14 and 21 days of culture with a bicinchoninic acid (BCA) protein assay kit (Thermo Scientific Pierce Biotechnology, Rockford, Ill., USA) according to the manufacturer's instructions. 25 µl of sample was incubated with 200 µl of the kit working reagent for 30 minutes in the dark at 37° C. The absorbance of the samples was measured at 562 nm in a plate reader (Biochrom Asys Expert 96 Microplate Reader, Biochrom, Holliston, Mass., USA) and total protein amount was calculated by a standard curve based on BSA (Thermo Scientific Pierce Biotechnology, Rockford, Ill., USA).

1.8. Alkaline Phosphatase Activity Assay

The ability of ALP to hydrolyze P-nitrophenyl phosphate (pNPP) substrates (Sigma-Aldrich, St. Louis, Mo., USA) into the yellow end-product, p-nitrophenol, was used to quantify the ALP activity in the culture medium after 2, 4, 6, 10, 16 and 20 days of culture for hAD-MSCs and 4, 8, 12, 16 and 21 days of culture for hOSTs. 25 µl of sample was incubated with 100 µl pNPP for 30 minutes in the dark at room temperature, and subsequently 50 µl of 3M NaOH was added to stop the reaction. The absorbance was measured at 405 nm in a plate reader (Biochrom Asys Expert 96 Microplate Reader, Biochrom, Holliston, Mass., USA) and the ALP activity was quantified by a standard curve based on calf intestinal alkaline phosphatase (Promega, Madison, Wis., USA).

1.9. RNA Isolation and Real-Time RT-PCR Analysis

Total RNA was isolated from cell-seeded scaffolds by the Qiagen RNA mini-kit (Qiagen, Hilden, Germany) according to the protocol provided by the manufacturer. cDNA was synthesized with RevertAid First Strand cDNA Synthesis Kit (Fermentas, St. Leon-Rot, Germany) using random primers. Real-time PCR was performed in the Applied Biosystems 7300 Real-Time System (Life Technologies, Paisley, UK) with TaqMan® Universal Master Mix. The amplification program consisted of a preincubation step for template cDNA denaturation (10 min, 95° C), followed by 40 cycles comprising of a denaturation step (15 s, 95° C) and an annealing step (60 s, 60° C.). A negative control without cDNA template was run in each assay. Real-time RT-PCR for hAD-MSCs was done for glyceraldehyde-3-phosphate dehydrogenase (GAPDH), RUNX2, SOX9, PPARG, COL1A1, osteoprotegerin (TNFRSF11B), secreted phosphoprotein 1 (SPP1), ALPL and osteocalcin (BGLAP). Real-time RT-PCR for hOSTs was done for GAPDH, COL1A1, TNFRSF11B, SPP1, ALPL and BGLAP. Real-time RT-PCR data was analyzed using the $\Delta\Delta CT$ method (Pfaffl et al. 2001).

1.10. Immunoassay: Quantification of Secreted Proteins

Multianalyte profiling of protein levels in the culture medium was performed on the Luminex 100/200 system (Luminex, Austin, Tex., USA) employing xMAP technology. Acquired fluorescence data was analyzed by the xPONENT 3.1 software (Luminex, Austin, Tex., USA). The amount of osteoprotegerin (TNFRSF11B), secreted phosphoprotein 1 (SPP1) and osteocalcin (BGLAP) in the culture medium was measured by the human bone panel kit (Millipore, Billerica, Mass., USA) after 2, 8, 14 and 21 days of culture. All analyses were performed according to the manufacturer's protocols.

1.11. Immunocytochemistry and Confocal Laser Scanning Microscopy

After 14 and 21 days of culture, scaffolds were cut in half by a scalpel and fixed in 4% paraformaldehyde (PFA)/4.6% D-Mannitol for 15 minutes and subsequently stored in 1% PFA/4.6% D-Mannitol until further processing. Fixed scaffolds were submitted to heat induced epitope retrieval by heating to 95° C. in 0.05% citraconic anhydride in milliQ water (pH 7.4) for 15 minutes, Incubated with monoclonal mouse anti-human antibodies (I-8H5, MP Biomedicals, Santa Ana, Calif., USA) diluted to 1 µg/ml in 1.25% bovine serum albumin (BSA) in phosphate buffered saline (PBS) with 0.2% Triton X for 1 hour at room temperature, followed by incubation for 30 minutes at room temperature in Cy3-conjugated donkey anti-mouse IgG (Jackson ImmunoResearch, West Grove, Pa., USA) diluted in 2.5% BSA/0.05% Tween-20/PBS at a concentration of 2 mg/ml. Cell-seeded whole mount stained scaffolds were counterstained using DAPI and mounted on a coverslip with Dako fluorescent mounting medium (Dako, Glostrup, Denmark). Confocal laser scanning microscopy was performed on a FluoView 1000 CLSM (Olympus, Center Valley, Pa., USA). The scaffold surfaces were visualized using the CLSM in reflection mode. Images were analyzed by ImageJ (NIH, Bethesda, Md., USA).

1.12. Statistics

The data obtained by cytotoxicity, ALP activity, gene expression, total protein content and secretion analyses was compared between the groups using Holm-Sidak test following a parametric one way ANOVA. Where the equal variance and/or the normality test failed, a Kruskal-Wallis one way ANOVA on ranks was performed (SigmaPlot 12.3, Systat Software, San Jose, Calif., USA). A probability of ≤0.05 was considered significant.

2. Results 2.1. Characterization of Alginate-Coated Cell-Seeded Scaffolds

Figure 22:
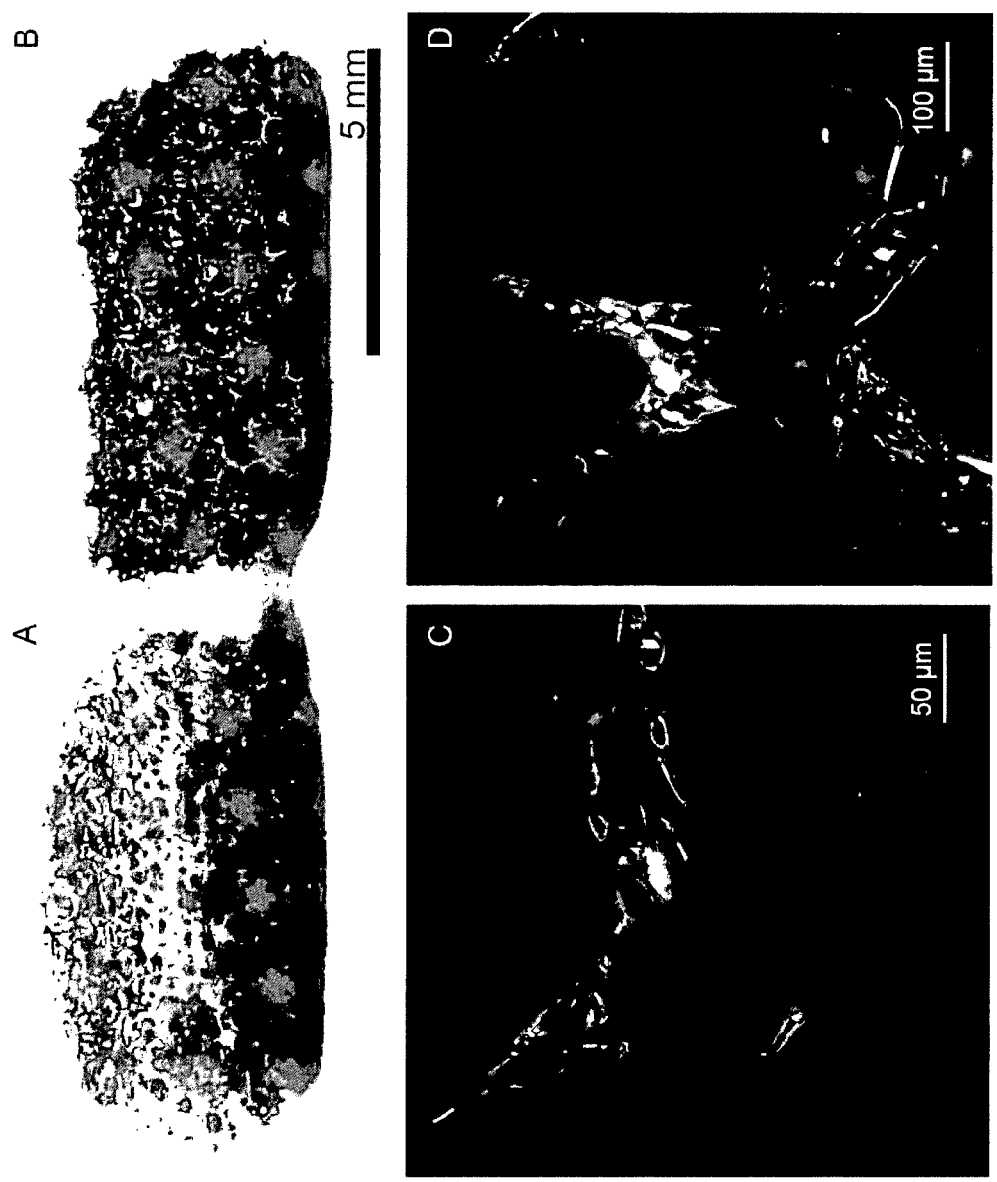
FIG. 22. Periodic acid-Schiff/Pan-cadherin visualization of alginate-coated and uncoated scaffold. Periodic acid-Schiff staining of alginate-coated (B) and uncoated (A) scaffold. The alginate (red) is distributed throughout the scaffold as seen in the view from the cross section (B). Periodic acid-Schiff/Pan-cadherin double staining of cell-seeded alginate-coated (D) and uncoated (C) scaffold at 2 day. Alginate layer containing cells is covering the scaffold (D).
Figure 23:
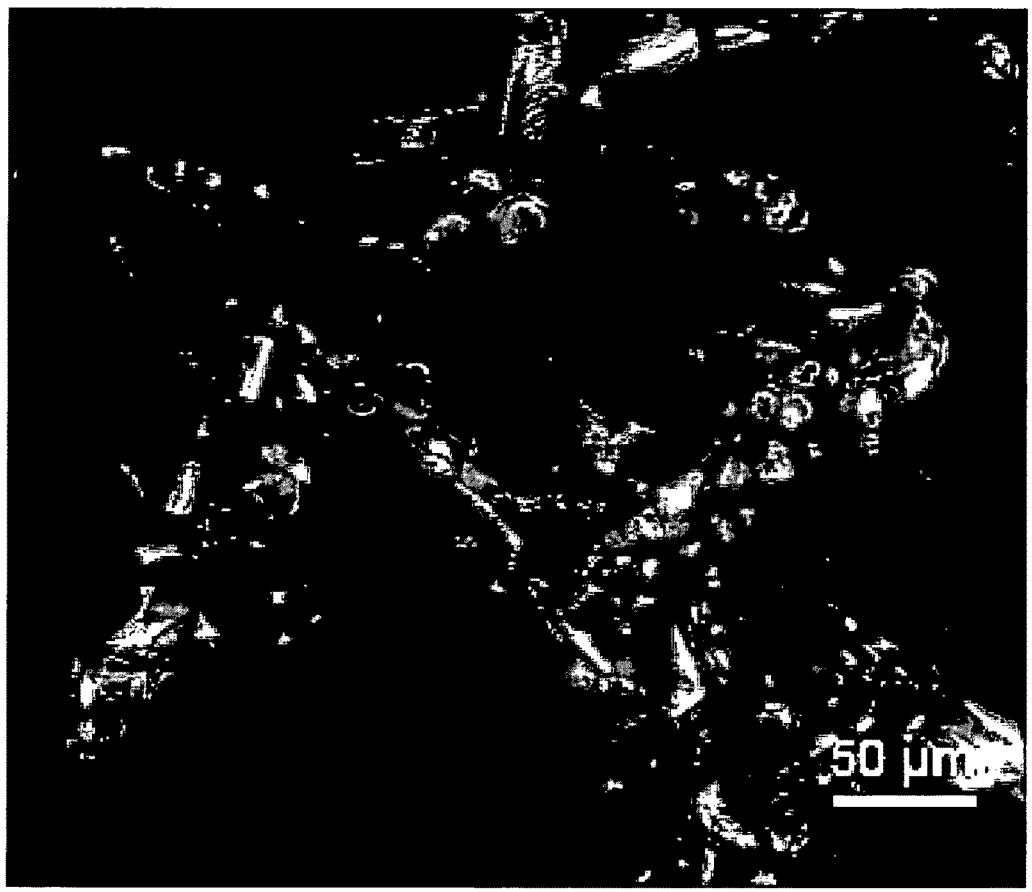
FIG. 23. Acridine-orange/ethidium bromide visualization of cell-seeded alginate-coated scaffold. Acridine-orange/ethidium bromide staining of human adipose-derived mesenchymal stem cells seeded on alginate-coated scaffold at 2 day. Majority of the cells have survived the alginate coating procedure. Live cells stain green, dead cells stain red.

PAS staining of the alginate-coated scaffolds revealed an even distribution of alginate hydrogel, coating the entire surface of the $TiO_2$ scaffold struts (FIG. 23A). Further, hAD-MSC adherence to alginate-coated $TiO_2$ scaffolds was demonstrated by PAS/Pan-cadherin double staining (FIG. 22D). Moreover, the majority of the seeded hAD-MSCs were viable according to the acridine-orange/ethidium bromide staining at 2 day of culture (FIG. 23).

2.2. Human Adipose-Derived Stem Cell Characteristics

Cellular surface antigen expression patterns CD14(−), CD19(−), CD34(+), CD45(−), CD44(+), CD73(+), CD90(+), CD105(+), HLA-DR(−) and IgG(−) suggested the absence of hematopoietic or endothelial origin cells. Osteo- and adipogenic differentiation was demonstrated by histological visualization with alizarin red and oil red, respectively. In addition, the cells differentiated selectively into bone-, cartilage- and adipose-depositing cells in a culture. Because of their antigen surface expression pattern, histological evaluation and their potential to differentiate along the osteogenic, chondrogenic and adipogenic lineages the cells were referred to as hAD-MSCs.

2.3. Cytocompatibility/Lactate Dehydrogenase Activity

Figure 24A:
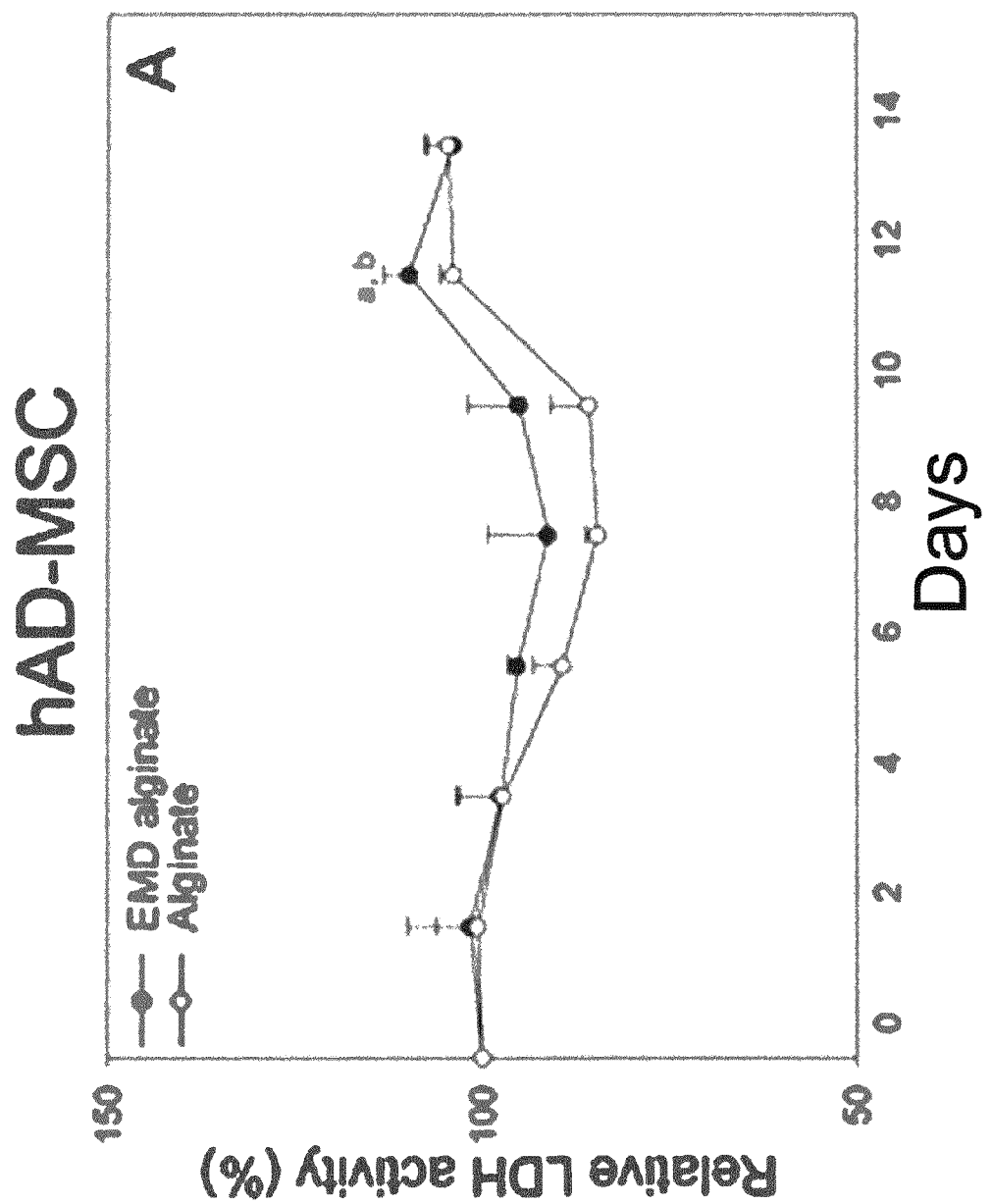
FIG. 24A-D. Lactate dehydrogenase activity and total protein content assays. Lactate dehydrogenase activity and total protein content in culture medium from cell-seeded alginate-coated scaffolds with (EMD alginate) or without emdogain (Alginate) is shown in percentage of control, cell-seeded uncoated scaffolds, for human adipose-derived mesenchymal stem cells (hAD-MSC) (A, C), and primary human osteoblasts (hOST) (B, D) measured at every other day up to 14 days. Values represent the mean +SD. Statistical analysis: (a) p≤0.05 versus alginate-coated scaffold without emdogain and (b) p≤0.05 versus cell-seeded uncoated scaffold.
Figure 24B:
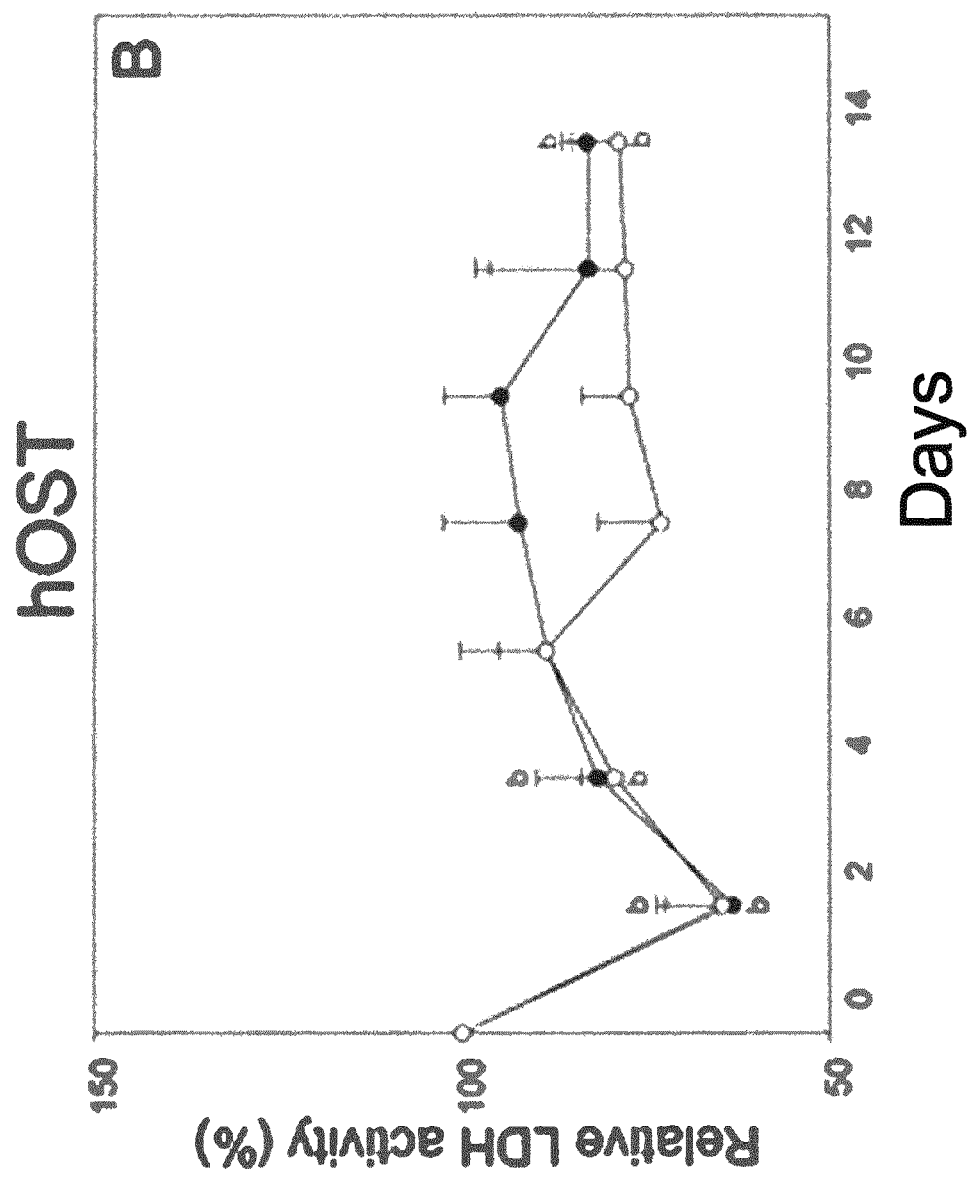

A 14-day cytotoxicity study was performed for alginate-coated scaffolds with or without EMD to investigate the effect of alginate and EMD on hAD-MSC and hOST viability. A higher LDH activity was generally detected in the medium from alginate-coated scaffolds with EMD compared to alginate-coated scaffolds without EMD throughout the 14-day period. Neither of the scaffolds caused a significant increase in LDH activity compared to the effect of uncoated scaffolds, except hAD-MSCs from alginate-coated scaffolds with EMD revealed a significant increase in LDH activity when compared to alginate-coated scaffolds without EMD and uncoated scaffolds at day 12 (FIG. 24A). Moreover, a significant decrease in LDH activity was observed in hOSTs medium from alginate-coated scaffolds with and without EMD when compared to uncoated scaffolds at 2, 4 and 14 days (FIG. 24B). Some variation was seen in the LDH activity profiles of hAD-MSCs and hOSTs, indicating cell type dependent differences in the cellular response to alginate and EMD (FIG. 24; A-B).

2.4. Total Protein Content

Figure 24C:
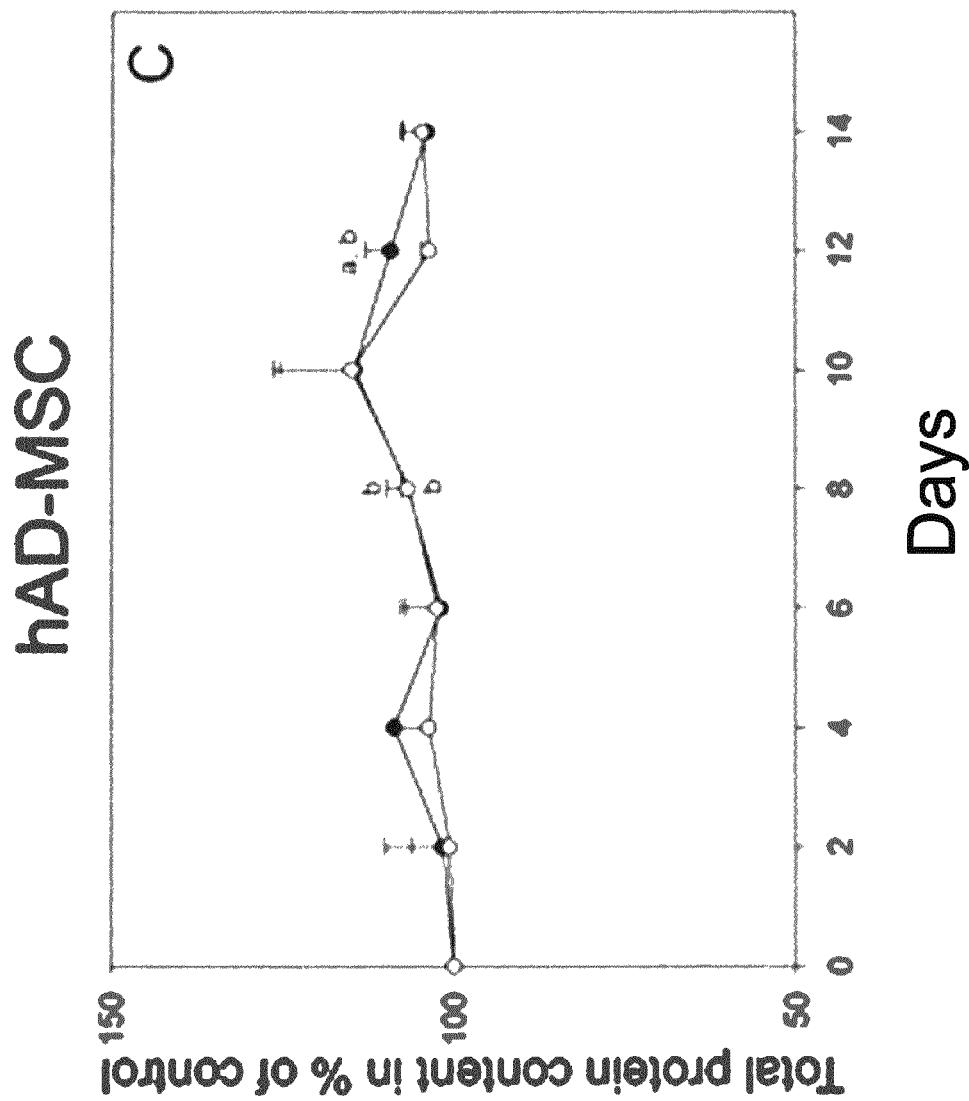
Figure 24D:
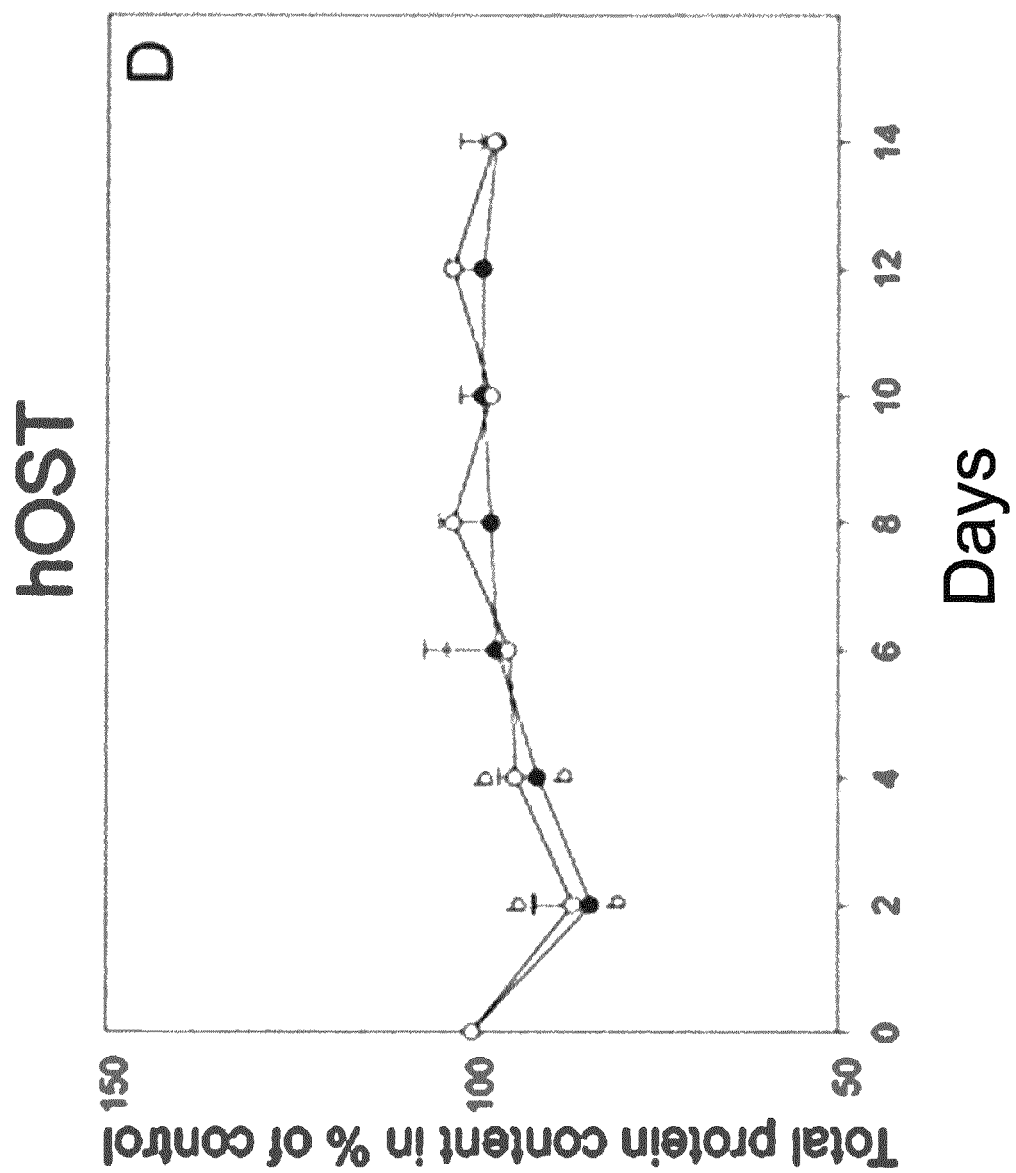

No significant differences were generally seen in the total protein content of hAD-MSC culture medium at any time points either for scaffolds with or without EMD when compared to uncoated scaffolds, except a significant increase in the total protein amount was detected in medium from alginate-coated scaffolds with and without EMD when compared to uncoated scaffolds at 8 day and a significant increase in the total protein amount was seen in medium from alginate-coated scaffolds with EMD when compared to alginate-coated scaffolds without EMD and uncoated scaffolds at 12 day (FIG. 24C). No significant differences were generally seen in the total protein content of hOST culture medium at any time points either for scaffolds with or without EMD when compared to uncoated scaffolds, except a significant decrease in the total protein amount was detected in medium from alginate-coated scaffolds with and without EMD when compared to uncoated scaffolds at 2 and 4 days (FIG. 24D).

2.5. Alkaline Phosphatase Activity

Culturing hAD-MSCs on alginate-coated scaffolds with or without EMD did not significantly change the ALP activity in the culture medium at any of the time points measured either for scaffolds with or without EMD when compared to uncoated scaffolds, except for donor 1 the ALP activity in the medium was significantly increased from cells cultured on alginate-coated scaffolds with EMD when compared to alginate-coated scaffolds without EMD and uncoated scaffolds at day 20, and for donor 3 the ALP activity in the medium was significantly decreased from cells cultured on scaffolds with EMD when compared to alginate-coated scaffolds without EMD and uncoated scaffolds at day 10.

Culturing hOSTs on alginate-coated scaffolds with or without EMD did not significantly change the ALP activity in the culture medium at any of the time points measured either for scaffolds with or without EMD when compared to uncoated scaffolds, except for donor 1 the ALP activity in the medium was significantly decreased from cells cultured on alginate-coated scaffolds without EMD when compared to uncoated scaffolds at day 4, for donor 2 the ALP activity in the medium was significantly decreased from cells cultured on alginate-coated scaffolds without EMD when compared to uncoated scaffolds at day 12, and for donor 3 the ALP activity in the medium was significantly decreased from cells cultured on alginate-coated scaffolds with and without EMD when compared to uncoated scaffolds at 4 and 16 days. Some variation was seen in the ALP activity profiles, indicating donor dependent differences in the cellular response to alginate-coated scaffolds with or without EMD.

2.6. Real-Time RT-PCR Analysis

No significant differences were observed in the expression of COL1A1, TNFRSF11B, SPP1, ALPL and BGLAP mRNA levels in hAD-MSCs among experimental groups at any of the time points studied. In addition, no significant differences were observed in the expression of RUNX2, SOX9 and PPARG mRNA levels among experimental groups at any of the time points studied.

No significant differences were observed in the expression of SPP1, ALPL and BGLAP mRNA levels in hOSTs among experimental groups at any of the time points studied. Nevertheless, after 14 days of culture, the relative expression of COL1A1 was significantly increased in hOSTs cultured on scaffolds with EMD when compared to scaffolds without EMD, uncoated scaffolds and normalized to GAPDH. The relative expression of TNFRSF11B was after 14 days of culture significantly increased in cells cultured on scaffolds with EMD when compared to uncoated scaffolds and normalized to GAPDH.

2.7. Visualization of RUNX2 and SOX9 by Confocal Laser Scanning Microscopy

Figure 25:
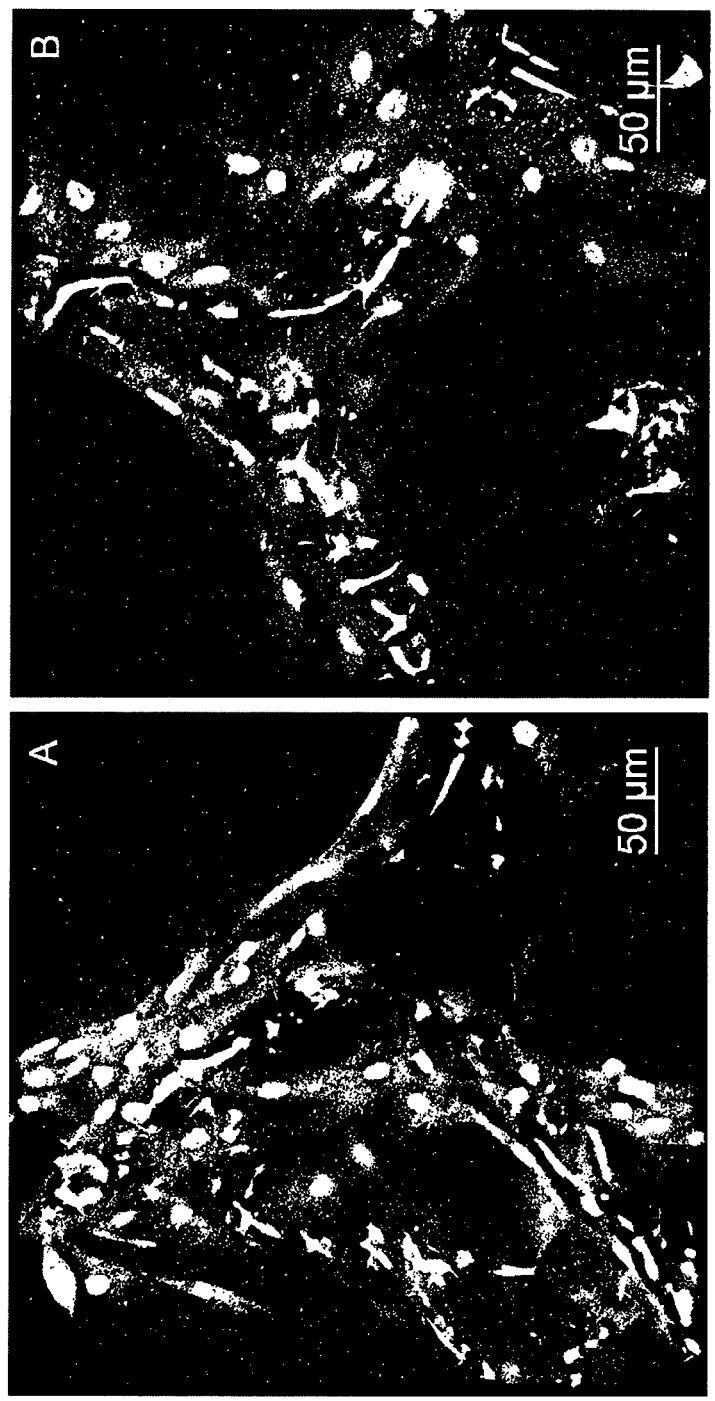
FIG. 25. Confocal laser scanning microscopy visualization of RUNX2 and SOX9. Fluorescence immunocytochemical analysis of RUNX2 and SOX9 in human adipose-derived mesenchymal stem cells cultured on alginate-coated scaffold with emdogain (A) and uncoated scaffold (B). RUNX2 is detected in the majority of the cells cultured on scaffolds with emdogain (A). However RUNX2 and SOX9 are detected equally in the cells cultured on uncoated scaffold (B). RUNX2 (green), SOX9 (red), TiO2 scaffold surface (white).

To evaluate the effect of EMD on the deposition of RUNX2 and SOX9, CLSM visualization was performed on stained scaffolds (FIG. 25).

2.8. Immunoassay: Quantification of Secreted Proteins

No significant differences were seen in the TNFRSF11B, SPP1 and BGLAP content of either hAD-MSC or hOST culture medium at any time points either from scaffolds with or without EMD when compared to uncoated scaffolds. No substantial differences were seen in the second donor's TNFRSF11B content of the culture medium at any time points either from scaffolds with or without EMD, and for the first donor no substantial differences were detected in TNFRSF11B content of the culture medium at 8, 14 and 21 days either from scaffolds with or without EMD. However, the content of third donor's TNFRSF11B in the culture medium was more increased from cells cultured on scaffolds without EMD when compared to scaffolds with EMD at all-time points. No substantial differences were observed in the first and third donor's SPP1 content of the culture medium at any time points either from scaffolds with or without EMD, except the content of third donor's SPP1 in the culture medium was more expressed from cells cultured on scaffolds with EMD when compared to scaffolds without EMD at 21 day. Furthermore, the second donor's SPP1 content in the culture medium was more enhanced from cells cultured on scaffolds with EMD when compared to scaffolds without EMD at 8 and 21 days. No substantial differences were observed in the first and third donor's BGLAP content of the culture medium at any time points either from scaffolds with or without. However, the second donor's BGLAP content in the culture medium was more enhanced from cells cultured on scaffolds with EMD when compared to scaffolds without EMD at 2 and 8 days.

The content of first and second donor's TNFRSF11B in the culture medium was more expressed from cells cultured on scaffolds with EMD when compared to scaffolds without EMD at all-time points, the content of third donor's TNFRSF11B in the culture medium was more expressed from cells cultured on scaffolds without EMD when compared to scaffolds with EMD at 2 and 8 days. However, no substantial differences were observed in the third donor's TNFRSF11B content of the culture medium at 14 and 21 days either from scaffolds with or without EMD. The content of first donor's SPP1 in the culture medium was more increased from cells cultured on scaffolds with EMD when compared to scaffolds without EMD at all-time points. The content of second donor's SPP1 in the culture medium was more increased from cells cultured on scaffolds with EMD when compared to scaffolds without EMD at 2, 8 and 14 days. No substantial differences were observed in the third donor's SPP1 content of the culture medium at 2 and 8 days either from scaffolds with or without EMD. The content of first donor's BGLAP in the culture medium was more increased from cells cultured on scaffolds without EMD when compared to scaffolds with EMD at 2 day. However, the content of first donor's BGLAP in the culture medium was more increased from cells cultured on scaffolds with EMD when compared to scaffolds without EMD at 8 day. The content of second donor's BGLAP in the culture medium was more increased from cells cultured on scaffolds without EMD when compared to scaffolds with EMD at 2 and 21 days. However, the content of second donor's BGLAP in the culture medium was more increased from cells cultured on scaffolds with EMD when compared to scaffolds without EMD at 14 day. The content of third donor's BGLAP in the culture medium was more increased from cells cultured on scaffolds with EMD when compared to scaffolds without EMD at 8, 14 and 21 days. However, the content of third donor's BGLAP in the culture medium was more increased from cells cultured on scaffolds without EMD when compared to scaffolds with EMD at 2 day.

5. Conclusion

In summary, from the results, we can conclude that hAD-MSCs and hOSTs have the ability to survive the coating procedure for EMC derivative delivery. Moreover, hOSTs could differentiate into osteogenic lineage within alginate-coated scaffolds with EMD, which is important before evaluating the efficacy in vivo.

Example 11

Figure 26:
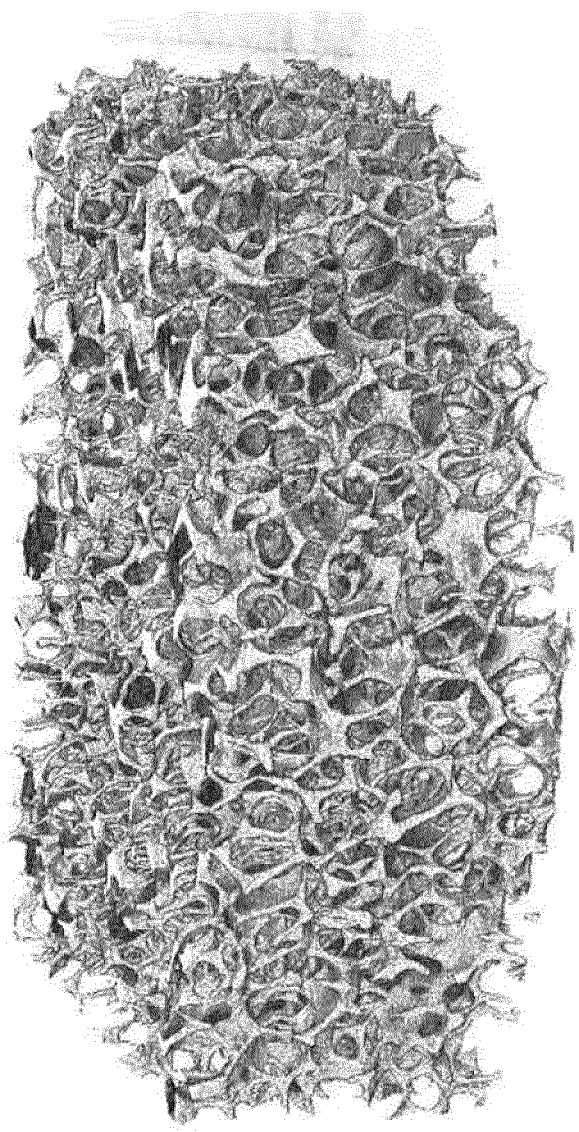
FIG. 26. Cross section of $TiO_2$ scaffold coated with an alginate layer produced by the method of the present document showing an open porous structure. The diameter of the section is 3 mm.

Fabrication of $TiO_2$ Scaffolds Coated with Radiopaque Alginate Layer Proving Open Porous Structure The porous $TiO_2$ scaffolds were produced by polymer sponge replication as previously described by (Tiainen H et al., 2010), with a size of 9 mm of diameter and 8 mm high. Then, $TiO_2$ scaffolds were coated with one layer of 2% alginate gel with a radiopaque contrast liquid (Omnipaque (iohexol), GE Healtcare). Briefly, $TiO_2$ scaffolds were submerged into 2% alginate solution with or without P2 (SEQ ID NO 1) under agitation at 100 rpm on an orbital shaker (IKA Vibrax VXR basic, Staufen, Germany) for 1 h at room temperature. Scaffolds were then centrifuged at 252×g for 1 min. Samples were immersed into 50 mM $CaCl_2$ for 1 h to allow gelation. Scaffolds were then rinsed with $dH_2O$ to remove the excess of $CaCl_2$. Finally, samples were let to dry overnight at room temperature. Scaffolds coated with one layer of 2% alginate gel (control alginate scaffold), were used as control group, whereas uncoated $TiO_2$ scaffolds (without alginate, SC) were also used as control group. The scaffolds were scanned in a microCT scanner (Skyscan 1172, Kontich, Belgium), visualized in CTvox and analysed in CTan. The pore diameter of the scaffold was only reduced with 5% and the porosity change was less than 3%. The interconnectivity did not change upon applying the alginate layer proving that the scaffold still has an open porous structure and only very few pores were blocked (dark colour) (FIG. 26). It was also visible that all the struts were covered with a thin layer (<10 µm) of alginate.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

REFERENCES

Tiainen H, Lyngstadaas S P, Ellingsen J E, Haugen H J. Ultra-porous titanium oxide scaffold with high compressive strength. J Mater Sci Mater Med 2010; 21:2783-92.

Takahashi Y, Tabata Y. Homogeneous seeding of mesenchymal stem cells into nonwoven fabric for tissue engineering. Tissue Eng 2003; 9:931-8.

Tiainen H, Monjo M, Knychala J, Nilsen O, Lyngstadaas S P, Ellingsen J E and Haugen H J. The effect of fluoride surface modification of ceramic $TiO_2$ on the surface properties and biological response of osteoblastic cells in vitro *Biomed. Mater.* 2011; 6 045006.

Rubert M, Ramis J M, Vondrasek J, Gay'a A, Lyngstadaas S P and Monjo M. Synthetic peptides analogue to enamel proteins promote osteogenic differentiation of MC3T3-E1 and mesenchymal stem cells J. Biomater. Tissue Eng. 2011; 1 198-209.

Monjo M, Ramis J M, Ronold H J, Taxt-Lamolle S F, Ellingsen J E and Lyngstadaas S P. Correlation between molecular signals and bone bonding to titanium implants Clin. Oral Implants Res. 2012 doi: 10.1111/j.1600-0501.2012.02496.x.Maniatopoulos C, Sodek J, Melcher A H. Bone formation in vitro by stromal cells obtained from bone marrow of young adult rats. Cell and tissue research 1988; 254:317-30.

Pfaffl M W. A new mathematical model for relative quantification in real-time RT-PCR. Nucleic Acids Res 2001; 29:e45-e.

Larry S. Liebovitch, Tibor Toth, A fast algorithm to determine fractal dimensions by box counting, Physics Letters A, Volume 141, Issues 8-9, 20 Nov. 1989, Pages 386-390, ISSN 0375-9601, http://dx.doi.org/10.1016/0375-9601(89)90854-2. (http://www.sciencedirect.com/science/article/pii/0375960189908542)

The invention claimed is:

1. A titanium dioxide scaffold comprising an open porous structure, wherein at least part of the surface of said titanium dioxide scaffold is provided with a hydrogel coating comprising at least one biologically active substance, wherein a portion of said coating is formed on the walls of pores inside the scaffold, and wherein said coating does not substantially block the pores, wherein said titanium dioxide scaffold is produced by a method comprising the steps of:
   a) providing a titanium dioxide scaffold;
   b) providing a polymer solution comprising a biologically active substance and about 1-10% w/v of a polymer having a molecular weight (Mw) of 1,000-1,000,000 g/mol, to at least part of said titanium dioxide scaffold and then centrifuging the titanium dioxide scaffold; and
   c) effecting gelation of the polymer provided to the titanium dioxide scaffold in step (b).

2. A titanium dioxide scaffold according to claim 1, wherein said hydrogel coating comprises at least one polymer selected from the group consisting of alginate, chitosan, hyaluronic acid, poly ethylene glycol (PEG), cellulose, poly(acrylic acid) (PAA), poly(glycolic acid) (PGA), poly (lactic acid) (PLA),PLA-PGA, PLA-PEG, dextran, dextran-PEG, starch, collagen based gels, agaroses, pluronic acid, heparan sulfate, glycosaminoglycans, polyethylene oxide (PEO), copolymer of ethylene oxide and propylene oxide (P(EO-co-PO)), and pluronic/poloxamer.

3. A titanium dioxide scaffold according to claim 1, wherein said biologically active substance is selected from the group consisting of a synthetic or natural bioactive molecule, a natural or synthetic drug, and/or a living cell.

4. A titanium dioxide scaffold according to claim 1, wherein said biologically active substance is selected from the group consisting of natural or recombinant bio-adhesives; natural or recombinant cell attachment factors; natural, recombinant or synthetic biopolymers; natural or recombinant blood proteins; natural or recombinant enzymes; natural or recombinant extracellular matrix proteins; natural or synthetic extracellular matrix biomolecules; natural or recombinant signal molecules, growth factors and hormones; natural, recombinant and synthetic peptides, synthetic peptide hormones; natural, recombinant or synthetic deoxyribonucleic acids; natural, recombinant or synthetic ribonucleotide acids; natural or recombinant receptors; enzyme inhibitors; drugs; biologically active anions and cations; vitamins; adenosine monophosphate (AMP), adenosine diphosphate (ADP) or adenosine triphosphate (ATP); marker biomolecules; amino acids; fatty acids; nucleotides (RNA and DNA bases), sugars, antibiotic substances, such as tetracyclines, and small biological organic molecules, such as statins and bisphosphonates.

5. A titanium dioxide scaffold according to claim 3, wherein said living cell is selected from the group consisting of mesenchymal stem cells, bone cells, pluripotent cells, bone precursors cells, vascular cells, precursors vascular cells, and stromal cells.

6. A titanium dioxide scaffold according to claim 1, wherein said polymer has a molecular weight (Mw) of 1,000-200,000 g/mol.

7. A titanium dioxide scaffold according to claim 1, wherein the hydrogel coating has a wet thickness of at least 1 μm.

8. A titanium dioxide scaffold according to claim 1, wherein said alginate is selected from the group consisting of sodium alginate, potassium alginate, calcium alginate, and strontium alginate.

9. A method for producing a titanium dioxide scaffold comprising a hydrogel coating comprising a biologically active substance, said method comprising the steps of:
   a) providing a titanium dioxide scaffold,
   b) providing an polymer solution comprising a biologically active substance(s) and about 1-10% w/v of a polymer selected from the group consisting of alginate, chitosan, hyaluronic acid, poly ethylene glycol (PEG), cellulose, poly(acrylic acid) (PAA), poly(glycolic acid) (PGA), poly(lactic acid) (PLA), PLA-PGA, PLA-PEG, dextran, dextran-PEG, starch, collagen based gels, agaroses, pluronic acid, heparan sulfate, glycosaminoglycans, polyethylene oxide (PEO), copolymer of ethylene oxide and propylene oxide (P(EO-co-PO)), and pluronic/poloxamer, to at least part of said titanium dioxide scaffold and then centrifuging the titanium dioxide scaffold, and
   c) effecting gelation of the polymer provided to the titanium dioxide scaffold in step b).

10. A medical implant comprising a titanium dioxide scaffold according to claim 1.

11. A titanium dioxide scaffold according to claim 7, wherein the hydrogel coating has a wet thickness of 1-20 μm.

12. The method of claim 9 further comprising:
   d) drying the titanium dioxide scaffold.

13. The method of claim 9 wherein steps b) and c) are repeated at least once.

14. The scaffold of claim 1, wherein the coating comprises multiple layers.

* * * * *

SEQUENCE LISTING

```
<160> NUMBER OF SEQ ID NOS: 48

<210> SEQ ID NO 1
<211> LENGTH: 25
<212> TYPE: PRT
<213> ORGANISM: Artificial sequence
<220> FEATURE:
<223> OTHER INFORMATION: Synthetic biomineralizing peptide

<400> SEQUENCE: 1

Pro Leu Val Pro Ser Gln Pro Leu Val Pro Ser Gln Pro Leu Val Pro
1               5                   10                  15

Ser Gln Pro Gln Pro Pro Leu Pro Pro
            20                  25

<210> SEQ ID NO 2
<211> LENGTH: 25
<212> TYPE: PRT
<213> ORGANISM: Artificial sequence
<220> FEATURE:
<223> OTHER INFORMATION: Synthetic biomineralizing peptide

<400> SEQUENCE: 2

Pro Leu Val Pro Ser Ser Pro Leu Val Pro Cys Cys Pro Leu Val Pro
1               5                   10                  15

Cys Cys Pro Ser Pro Pro Leu Pro Pro
            20                  25
```

<210> SEQ ID NO 3
<211> LENGTH: 25
<212> TYPE: PRT
<213> ORGANISM: Artificial sequence
<220> FEATURE:
<223> OTHER INFORMATION: Synthetic biomineralizing peptide

<400> SEQUENCE: 3

Pro His Gln Pro Met Gln Pro Gln Pro Val His Pro Met Gln Pro
1               5                   10                  15

Leu Pro Pro Gln Pro Pro Leu Pro Pro
            20                  25

<210> SEQ ID NO 4
<211> LENGTH: 25
<212> TYPE: PRT
<213> ORGANISM: Artificial sequence
<220> FEATURE:
<223> OTHER INFORMATION: Synthetic biomineralizing peptide

<400> SEQUENCE: 4

Pro Leu Val Pro Ser Tyr Pro Leu Val Pro Ser Tyr Pro Leu Val Pro
1               5                   10                  15

Ser Tyr Pro Tyr Pro Pro Leu Pro Pro
            20                  25

<210> SEQ ID NO 5
<211> LENGTH: 25
<212> TYPE: PRT
<213> ORGANISM: Artificial sequence
<220> FEATURE:
<223> OTHER INFORMATION: Synthetic biomineralizing peptide

<400> SEQUENCE: 5

Pro Leu Val Pro Ser Gln Pro Leu Val Pro Ser Gln Pro Leu Val Pro
1               5                   10                  15

Ser Gln Pro Gln Pro Pro Leu Pro Pro
            20                  25

<210> SEQ ID NO 6
<211> LENGTH: 25
<212> TYPE: PRT
<213> ORGANISM: Artificial sequence
<220> FEATURE:
<223> OTHER INFORMATION: Synthetic biomineralizing peptide

<400> SEQUENCE: 6

Pro Leu Val Pro Cys Cys Pro Leu Val Pro Cys Cys Pro Leu Val Pro
1               5                   10                  15

Cys Cys Pro Cys Pro Pro Leu Pro Pro
            20                  25

<210> SEQ ID NO 7
<211> LENGTH: 20
<212> TYPE: DNA
<213> ORGANISM: Artificial sequence
<220> FEATURE:
<223> OTHER INFORMATION: primer

<400> SEQUENCE: 7
gtaacccgtt gaaccccatt                                           20

<210> SEQ ID NO 8
<211> LENGTH: 20

```
<212> TYPE: DNA
<213> ORGANISM: Artificial sequence
<220> FEATURE:
<223> OTHER INFORMATION: primer

<400> SEQUENCE: 8
ccatccaatc ggtagtagcg                                                20

<210> SEQ ID NO 9
<211> LENGTH: 20
<212> TYPE: DNA
<213> ORGANISM: Artificial sequence
<220> FEATURE:
<223> OTHER INFORMATION: primer

<400> SEQUENCE: 9
acccagaaga ctgtggatgg                                                20

<210> SEQ ID NO 10
<211> LENGTH: 20
<212> TYPE: DNA
<213> ORGANISM: Artificial sequence
<220> FEATURE:
<223> OTHER INFORMATION: primer

<400> SEQUENCE: 10
cacattgggg gtaggaacac                                                20

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
tcgcctggga ggaggcgaaa                                                20

<210> SEQ ID NO 12
<211> LENGTH: 21
<212> TYPE: DNA
<213> ORGANISM: Artificial sequence
<220> FEATURE:
<223> OTHER INFORMATION: primer

<400> SEQUENCE: 12
tcttaaccgc tgtgctcccc g                                              21

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
agcaggcgtg gttgctggaa                                                20

<210> SEQ ID NO 14
<211> LENGTH: 22
<212> TYPE: DNA
<213> ORGANISM: Artificial sequence
<220> FEATURE:
<223> OTHER INFORMATION: primer

<400> SEQUENCE: 14
```
tttcacccgt gtcccacttg gc                                              22

<210> SEQ ID NO 15
<211> LENGTH: 21
<212> TYPE: DNA
<213> ORGANISM: Artificial sequence
<220> FEATURE:
<223> OTHER INFORMATION: primer

<400> SEQUENCE: 15
aggggagatg tgttccggcc a                                               21

<210> SEQ ID NO 16
<211> LENGTH: 20
<212> TYPE: DNA
<213> ORGANISM: Artificial sequence
<220> FEATURE:
<223> OTHER INFORMATION: primer

<400> SEQUENCE: 16
acacacagct gccgcactcg                                                 20

<210> SEQ ID NO 17
<211> LENGTH: 20
<212> TYPE: DNA
<213> ORGANISM: Artificial sequence
<220> FEATURE:
<223> OTHER INFORMATION: primer

<400> SEQUENCE: 17
gctgccagga gacagccgtg                                                 20

<210> SEQ ID NO 18
<211> LENGTH: 20
<212> TYPE: DNA
<213> ORGANISM: Artificial sequence
<220> FEATURE:
<223> OTHER INFORMATION: primer

<400> SEQUENCE: 18
gtcttgccgc ccttcggtgg                                                 20

<210> SEQ ID NO 19
<211> LENGTH: 20
<212> TYPE: DNA
<213> ORGANISM: Artificial sequence
<220> FEATURE:
<223> OTHER INFORMATION: primer

<400> SEQUENCE: 19
gctccacaaa cgagaaaagc                                                 20

<210> SEQ ID NO 20
<211> LENGTH: 20
<212> TYPE: DNA
<213> ORGANISM: Artificial sequence
<220> FEATURE:
<223> OTHER INFORMATION: primer

<400> SEQUENCE: 20
agcaagggga aaaggacact                                                 20

<210> SEQ ID NO 21
<211> LENGTH: 20
<212> TYPE: DNA
<213> ORGANISM: Artificial sequence
<220> FEATURE:
<223> OTHER INFORMATION: primer

<400> SEQUENCE: 21
agagcatgac cgatggattc                                           20

<210> SEQ ID NO 22
<211> LENGTH: 20
<212> TYPE: DNA
<213> ORGANISM: Artificial sequence
<220> FEATURE:
<223> OTHER INFORMATION: primer

<400> SEQUENCE: 22
ccttcttgag gttgccagtc                                           20

<210> SEQ ID NO 23
<211> LENGTH: 20
<212> TYPE: DNA
<213> ORGANISM: Artificial sequence
<220> FEATURE:
<223> OTHER INFORMATION: primer

<400> SEQUENCE: 23
gaaaatggag acggcgatag                                           20

<210> SEQ ID NO 24
<211> LENGTH: 20
<212> TYPE: DNA
<213> ORGANISM: Artificial sequence
<220> FEATURE:
<223> OTHER INFORMATION: primer

<400> SEQUENCE: 24
acccgagagt gtggaaagtg                                           20

<210> SEQ ID NO 25
<211> LENGTH: 20
<212> TYPE: DNA
<213> ORGANISM: Artificial sequence
<220> FEATURE:
<223> OTHER INFORMATION: primer

<400> SEQUENCE: 25
aacccagaca caagcattcc                                           20

<210> SEQ ID NO 26
<211> LENGTH: 20
<212> TYPE: DNA
<213> ORGANISM: Artificial sequence
<220> FEATURE:
<223> OTHER INFORMATION: primer

<400> SEQUENCE: 26
gagagcgaag ggtcagtcag                                           20

<210> SEQ ID NO 27
<211> LENGTH: 20
<212> TYPE: DNA
<213> ORGANISM: Artificial sequence
<220> FEATURE:
<223> OTHER INFORMATION: primer

<400> SEQUENCE: 27
ccgggagcag tgtgagctta                                           20

```
<210> SEQ ID NO 28
<211> LENGTH: 21
<212> TYPE: DNA
<213> ORGANISM: Artificial sequence
<220> FEATURE:
<223> OTHER INFORMATION: primer

<400> SEQUENCE: 28
tagatgcgtt tgtaggcggt c                                           21

<210> SEQ ID NO 29
<211> LENGTH: 20
<212> TYPE: DNA
<213> ORGANISM: Artificial sequence
<220> FEATURE:
<223> OTHER INFORMATION: primer

<400> SEQUENCE: 29
tctgcggcag gcattctcgg                                             20

<210> SEQ ID NO 30
<211> LENGTH: 23
<212> TYPE: DNA
<213> ORGANISM: Artificial sequence
<220> FEATURE:
<223> OTHER INFORMATION: primer

<400> SEQUENCE: 30
gtcactttca ccgggaggga gga                                         23

<210> SEQ ID NO 31
<211> LENGTH: 20
<212> TYPE: DNA
<213> ORGANISM: Artificial sequence
<220> FEATURE:
<223> OTHER INFORMATION: primer

<400> SEQUENCE: 31
actggctagg tggtggtcag                                             20

<210> SEQ ID NO 32
<211> LENGTH: 20
<212> TYPE: DNA
<213> ORGANISM: Artificial sequence
<220> FEATURE:
<223> OTHER INFORMATION: primer

<400> SEQUENCE: 32
ggtagggagc tgggttaagg                                             20

<210> SEQ ID NO 33
<211> LENGTH: 20
<212> TYPE: DNA
<213> ORGANISM: Artificial sequence
<220> FEATURE:
<223> OTHER INFORMATION: primer

<400> SEQUENCE: 33
gctccacaaa cgagaaaagc                                             20

<210> SEQ ID NO 34
<211> LENGTH: 20
<212> TYPE: DNA
<213> ORGANISM: Artificial sequence
<220> FEATURE:
<223> OTHER INFORMATION: primer
```

```
<400> SEQUENCE: 34
agcaagggga aaaggacact                                              20

<210> SEQ ID NO 35
<211> LENGTH: 20
<212> TYPE: DNA
<213> ORGANISM: Artificial sequence
<220> FEATURE:
<223> OTHER INFORMATION: primer

<400> SEQUENCE: 35
acttccatcc agttgccttc                                              20

<210> SEQ ID NO 36
<211> LENGTH: 20
<212> TYPE: DNA
<213> ORGANISM: Artificial sequence
<220> FEATURE:
<223> OTHER INFORMATION: primer

<400> SEQUENCE: 36
tttccacgat ttcccagaga                                              20

<210> SEQ ID NO 37
<211> LENGTH: 20
<212> TYPE: DNA
<213> ORGANISM: Artificial sequence
<220> FEATURE:
<223> OTHER INFORMATION: primer

<400> SEQUENCE: 37
ctctgctcct cctgttcgac                                              20

<210> SEQ ID NO 38
<211> LENGTH: 20
<212> TYPE: DNA
<213> ORGANISM: Artificial sequence
<220> FEATURE:
<223> OTHER INFORMATION: primer

<400> SEQUENCE: 38
acgaccaaat ccgttgactc                                              20

<210> SEQ ID NO 39
<211> LENGTH: 20
<212> TYPE: DNA
<213> ORGANISM: Artificial sequence
<220> FEATURE:
<223> OTHER INFORMATION: primer

<400> SEQUENCE: 39
catctcccct tcgtttttga                                              20

<210> SEQ ID NO 40
<211> LENGTH: 20
<212> TYPE: DNA
<213> ORGANISM: Artificial sequence
<220> FEATURE:
<223> OTHER INFORMATION: primer

<400> SEQUENCE: 40
ccaaatccga tgtttctgct                                              20

<210> SEQ ID NO 41
```

```
<211> LENGTH: 20
<212> TYPE: DNA
<213> ORGANISM: Artificial sequence
<220> FEATURE:
<223> OTHER INFORMATION: primer

<400> SEQUENCE: 41
gacaagaagc ccttcactgc                                           20

<210> SEQ ID NO 42
<211> LENGTH: 20
<212> TYPE: DNA
<213> ORGANISM: Artificial sequence
<220> FEATURE:
<223> OTHER INFORMATION: primer

<400> SEQUENCE: 42
agactgcgcc tggtagttgt                                           20

<210> SEQ ID NO 43
<211> LENGTH: 20
<212> TYPE: DNA
<213> ORGANISM: Artificial sequence
<220> FEATURE:
<223> OTHER INFORMATION: primer

<400> SEQUENCE: 43
tgggagcaga agacattgaa                                           20

<210> SEQ ID NO 44
<211> LENGTH: 20
<212> TYPE: DNA
<213> ORGANISM: Artificial sequence
<220> FEATURE:
<223> OTHER INFORMATION: primer

<400> SEQUENCE: 44
gtgtcttggt cgccattttt                                           20

<210> SEQ ID NO 45
<211> LENGTH: 20
<212> TYPE: DNA
<213> ORGANISM: Artificial sequence
<220> FEATURE:
<223> OTHER INFORMATION: primer

<400> SEQUENCE: 45
tcttcaagcc atcctgtgtg                                           20

<210> SEQ ID NO 46
<211> LENGTH: 20
<212> TYPE: DNA
<213> ORGANISM: Artificial sequence
<220> FEATURE:
<223> OTHER INFORMATION: primer

<400> SEQUENCE: 46
atctgcatgg tgatgttgga                                           20

<210> SEQ ID NO 47
<211> LENGTH: 20
<212> TYPE: DNA
<213> ORGANISM: Artificial sequence
<220> FEATURE:
<223> OTHER INFORMATION: primer

<400> SEQUENCE: 47
```

```
gcaagtagcg ccaatctagg                                              20

<210> SEQ ID NO 48
<211> LENGTH: 20
<212> TYPE: DNA
<213> ORGANISM: Artificial sequence
<220> FEATURE:
<223> OTHER INFORMATION: primer

<400> SEQUENCE: 48
gcttcaccct cgaaatggta                                              20
```